US008106257B2

(12) United States Patent
Arruda et al.

(10) Patent No.: US 8,106,257 B2
(45) Date of Patent: Jan. 31, 2012

(54) ALTERING LIGNIN AND WOOD DENSITY

(75) Inventors: Paulo Arruda, Campinas (BR); Fabio Papes, Campinas (BR); Isabel Rodrigues Gerhardt, Campinas (BR)

(73) Assignee: Monsanto Do Brasil Ltda., Sao Paulo (BR)

( * ) Notice: Subject to any disclaimer, the term of this patent is extended or adjusted under 35 U.S.C. 154(b) by 298 days.

(21) Appl. No.: 11/676,078

(22) Filed: Feb. 16, 2007

(65) Prior Publication Data

US 2008/0058510 A1 Mar. 6, 2008

Related U.S. Application Data

(63) Continuation-in-part of application No. PCT/BR2005/000162, filed on Aug. 5, 2005.

(60) Provisional application No. 60/602,440, filed on Aug. 18, 2004.

(51) Int. Cl.
*C12N 15/82* (2006.01)
*C12N 15/63* (2006.01)
*C12N 15/09* (2006.01)
*C12N 15/00* (2006.01)
*A01H 5/00* (2006.01)
*A01H 5/10* (2006.01)

(52) U.S. Cl. ........ 800/290; 800/287; 800/278; 800/295; 435/320.1; 435/468; 536/23.1; 536/23.2; 536/23.6

(58) Field of Classification Search ........................ None
See application file for complete search history.

(56) References Cited

U.S. PATENT DOCUMENTS

| 4,407,956 A | 10/1983 | Howell |
| 2002/0124281 A1* | 9/2002 | Chiang et al. ................. 800/278 |
| 2003/0221213 A1 | 11/2003 | Rommens et al. |
| 2004/0107455 A1 | 6/2004 | Rommens et al. |
| 2004/0143874 A1 | 7/2004 | Moller et al. |

FOREIGN PATENT DOCUMENTS

| WO | WO 95/14092 | 5/1995 |
| WO | WO 00/52168 | 9/2000 |
| WO | WO 01/59084 A1 | 8/2001 |
| WO | WO 03/013226 A2 | 2/2003 |
| WO | WO 2004/076625 A2 | 9/2004 |
| WO | WO 2005/096805 A2 | 10/2005 |
| WO | WO 2006/084073 A2 | 10/2006 |

OTHER PUBLICATIONS

Paramale et al 1997 GenBank accession AF033100, provided in Applicant IDS.*
European Search Report 05770849.7 dated Jun. 10, 2008.
Bhavna Waie et al., "Effect of increased polyamine biosynthesis on stress responses in transgenic tobacco by introduction of human S-adenosylmethionine gene", Plant Science 164 (2003) 727-734.
Malabika Roy et al., "Overexpression of S-adenosylmethionine decarboxylase gene in rice increases polyamine level and enhances sodium chloride-stress tolerance", Plant Science 163 (2002) 987-992.
Pham Thu-Hang et al., "Expression of a Heterologous *S-Adenosylmethionine Decarboxylase* cDNA in Plants Demonstrates That changes in S-Adenosyl-L-Methionine Decarboxylase Activity Determine Levels of the Higher Polyamines Spermidine and Spermine", Plant Physiology Aug. 2002, vol. 129, pp. 1744-1754.
Database EMBL Apr. 3, 1997, "*Nicotiana tabacum* S-adenosylmethionine decarboxylase mRNA, complete cds", XP002481345, retrieved from EBI accession No. EMBL:U091924, Database accession No. U91924 *the whole document*.
Database EMBL, Jan. 27, 1998, "*Nicotiana tabacum* S-adenosylmethionine decarboxylase gene, complete cds", XP002481346 retrieved from EBI accession No. EMBL:AF033100 Database accession No. AF033100 *the whole document*.
Bo Shen et al., "High free-methionine and decreased lignin content result from a mutation in the *Arabidopsis* S-adenosyl-L-methionine synthetase 3 gene", The Plant Journal (2002) 29(3), 371-380.
Yi Quan et al., "Genetic manipulation of polyamine metabolism in poplar II: effects on ethylene biosynthesis", Plant Physiol. Biochem. 40(2002) 929-937.
Csaba Koncz et al., "The promoter of $T_L$-DNA gene 5 controls the tissue-specific expression of chimaeric genes carried by a novel type of *Agrobacterium* binary vector", Mol Gen Genet (1986) 204:383-396.
Ko Shimamoto et al., "Fertile transgenic rice plants regenerated from transformed protoplasts", Nature, vol. 338, Mar. 16, 1989, pp. 274-276.
T. Markussen et al., "Identification of Molecular Markers for Selected Wood Properties of Norway Spruce *Picea abies* L. (Karst.) I. Wood Density", Silvae Genetica 53, 2 (2004), pp. 45-50.
Marie Baucher et al., "Lignin: Genetic Engineering and Impact on Pulping", Critical Reviews in Biochemistry and Molecular Biology, 38:305-350, 2003.
Wout Boerjan et al., "Lignin Biosynthesis", Annu. Rev, Plant Biol. 2003, 54:519-546.
Ross Whetten et al., "Genetic engineering of wood", Forest Ecology & Management, 43 (1991) 301-316.
Ronald Sederoff et al., "Genetic Regulation of Lignin Biosynthesis and the Potential Modification of Wood by Genetic Engineering in Loblolly Pine", Genetic Engineering of Plant Secondary Metabolism, vol. 28, Chapter 12, Plenum Press, New York, 1994, pp. 313-355.
Malcolm M. Campbell et al., "Variation in Lignin Content and Composition", Plant Physiol. (1996)110:3-13.
Marie Baucher et al., "Red Xylem and Higher Lignin Extractability by Down-Regulating a Cinnamyl Alcohol Dehydrogenase in Poplar", Plant Physiol. (1996) 112:1479-1490.
Ann O'Connell et al., "Improved paper pulp from plants with suppressed cinnamoyl-CoA reductase or cinnamyl alcohol dehydrogenase", Transgenic Research 11:495-503, 2002.
Stephane Ravanel et al., "The specific features of methionine biosynthesis and metabolism in plants", Proc. Natl. Acad. Sci. USA, vol. 95, pp. 7805-7812, Jun. 1998.
Jose Luis P.C. Louzada, "Genetic correlations between wood density components in *Pinus pinaster* Ait.", Ann. For. Sci. 60 (2003), 285-294.

(Continued)

*Primary Examiner* — Brent T Page
(74) *Attorney, Agent, or Firm* — Thompson Coburn LLP; Charles P. Romano

(57) ABSTRACT

In angiosperm and gymnosperm plants, overexpressing a SAMdc nucleotide sequence can decrease lignin content and, for plants with woody tissue, increase wood density.

35 Claims, 18 Drawing Sheets

OTHER PUBLICATIONS

Jose Luis P.C. Louzada, "The heritability of wood density components in *Pinus pinaster* Ait. And the implications for tree breeding", Ann. For. Sci. 59 (2002) 867-873.

M.E. Devey et al., "QTL associations for density and diameter in *Pinus radiata* and the potential for maker-aided selection", Theor. Appl. Genet. (2004), 108:516-524.

Dario Grattapaglia et al., "Genetic Mapping of Quantitative Trait Loci Controlling Growth and Wood Quality Traits in *Eucalyptus grandis* Using a Maternal Half-Sib Family and RAPD Markers", Genetics 144:1205-1214, Nov. 1996.

S.L. Beaucage et al., "Deoxynucleoside Phosphoramidites—A New Class of Key Intermediates for Deoxypolynucleotide Synthesis", Tetrahedron Letters, vol. 22, No. 20, pp. 1859-1862, 1981.

M.D. Matteucci et al., "Synthesis of Deoxyoligonucleotides on a Polymer Support", J. Am. Chem. Soc. 1981, 103, 3185-3191.

Russell L. Malmberg et al., "Molecular Genetic Analysis of Plant Polyamines", Critical Reviews in Plant Sciences, 17(2): 199-224 (1998).

Michael L. Roderick et al., "Linking wood density with tree growth and environment: a theoretical analysis based on the motion of water", New Phytologist (2001) 149: 473-485.

Katherine A. Preston et al., "Wood density and vessel traits as distinct correlates of ecological strategy in 51 California coast range angiosperms", New Phytologist, (2006), 170:807-818.

D.S. Thomas et al., "Changes in wood density of *Eucalyptus camaldulensis* due to temperature—the physiological link between water viscosity and wood anatomy", Forest Ecology and Management 193 (2004) 157-165.

Irene M.C. Van Amsterdam et al., "A New Type 2 Copper Cysteinate Azurin", The Journal of Biological Chemistry, vol. 277, No. 46, Nov. 15, 2002, pp. 44121-44130.

Marion M. Bradford, "A Rapid and Sensitive Method for the Quantitation of Microgram Quantities of Protein Utilizing the Principle of Protein Dye Binding", Analytical Biochemistry 72, 248-254, 1976.

Stephen F. Altschul et al., "Gapped BLAST and PSI-BLAST: a new generation of protein database search programs", Nucleic Acids Research, 1997, vol. 25, No. 17, pp. 3389-3402.

Charles J. Thompson et al., "Characterization of the herbicide resistance gene bar from *Streptomyces hygroscopicue*", The EMBO Journal, vol. 6, No. 9, pp. 2519-2523, 1987.

Peter R. Beetham et al., "A tool for functional plant genomics: Chimeric RNA/DNA oligonucleotides cause in vivo gene specific mutations", Proc. Natl. Acad. Sci. USA, vol. 96, pp. 8774-8778, Jul. 1999.

Tong Zhu et al., "Targeted manipulation of maize genes in vivo using chimeric RNA/DNA oligonucleotides", Proc. Natl. Acad. Sci., USA, vol. 96, pp. 8768-8773, Jul. 1999.

Theodore M. Klein et al., "Particle bombardment: a universal approach for gene transfer to cells and tissues", Current Opinion in Biotechnology 1993, 4:583-590.

Nicole Bechtold et al., "In planta Agrobacterium mediated gene transfer by infiltration of adult *Arabidopsis thaliana* plants", C. R. Acad. Sci. Paris Sciences De La Vie/Life Sciences, 1993:316:1194-1199.

Jerzy Paskowski et al., "Direct gene transfer to plants", The EMBO Journal vol. 3, No. 12, pp. 2717-2722, 1984.

Laslo Sagi et al., "Transient gene expression in electroporated banana (Musa spp., cv. 'Bluggoe', ABB group) protoplasts isolated from regenerable embryogenic cell suspensions", Plant Cell Reports (1994) 13:262-266.

R. Nagel et al., "Eelctroporation of binary Ti plasmid vector into *Agrobacterium tumefaciens* and *Agrobacterium rhizogenes*", FEMS Microbiology Letters 67 (1990) 325-328.

Wilm Broothaerts et al., "Gene transfer to plants by diverse species of bacteria," Nature, vol. 433, Feb. 10, 2005, pp. 629-633.

Horst Lorz et al., "Gene transfer to cereal cells mediated by protoplast transformation", Mol. Gen. Genet. (1985) 199:178-182.

A. De La Pena et al., "Transgenic rye plants obtained by injecting DNA into young floral tillers", Nature, vol. 325, Jan. 15, 1987, pp. 274-276.

Carol A. Rhodes et al., "Genetically Transformed Maize Plants from Protoplasts", Science vol. 240, Apr. 8, 1988, pp. 204-207.

Jerome Chave et al., "Regional and Phylogenetic Variation of Wood Density Across 2456 Neotropical Tree Species", Ecological Applications, 16(6), 2006, pp. 2356-2367.

T. Kent Kirk et al., "[12] Lignin Determination", Methods in Enzymology, vol. 161, pp. 87-101 (1988).

K. Iiyama et al., "An improved acetyl bromide procedure for determining lignin in woods and wood pulps", Wood Sci. Technol. 22: 271-280 (1988).

Joachim Messing, "[2] New M13 Vectors for Cloning", New Vectors for Cloning Genes, Methods in Enzymology, vol. 101, 1983, pp. 20-79.

C. Rolando et al., "6.4 Thioacidolysis", Methods in Lignin Chemistry, 1992, pp. 334-349.

Isabel Miranda et al., "Provenance and site variation of wood density in *Eucalyptus globulus* Labill. At harvest age and its relation to a non-destructive early assessment", Forest Ecology and Management 149 (2001) pp. 235-240.

Michael Bevan et al., "Binary Agrobacterium vectors for plant transformation", Nucleic Acids Research vol. 12, No. 22, 1984, pp. 8711-8721.

R.B. Horsch et al., "A Simple and General Method for Transferring Genes Into Plants", Science, vol. 227, Mar. 8, 1985, pp. 1229-1231.

Wen Jing Hu et al., "Compartmentalized expression of two structurally and functionally distinct 4-coumarate:CoA ligase genes in aspen (*Populus tremuloides*)", Proc. Natl. Acad. Sci. USA, vol. 95, pp. 5407-5412, Apr. 1998.

Jane Aldrich et al., "RAPD Analysis in Flax: Optimization of Yield and Reproducibility using KlenTaq 1DNA Polymerase, Chelex 100, and Gel Purification of Genomic DNA", Plant Molecular Biology Reporter, vol. 11(2) 1993 pp. 128-141.

Barbara A. Moffatt et al., "The adenine phosphoribosyltransferase-encoding gene of *Arabidopsis thaliana*", Gene, 143 (1994) 211-216.

Ruiqin Zhong et al., "Ectopic Deposition of Lignin in the Pith of Stems of Two *Arabidopsis* Mutants", Plant Physiology, May 2000, vol. 123, pp. 59-69.

Astrid Patzlaff et al., "Characterisation of a pine MYB that regulates lignification" The Plant Journal (2003) 36, 743-754.

Barbara A. Moffatt et al., "Sustaining S-adenosyl-L-methionine-dependent methyltransferase activity in plant cells", Physiologia Plantarum vol. 113, Issue 4, Dec. 2001, Abstract.

Kusano T. Berberich et al., "Polyamines: essential factors for growth and survival", Planta. Aug. 2008 (3): Abstract.

T. Capell et al., "Modulation of the polyamine biosynthetic pathway in transgenic rice confers tolerance to drought stress", Proc Natl Acad Sci USA 2004, 101(26) Abstract.

T. Takahashi et al., "Polyamines: ubiquitous polycations with unique roles in growth and stress responses", Ann Bot. Jan. 2010 105(1) Abstract.

Richard Walden et al., "Polyamines: Small Molecules Triggering Pathways in Plant Growth and Development[1,2]", Plant Physiol. (1997) 113: pp. 1009-1013.

* cited by examiner

FIG. 17A   FIG. 17B
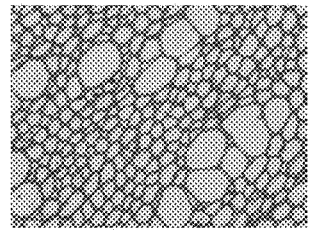 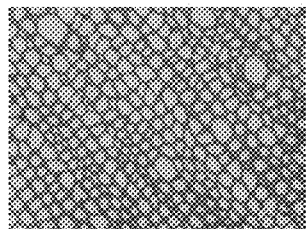
FIG. 17C
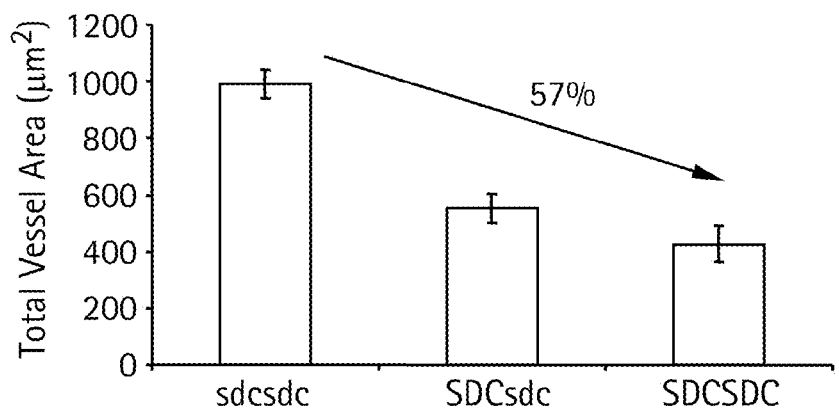
FIG. 18
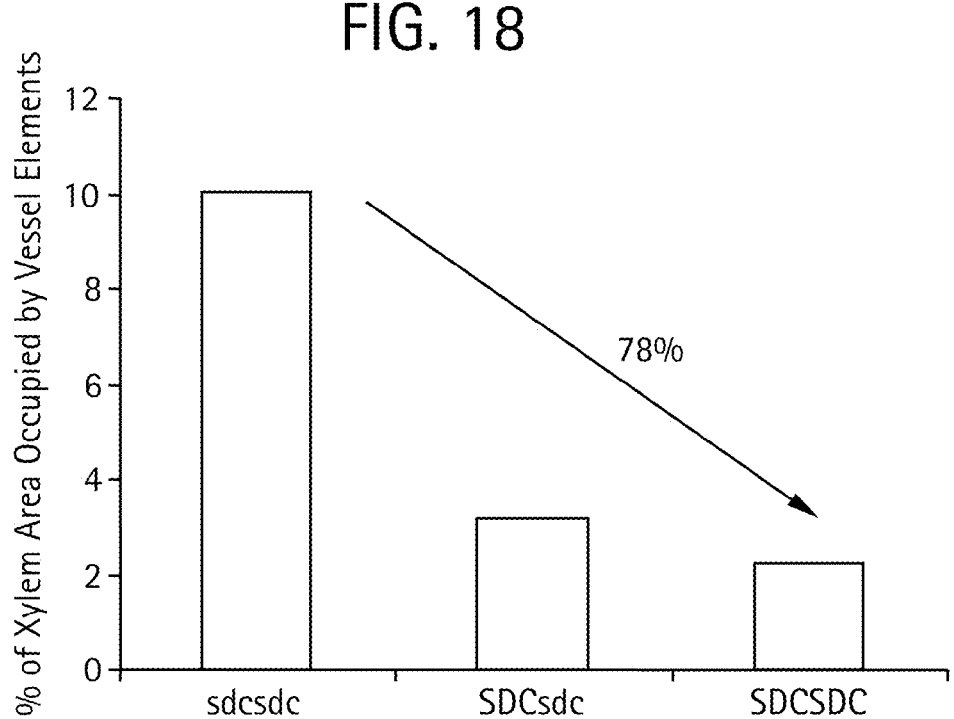

FIG. 19A
FIG. 19B
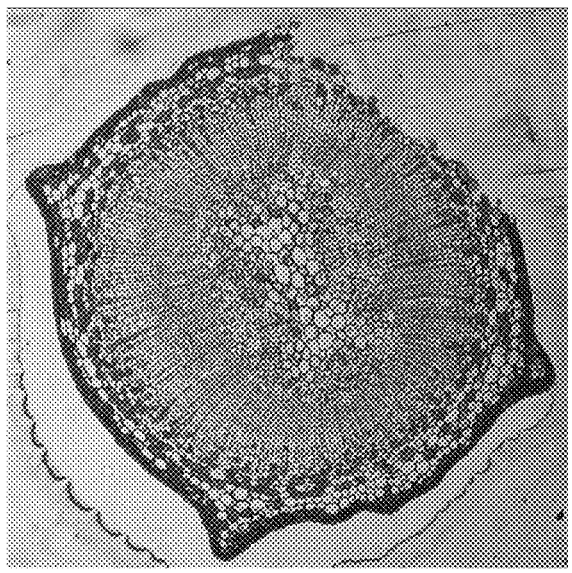
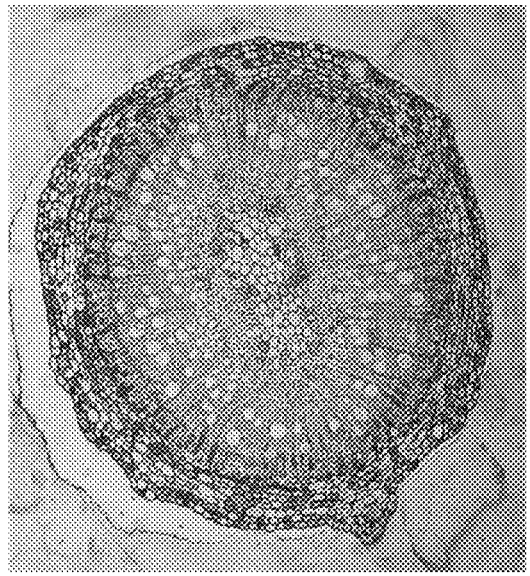

ALTERING LIGNIN AND WOOD DENSITY

CROSS-REFERENCE TO RELATED PATENT APPLICATIONS

This application is a continuation-in-part of PCT/BR2005/000162, filed under 35 U.S.C. §371, which was published in English and which claims the benefit of U.S. Provisional Application No. 60/602,440, filed Aug. 18, 2004. The contents of PCT/BR2005/000162 are incorporated herein by reference.

FIELD OF THE INVENTION

The present invention relates to the field of molecular biology and regulation of wood composition. Thus, the invention relates, inter alia, to methodology and constructs for increasing wood density and reducing lignin content in plants.

BACKGROUND OF THE INVENTION

Wood Quality, as used by the pulp and paper industries, refers to a series of wood components that, at the end of the processing, affect cellulose yield. The most studied wood components affecting wood quality include lignin content, the proportion of monolignols siryngil and guaiacyl (S/G), the module of elasticity, spiral grain, fiber characteristics and wood density. T. Markussen et al., *Wood Density Silvae Genetica* 53: 45-50 (2004). Of these components, lignin content and wood density significantly impact cellulose yield.

Lignin Content

Lignin is one of the major products of the general phenylpropanoid pathway, and it is one of the most abundant organic molecules in the biosphere. Lignin accounts for 20-30% of the dry weight of trees and through a process called lignification, lignin is deposited in the cell walls of supporting and conductive tissues, thereby providing rigidity to the wood and structural integrity to tracheary elements. Baucher et al., *Crit. Rev. Biochem. Mol. Biol.* 38: 305-50 (2003). Lignification also occurs following microbial infection or wounding and protects tissues from pathogen penetration. Baucher et al., (2003); Boerjan et al., *Annu. Rev. Plant. Biol.* 54: 519-46 (2003); Crawford, LIGNIN BIODEGRADATION AND TRANSFORMATION, New York: John Wiley and Sons (1981).

Lignin's resistance to degradation significantly limits the use of lignocellulosic materials, as lignin must be removed during pulping and papermaking and this requires environmentally hazardous chemicals. Baucher et al., (2003); Whetten et al., *Forest Ecol. Management* 43: 301 (1991). Current research efforts aim to develop trees with reduced lignin content, thereby reducing the amount of chemicals needed for kraft pulping. Baucher et al., (2003); Sederoff et al., GENETIC ENGINEERING OF PLANT SECONDARY METABOLISM, New York, Plenum Press (1994).

Lignins are the result of dehydrogenative polymerization of monolignols, notably p-coumaryl, coniferyl and synapyl alcohols. Reviewed in Boejan et al., *Annu. Rev. Plant. Biol.* 54: 519-46 (2003). Different plant species or cell types harbor lignin polymers composed of varying proportions of these three monolignols. For example, gymnosperm lignin is primarily composed of guaiacyl (coniferyl-derived) units, whereas angiosperm lignin is primarily composed of guaiacyl and syringyl (synapyl-derived) units. Grass lignin, on the other hand, is a mixture of guaiacyl, syringyl and p-hydroxylphenyl (coumaryl-derived) units. Campbell and Sederoff, *Plant. Physiol.* 110: 3-13 (1996). It is well known that the monomeric composition of lignin has a significant effect on its chemical degradation during industrial pulping. Baucher et al., *Plant Physiol.* 112: 1479-1490 (1996); O'Connell et al., *Transgenic Res.* 11: 495-503 (2002); Baucher et al., *Critical Reviews in Biochemistry and Molecular Biology* 38: 305-50 (2003).

Several steps in the monolignol biosynthesis pathway, leading to lignin synthesis, represent SAM-dependent methylation reactions, evidencing the importance of this methionine-derived substrate in lignin biosynthesis. SAM is synthesized from methionine by the action of one or more SAM synthetase isoforms and is used as a cofactor in many processes in plant cells besides lignification, such as DNA methylation and ethylene, biotin and polyamine biosynthesis. Ravanel et al., *Proc. Natl. Acad. Sci. USA* 95: 7805-7812 (1998).

Wood Density

In the assessment of raw-material quality for pulping, wood density is another important parameter. Wood density significantly influences the yield and quality of fibrous and solid wood products, as well as strength, machinability, conversion, wearability, and paper yield. Bamber and Burley, The wood properties of Radiata Pine. Commonwealth Agricultural Bureau. Slough, p. 84 (1983). High wood densities are advantageous because they correspond to higher pulp yields on a raw-material volume basis, and to a better use of digestor capacity. From the vantage point of forest production, high wood density combined with high volume growth maximizes production on the unit area basis. Miranda et al., *Forest Ecology and Management* 149: 235-40 (2001).

While wood density is a critical factor in the profitability of kraft pulp production, increasing wood density is difficult because it is a complex trait that is not easily managed for breeding purposes. For temperate softwood, the average ring density depends on the earlywood and latewood proportion and the relative densities of each of them. Thus, improved wood density is the result of various combinations of components that could be changed by manipulating one or more components. Louz, *Ann. For. Sci.* 60: 285-94 (2003). Further adding to the difficulties associated with increasing wood density, hardwood tree improvement is a slow process because of the lengthy time needed for breeding a single generation. This process is made even more difficult by the changes that occur during the transition from juvenility to maturity.

Although the wood density is a complex trait, it presents great variations between trees as well as high heritability and reduced Genotype×Environment interactions. In analyzing wood densities in different species, it has been shown that wood density has a strong genetic component. Louzada and Fonseca, *Ann. For. Sci.* 59: 867-73 (2002).

There is consensus amongst the forest breeding community that if one could develop methods that allow early selection at the individual level, this would be of considerable value for increasing the genetic gain per unit time. In this regard, current research efforts are focused on identifying molecular markers that cosegregate with complex traits, such as wood basic density. Grattapaglia et al., *Genetics* 144: 1205-14 (1996). Most of these studies have associated quantitative trait loci (QTLs) with juvenile wood density. For example, four markers showed a consistent association with juvenile wood density in segregating populations of *Pinus radiata*. Devey et al., *Theor Appl Genet* 108: 516-24 (2004).

Accordingly, there is a continuing need to identify genes whose expression can be affected to increase wood density and decrease lignin in plants, in particular, woody tree species.

SUMMARY OF THE INVENTION

In one aspect, the invention provides a nucleic acid construct comprising a SAMdc nucleotide sequence operably linked to a xylem-preferred promoter. In one embodiment, a plant comprises the nucleic acid construct. In further embodiments, the plant is an angiosperm or gymnosperm.

In another aspect, the invention provides a plant or part thereof that overexpresses a nucleotide sequence encoding a SAMdc enzyme, which nucleotide sequence is under the control of a xylem-preferred promoter, such that said plant has reduced lignin levels compared with a control plant. In further embodiments, the plant is an angiosperm or gymnosperm. In even further embodiments, the plant is a woody tree, *Eucalyptus, Populus*, and *Pinus*. In another embodiment, the part of the plant is selected from the group consisting of a leaf, a stem, a flower, an ovary, a fruit, a seed, and a callus. In another embodiment, the invention provides progeny of the plant.

In another aspect, the invention provides a method for decreasing lignin content in a plant, comprising: (a) introducing into a plant cell a nucleic acid construct comprising, in the 5' to 3' direction, a xylem-preferred promoter operably linked to a SAMdc nucleotide sequence; (b) regenerating transgenic plants from said plant cell; and (c) selecting a transgenic plant having decreased lignin content relative to a control plant. In one embodiment, the plant is an angiosperm. In another embodiment, the plant is a gymnosperm. In further embodiments, the plant is *Eucalyptus, Populus*, and *Pinus*. In another embodiment, the nucleic acid is selected from the group consisting of: (a) a nucleotide sequence set forth in any of SEQ ID NO: 1, 3, 5, 7, 9, 11, 13, 15, 17, 19, 24, and 26; (b) a nucleotide sequence that encodes a polypeptide having the amino acid sequence set forth in any of SEQ ID NO: 2, 4, 6, 8, 10, 12, 14, 16, 18, 25, and 27 (c) a nucleotide sequence that differs from the nucleotide sequences of (a) or (b) due to degeneracy of the genetic code and encodes a polypeptide with SAMdc enzyme activity.

In another aspect, the invention provides a method for increasing the ratio of syringyl lignin to guaiacyl lignin in a woody plant, comprising overexpressing a SAMdc nucleotide sequence with a xylem-preferred promoter.

In another aspect, the invention provides a method for increasing wood density in a plant, comprising (a) introducing into a plant cell a nucleic acid construct comprising, in the 5' to 3' direction, a xylem-preferred promoter operably linked to a SAMdc nucleotide sequence; (b) regenerating transgenic plants from said plant cell; and (c) selecting a transgenic plant having reduced vessel area and reduced vessel density relative to a control plant. In one embodiment, the plant is an angiosperm.

In another embodiment, the plant is a gymnosperm. In further embodiments, the plant is *Eucalyptus, Populus*, and *Pinus*. In further embodiments, wood pulp and wood fiber are obtained from the transgenic plant.

In another aspect, the invention provides a method for increasing wood density and decreasing lignin content in a plant, comprising: (a) introducing into a plant cell a nucleic acid construct comprising, in the 5' to 3' direction, a xylem-preferred promoter operably linked to a SAMdc nucleotide sequence; (b) regenerating transgenic plants from said plant cell; and (c) selecting a transgenic plant having increased wood density and decreased lignin content relative to a control plant. In one embodiment, the plant is an angiosperm. In another embodiment, the plant is a gymnosperm. In another embodiment, the plant is *Eucalyptus, Populus*, and *Pinus*.

In another aspect, the invention provides a method of making wood pulp, comprising (a) introducing into a plant cell a nucleic acid construct comprising, in the 5' to 3' direction, a xylem-preferred promoter operably linked to a SAMdc nucleotide sequence; (b) regenerating transgenic plants from said plant cell; (c) selecting a transgenic plant having increased wood density and decreased lignin content relative to a control plant; and (d) producing wood pulp from said transgenic plant. In one embodiment, the xylem-preferred promoter is selected from the group consisting of TUB gene promoter, LTP gene promoter, 4CL gene promoter, and C4H gene promoter.

In another aspect, the invention provides method of making wood fiber, comprising (a) introducing into a plant cell a nucleic acid construct comprising, in the 5' to 3' direction, a xylem-preferred promoter operably linked to a SAMdc nucleotide sequence; (b) regenerating transgenic plants from said plant cell; (c) selecting a transgenic plant having increased wood density and decreased lignin content relative to a control plant; and (d) producing wood fiber from said transgenic plant.

BRIEF DESCRIPTION OF THE DRAWINGS

FIG. 17 shows the area of vessel elements (mean of 100 vessel elements) of three genotypes of a T1 transgenic *Nicotiana benthamiana* plants (line 11B) transformed with the plant expression plasmidial vector pALELLYX-Nt. (A) sdcsdc genotype; (B) SDCSDC genotype; (C) reduction on the area of vessel elements of the T1 transgenic plants (line 11B).

FIG. 18 shows the percentage of xylem area occupied by vessel elements of three genotypes of a T1 transgenic *Nicotiana benthamiana* plants (line 11B) transformed with the plant expression plasmidial vector pALELLYX-Nt.

FIG. 19 shows a cross-section of lateral shoot of 6 months old *Eucalyptys* plants. (A) is a cross-section of the transgenic event A.12.3 transformed with the plant expression plasmidial vector pALELLYX-Pd; (B) is a cross-section of a wild-type plant.

DETAILED DESCRIPTION OF THE PREFERRED EMBODIMENTS

Figure 1:
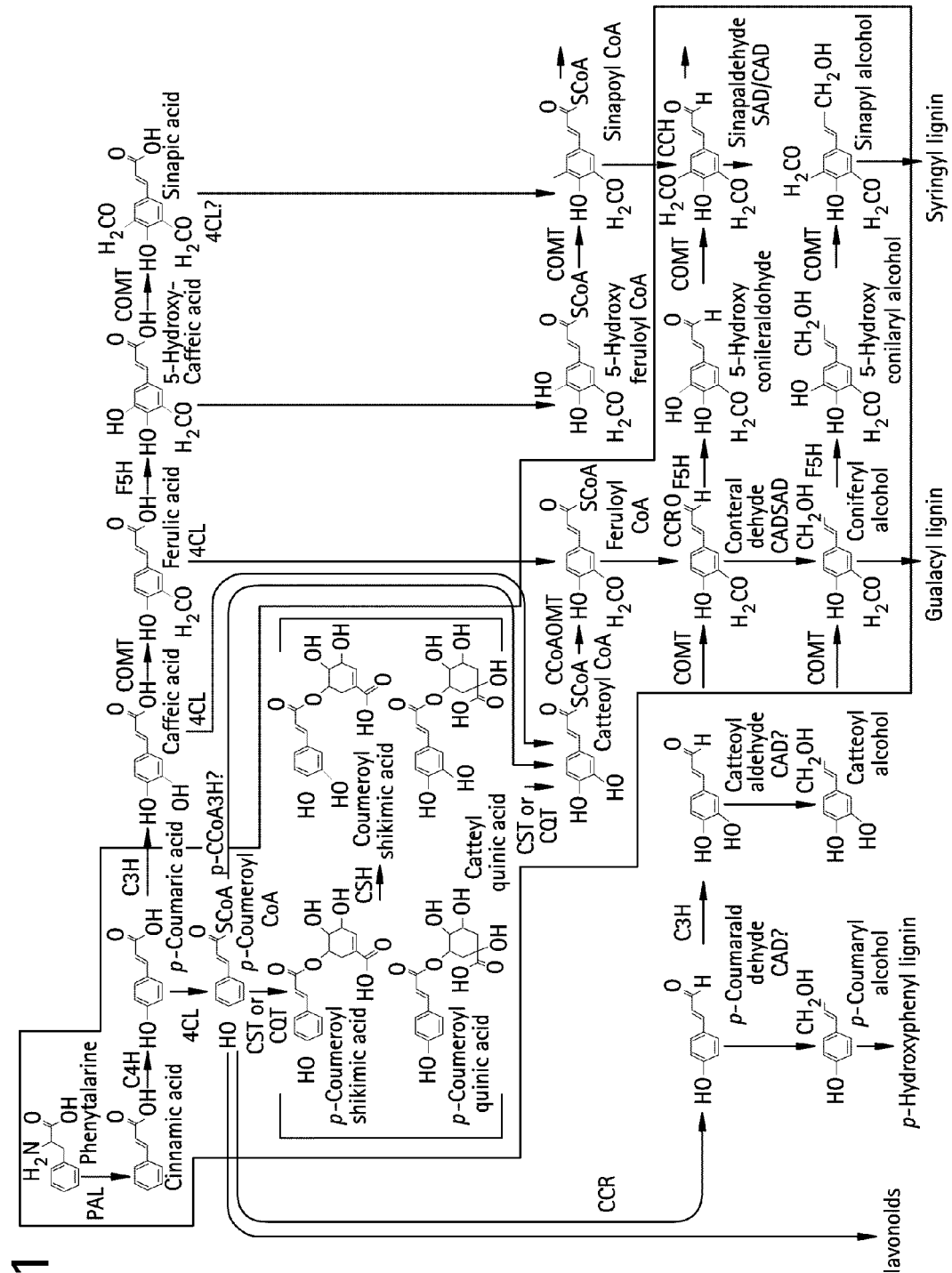
FIG. 1 illustrates the lignin biosynthesis pathway, showing in details the compounds, reactions and enzymes involved in synthesis of monolignols, the building blocks of the three kinds of lignin, represented at the bottom of the picture as p-hydroxyphenyl, guaiacyl and syringyl lignins.

The present inventors realized that overexpressing a polynucleotide encoding SAMdc, an enzyme that converts SAM into decarboxylated SAM, reduces the amount of SAM available for SAM-dependent methylation of intermediates in the monolignol biosynthesis pathway, thereby impairing lignin biosynthesis and deposition, without affecting other plant functions. Moreover, they discovered that overexpressing a polynucleotide encoding SAMdc in a plant causes a reduction in the number of vessels and vessel area in the plant, as well as a reduction in lignin content. Because vessel number and area negatively correlate with wood density, overexpressing a gene encoding a SAMdc enzyme produces a plant with increased wood density and reduced insoluble lignin content. Thus, the present invention provides constructs and methodology for using a single gene to increase wood density and decrease lignin content in angiosperm and gymnosperm plants.

Accordingly, the present invention relates to methodology and compositions for reducing lignin and increasing wood density in plant tissues or cells, such as woody angiosperm and gymnosperm xylem, by controlling the activity of SAMdc. Pursuant to this aspect of the invention, a polynucleotide encoding a SAMdc enzyme is introduced into plant cells or whole plants, which sequence, when expressed in vascular cells of angiosperms or xylary tracheids of gymnosperms, reduces the amount of SAM available for the monolignol biosynthesis pathway, leading to reduced lignin and increased wood density.

Because the present inventors have discovered methodology and compositions for increasing wood density and decreasing lignin content, the inventive methods and compositions may be used, for example, to increase pulp and cellulose fiber yields during pulp and paper processing.

All technical terms in this description are commonly used in biochemistry, molecular biology and agriculture, respectively, and can be understood by those skilled in the field of this invention. Those technical terms can be found in: MOLECULAR CLONING: A LABORATORY MANUAL, 3rd ed., vol. 1-3, ed. Sambrook and Russel, Cold Spring Harbor Laboratory Press, Cold Spring Harbor, N.Y., 2001; CURRENT PROTOCOLS IN MOLECULAR BIOLOGY, ed. Ausubel et al., Greene Publishing Associates and Wiley-Interscience, New York, 1988 (with periodic updates); SHORT PROTOCOLS IN MOLECULAR BIOLOGY: A COMPENDIUM OF METHODS FROM CURRENT PROTOCOLS IN MOLECULAR BIOLOGY, $5^{th}$ ed., vol. 1-2, ed. Ausubel et al., John Wiley & Sons, Inc., 2002; GENOME ANALYSIS: A LABORATORY MANUAL, vol. 1-2, ed. Green et al., Cold Spring Harbor Laboratory Press, Cold Spring Harbor, N.Y., 1997.

Methods involving plant biology techniques are described herein and are described in detail in methodology treatises such as METHODS IN PLANT MOLECULAR BIOLOGY: A LABORATORY COURSE MANUAL, ed. Maliga et al., Cold Spring Harbor Laboratory Press, Cold Spring Harbor, N.Y., 1995. Various techniques using PCR are described, e.g., in Innis et al., PCR PROTOCOLS: A GUIDE TO METHODS AND APPLICATIONS, Academic Press, San Diego, 1990 and in Dieffenbach and Dveksler, PCR PRIMER: A LABORATORY MANUAL, $2^{nd}$ ed., Cold Spring Harbor Laboratory Press, Cold Spring Harbor, N.Y., 2003. PCR-primer pairs can be derived from known sequences by known techniques such as using computer programs intended for that purpose (e.g., Primer, Version 0.5, 1991, Whitehead Institute for Biomedical Research, Cambridge, Mass.). Methods for chemical synthesis of nucleic acids are discussed, for example, in Beaucage and Caruthers, *Tetra. Letts.* 22: 1859-1862 (1981) and Matteucci and Caruthers, *J. Am. Chem. Soc.* 103: 3185 (1981).

Restriction enzyme digestions, phosphorylations, ligations and transformations were done as described in Sambrook et al., MOLECULAR CLONING: A LABORATORY MANUAL, $2^{nd}$ ed. (1989)

Cold Spring Harbor Laboratory Press. All reagents and materials used for the growth and maintenance of bacterial cells were obtained from Aldrich Chemicals (Milwaukee, Wis.), DIFCO Laboratories (Detroit, Mich.), Invitrogen (Gaithersburg, Md.), or Sigma Chemical Company (St. Louis, Mo.) unless otherwise specified.

The term "expression" is used here to denote the production of the protein product encoded by a gene. "Overexpression" refers to the production of a gene product in transgenic organisms that exceeds levels of production in normal or non-transgenic organisms. As in conventional in the art, nucleotide sequences are denoted by italicized font (SAMdc), whereas polypeptide sequences are not italicized (SAMdc).

I. Reducing Insoluble Lignin Content by Overexpressing SAMdc

In one aspect, the present invention provides genetic engineering methodology and constructs for reducing lignin content in plants, particularly wood tree species, by overexpressing a polynucleotide sequence encoding SAM decarboxylase (SAMdc; EC. number 4.1.1.50) in a xylem-prefered manner. SAM is converted to decarboxylated SAM (dSAM), a precursor in the polyamine biosynthetic pathway, by the action of SAM decarboxylase (SAMdc; EC. number 4.1.1.50). Malmberg et al., *Crit. Rev. Plant Sci.* 17: 199-224 (1998). Therefore, and as described below, one way to reduce SAM levels in a plant cell and hence its lignin content is by overexpressing a SAMdc encoding gene in lignin-synthesizing tissues. Vascular tissues, which are the major lignin deposition sites in angiosperms, have low SAMdc gene expression levels, leading to the assumption that specific and localized SAMdc gene overexpression in these tissues would affect the local concentrations of SAM and thus impair lignin biosynthesis and deposition rates.

II. Increasing Wood Density by Overexpressing SAMdc

The present invention provides methodology and constructs for increasing wood density. Wood is essentially a matrix of cell walls and cellular air spaces from secondary xylem. Megraw, Wood quality factors in loblolly pine, *Tappi Press*, Atlanta, p. 88 (1985). In this sense, wood density is determined by the cell wall thickness, the cross-sectional area of the lumen of the vessels, and the number of the vessels involved in water transport through the stem. Roderick and Berry, *New Phytol.* 149: 473 (2001); Preston et al., *New Phytologist.* 170: 807-18 (2006). It has been shown in *Eucalyptus* and other angiosperm species that wood density negatively correlates with hydraulic conductivity and the cross-sectional area of the vessels. Thomasa et al., *Forest Ecology and Management* 193: 157-65 (2004); Preston et al., *New Phytologist,* 170: 807-18 (2006).

The influence of vessels on wood density can be decomposed into two components, vessel area and vessel density. "Vessel area" refers to the transverse lumen area of individual vessels. "Vessel density" refers to the number of vessels per transverse area. Vessel lumen area strongly affects the capacity of wood to conduct water. Zimmermann, XYLEM STRUCTURE AND THE ASCENT OF SAP. Berlin, Germany: Springer-Verlag. (1983). Wider vessels are generally more vulnerable to cavitation as stems freeze and thaw, particularly when xylem water is under tension. Davis et al., *American J. Botany* 86: 1367-72 (1999). By contrast, the number of vessels in a given transverse area should have a relatively small effect on sapwood conductance. These component traits, vessel area and vessel density, contribute to wood density by affecting the amount of lumen space in the wood.

III. Concurrently Reducing Lignin and Increasing Wood Density by Overexpressing SAMdc The present invention provides methodology and constructs for concurrently reducing lignin and increasing wood density in a plant, particularly a woody tree. Pursuant to this aspect of the invention, a nucleic acid sequence comprising a xylem-preferred promoter operably linked to a SAMdc encoding sequence is introduced into a plant and transgenic plants are selected that have reduced lignin content and increased wood density.

SAMdc Nucleotide and Polypeptide Sequences

Illustrative SAMdc sequences include but are not limited to the sequences set forth in SEQ ID NO: 1, 3, 5, 7, 9, 11, 13, 15, 17, 19, 24, and 26, respectively, as well as nucleic acid molecules comprised of variants of SEQ ID NO: 1, 3, 5, 7, 9, 11, 13, 15, 17, 19, 24, and 26, with one or more bases deleted, substituted, inserted, or added, which variant codes for a polypeptide with SAMdc enzyme activity.

A "variant" is a nucleotide or amino acid sequence that deviates from the standard, or given, nucleotide or amino acid sequence of a particular gene or protein. The terms "isoform," "isotype," and "analog" also refer to "variant" forms of a nucleotide or an amino acid sequence. An amino acid sequence that is altered by the addition, removal, or substitution of one or more amino acids, or a change in nucleotide sequence, may be considered a "variant" sequence. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, Md.) software. "Variant" may also refer to a "shuffled gene" such as those described in Maxygen-assigned patents.

Exemplary SAMdc polypeptide sequences include but are not limited to the sequences set forth in SEQ ID NO: 2, 4, 6, 8, 10, 12, 14, 16, 18, 25, and 27, as well as polypeptide sequences having one or more amino acids substituted, deleted, inserted, or added yet retain SAMdc enzyme activity. Additionally, multiple forms of SAMdc may exist, which may be due to post-translational modification of a gene product, or to multiple forms of the respective SAMdc genes. Sequences that have such modifications and that code for a SAMdc enzyme are included within the scope of the present invention.

Accordingly, "SAMdc nucleotide sequence" refers to a polynucleotide sequence encoding a polypeptide with SAMdc enzyme activity. In this description, moreover, the phrase "SAMdc enzyme activity" connotes a protein that catalyzes the conversion of SAM into decarboxylated SAM, and that can be assayed by measuring the release of $^{14}CO_2$ from S-adenosyl-L-[$^{14}C$] as described, for example, in Hanfrey et al., *J. Biol. Chem.* 277: 44121-129 (2002). SAMdc protein levels in ground plant tissue can be quantified, using conventional protein assays, such as the Bradford method, *Anal. Biochem.* 72: 248-54 (1976), and enzyme activity typically is expressed as nanomole of $CO_2$/h/mg of protein.

Sequence Analysis

Included in the category of "variant" sequences are sequences that hybridize to a reference SAMdc sequence. For the purpose of the invention, two sequences hybridize when they form a double-stranded complex in a hybridization solution of 6×SSC, 0.5% SDS, 5×Denhardt's solution and 100 μg of non-specific carrier DNA. See Ausubel et al., supra, at section 2.9, supplement 27 (1994). Sequences may hybridize at "moderate stringency," which is defined as a temperature of 60° C. in a hybridization solution of 6×SSC, 0.5% SDS, 5×Denhardt's solution and 100 µg of non-specific carrier DNA. For "high stringency" hybridization, the temperature is increased to 68° C. Following the moderate stringency hybridization reaction, the nucleotides are washed in a solution of 2×SSC plus 0.05% SDS for five times at room temperature, with subsequent washes with 0.1×SSC plus 0.1% SDS at 60° C. for 1 hour. For high stringency, the wash temperature is increased to 68° C. One with ordinary skill in the art can readily select such conditions by varying the temperature during the hybridization reaction and washing process, the salt concentration during the hybridization reaction and washing process, and so forth. For the purpose of the invention, hybridized nucleotides are those that are detected using 1 ng of a radiolabeled probe having a specific radioactivity of 10,000 cpm/ng, where the hybridized nucleotides are clearly visible following exposure to X-ray film at −70° C. for no more than 72 hours.

The present application is directed to such nucleic acid molecules that are at least 60%, 65%, 70%, 75%, 80%, 85%, 90%, 95%, 96%, 97%, 98%, 99% or 100% identical to a nucleic acid sequence described in any of SEQ ID NOs: 1, 3, 5, 7, 9, 11, 13, 15, 17, 19, 24, and 26. Preferred are nucleic acid molecules which are at least 95%, 96%, 97%, 98%, 99% or 100% identical to the nucleic acid sequence shown in any of SEQ ID NOs: 1, 3, 5, 7, 9, 11, 13, 15, 17, 19, 24, and 26. Differences between two nucleic acid sequences may occur at the 5' or 3' terminal positions of the reference nucleotide sequence or anywhere between those terminal positions, interspersed either individually among nucleotides in the reference sequence or in one or more contiguous groups within the reference sequence.

As a practical matter, stating whether any particular nucleic acid molecule is at least 95%, 96%, 97%, 98% or 99% identical to a reference nucleotide sequence implicates a comparison made between two molecules, using algorithms known in the art and can be determined conventionally using publicly available computer programs such as the BLASTN algorithm. See Altschul et al., *Nucleic Acids Res.* 25: 3389-402 (1997).

Nucleic Acid Constructs

In accordance with an aspect of the invention, a sequence that increases wood density and reduces lignin content is incorporated into a nucleic acid construct that is suitable for introduction into a plant or cell. Thus, such a nucleic acid construct can be used to overexpress SAMdc in a plant or plant cell.

The wood density and lignin content and composition of plant parts may be modified by introducing a nucleic acid construct according to the invention. The invention also provides plant cells containing such constructs; plants derived therefrom having modified SAMdc gene expression; and progeny of such plants.

Nucleic acid constructs according to the invention may comprise a base sequence of a minimum length to generate a mRNA and consequently a polypeptide retaining SAMdc enzymatic activity. For convenience, it will generally be found suitable to use sequences between about 100 and about 1000 bases in length but there is no theoretical upper limit to the base sequence length. The preparation of such constructs is described in more detail below.

As a source of the nucleic acid sequence for transcription, a suitable cDNA or genomic DNA or synthetic polynucleotide may be used. Methods for the isolation of suitable SAMdc sequences are described, supra. Sequences coding for the whole, or substantially the whole, of the enzyme may thus be obtained. Suitable lengths of this DNA sequence may be cut out for use by means of restriction enzymes. When using genomic DNA as the source of a partial base sequence for transcription, it is possible to use either intron or exon regions or a combination of both.

To obtain constructs suitable for modifying expression of SAMdc in plant cells, the cDNA sequence as found in the enzyme cDNA or the gene sequence as found in the chromosome of the plant may be used. Recombinant nucleic acid constructs may be made using standard techniques. For example, the nucleic acid sequence for transcription may be obtained by treating a vector containing said sequence with restriction enzymes to cut out the appropriate segment. The nucleic acid sequence for transcription may also be generated by annealing and ligating synthetic oligonucleotides or by using synthetic oligonucleotides in a polymerase chain reaction (PCR) to give suitable restriction sites at each end. The nucleic acid sequence then is cloned into a vector containing suitable regulatory elements, such as upstream promoter and downstream terminator sequences.

An important aspect of the present invention is the use of nucleic acid constructs wherein a SAMdc-encoding sequence is operably linked to one or more regulatory sequences, which drive expression of the SAMdc-encoding sequence in certain cell types, organs, or tissues without unduly affecting normal development or plant physiology.

"Promoter" connotes a region of DNA upstream from the start of transcription that is involved in recognition and binding of RNA polymerase and other proteins to initiate transcription. A "constitutive promoter" is one that is active throughout the life of the plant and under most environmental conditions. Tissue-specific, tissue-preferred, cell type-specific, and inducible promoters constitute the class of "non-constitutive promoters." "Operably linked" refers to a functional linkage between a promoter and a second sequence, where the promoter sequence initiates and mediates transcription of the DNA sequence corresponding to the second sequence. In general, "operably linked" means that the nucleic acid sequences being linked are contiguous.

Promoters useful for expression of a nucleic acid sequence introduced into a cell to increase expression of SAMdc may be constitutive promoters, such as the cauliflower mosaic virus (CaMV) 35S promoter, or tissue-specific, tissue-preferred, cell type-specific, and inducible promoters. For example, by using vascular system-specific, xylem-specific, or xylem-preferred promoters, one can modify SAMdc activity specifically in many tissues such as vascular tissues, especially xylem. The use of a constitutive promoter in general affects enzyme levels and functions in all parts of the plant, while use of a tissue-preferred promoter permits targeting of the modified gene expression to specific plant parts, leading to a more controllable phenotypes.

Thus, in using the invention, it may be found convenient to use a promoter that will give expression during xylem development and/or xylem lignification, whereby the SAMdc enzyme would only be overproduced in the organ(s) or tissue(s) or cell type(s) in which its action is required. As used herein, "xylem-preferred promoter" means that the nucleic acid molecules of the current invention are more active in the xylem than in any other plant tissue. Xylem-preferred promoters that could be used include, but are not limited to, the xylem-preferred tubulin (TUB) gene promoter, the xylem-preferred lipid transfer protein (LTP) gene promoter and the xylem-preferred coumarate-4-hydroxylase (C4H) gene promoter.

The vectors of the invention may also contain termination sequences, which are positioned downstream of the nucleic acid molecules of the invention, such that transcription of mRNA is terminated, and polyA sequences added. Exemplary of such terminators are the cauliflower mosaic virus (CaMV) 35S terminator and the nopaline synthase gene (Tnos) terminator. The expression vector also may contain enhancers, start codons, splicing signal sequences, and targeting sequences.

Expression vectors of the invention may also contain a selection marker by which transformed cells can be identified in culture. The marker may be associated with the heterologous nucleic acid molecule, i.e., the gene operably linked to a promoter. As used herein, the term "marker" refers to a gene encoding a trait or a phenotype that permits the selection of, or the screening for, a plant or cell containing the marker. In plants, for example, the marker gene will encode antibiotic or herbicide resistance. This allows for selection of transformed cells from among cells that are not transformed or transfected.

Examples of suitable selectable markers include adenosine deaminase, dihydrofolate reductase, hygromycin-B-phosphotransferase, thymidne kinase, xanthine-guanine phosphoribosyltransferase, glyphosate and glufosinate resistance, and amino-glycoside 3'-O-phosphotranserase (kanamycin, neomycin and G418 resistance). These markers may include resistance to G418, hygromycin, bleomycin, kanamycin, and gentamicin. The construct may also contain the selectable marker gene Bar that confers resistance to herbicidal phosphinothricin analogs like ammonium gluphosinate. Thompson et al., *EMBO J.* 9: 2519-23 (1987). Other suitable selection markers are known as well.

Visible markers such as green florescent protein (GFP) may be used. Methods for identifying or selecting transformed plants based on the control of cell division have also been described. See WO 2000/052168 and WO 2001/059086.

Replication sequences, of bacterial or viral origin, may also be included to allow the vector to be cloned in a bacterial or phage host. Preferably, a broad host range prokaryotic origin of replication is used. A selectable marker for bacteria may be included to allow selection of bacterial cells bearing the desired construct. Suitable prokaryotic selectable markers also include resistance to antibiotics such as kanamycin or tetracycline.

Other nucleic acid sequences encoding additional functions may also be present in the vector, as is known in the art. For instance, when *Agrobacterium* is the host, T-DNA sequences may be included to facilitate the subsequent transfer to and incorporation into plant chromosomes.

Plants for Genetic Engineering

The present invention comprehends the genetic manipulation of angiosperm and gymnosperm plants for increasing wood density and decreasing insoluble lignin content via overexpressing a polynucleotide sequence that encodes SAMdc. In this regard, angiosperm refers to vascular plants having seeds enclosed in an ovary and are divided into dicotyledonous and monocotyledonous plants. Gymnosperm refers to a seed plant that bears seed without ovaries. Illustrative gymnosperms include conifers, cycads, ginkgos, and ephedras.

Genetically engineered (GE) encompasses any methodology for introducing a nucleic acid or specific mutation into a host organism. For example, a *Eucalyptus* plant is genetically engineered when it is transformed with a polynucleotide sequence that increases expression of a gene, such as SAMdc, and thereby increases wood density. In contrast, a *Eucalyptus* plant that is not transformed with a polynucleotide sequence is a control plant and is referred to as a "non-transformed" plant.

In the present context, the "genetically engineered" category includes "transgenic" plants and cells (see definition, infra), as well as plants and cells produced by means of targeted mutagenesis effected, for example, through the use of chimeric RNA/DNA oligonucleotides, as described by Beetham et al., *Proc. Natl. Acad. Sci. USA* 96: 8774-78 (1999), and Zhu et al., loc. cit. at 8768-73, or so-called "recombinagenic olionucleobases," as described in PCT application WO 03/013226. Likewise, a genetically engineered plant or cell may be produced by the introduction of a modified virus, which, in turn, causes a genetic modification in the host, with results similar to those produced in a transgenic plant, as described herein. See, e.g., U.S. Pat. No. 4,407,956. Additionally, a genetically engineered plant or cell may be the product of any native approach (i.e., involving no foreign nucleotide sequences), implemented by introducing only nucleic acid sequences derived from the host species or from a sexually compatible species. See, e.g., U.S. published application No. 2004/0107455.

"Plant" is a term that encompasses whole plants, plant organs (e.g. leaves, stems, roots, etc.), seeds, differentiated or undifferentiated plant cells, and progeny of the same. Plant material includes, without limitation, seeds suspension cultures, embryos, meristematic regions, callus tissues, leaves, roots, shoots, stems, fruit, gametophytes, sporophytes, pollen, and microspores. The class of plants which can be used in the present invention is generally as broad as the class of higher plants amenable to genetic engineering techniques, including angiosperms, both monocotyledonous and dicotyledonous plants, as well as gymnosperms.

While any plant may be used, the present invention contemplates plants used in the pulp and paper industry. Preferably, the plants are woody trees, including, but not limited to, *Eucalyptus* species such as *E. alba, E. albens, E. amygdalina, E. aromaphloia, E. baileyana, E. balladoniensis, E. bicostata, E. botryoides, E. brachyandra, E. brassiana, E. brevistylis, E. brockwayi, E. camaldulensis, E. ceracea, E. cloeziana, E. coccifera, E. cordata, E. cornuta, E. corticosa, E. crebra, E. croajingolensis, E. curtisii, E. dalrympleana, E. deglupta, E. delegatensis, E. delicata, E. diversicolor, E. diversifolia, E. dives, E. dolichocarpa, E. dundasii, E. dunnii, E. elata, E. erythrocorys, E. erythrophloia, E. eudesmoides, E. falcata, E. gamophylla, E. glaucina, E. globulus, E. globulus subsp. bicostata, E. globulus subsp. globulus, E. gongylocarpa, E. grandis, E. grandis x urophylla, E. guilfoylei, E. gunnii, E. hallii, E. houseana, E. jacksonii, E. lansdowneana, E. latisinensis, E. leucophloia, E. leucoxylon, E. lockyeri, E. lucasii, E. maidenii, E. marginata, E. megacarpa, E. melliodora, E. michaeliana, E. microcorys, E. microtheca, E. muelleriana, E. nitens, E. nitida, E. obliqua, E. obtusiflora, E. occidentalis, E. optima, E. ovata, E. pachyphylla, E. pauciflora, E. pellita, E. perriniana, E. petiolaris, E. pilularis, E. piperita, E. platyphylla, E. polyanthemos, E. populnea, E. preissiana, E. pseudoglobulus, E. pulchella, E. radiata, E. radiata subsp. radiata, E. regnans, E. risdonii, E. robertsonii, E. rodwayi, E. rubida, E. rubiginosa, E. saligna, E. salmonophloia, E. scoparia, E. sieberi, E. spathulata, E. staeri, E. stoatei, E. tenuipes, E. tenuiramis, E. tereticornis, E. tetragona, E. tetrodonta, E. tindaliae, E. torquata, E. umbra, E. urophylla, E. vernicosa, E. viminalis, E. wandoo, E. wetarensis, E. willisii, E. willisii subsp. falciformis, E. willisii subsp. willisii*, and *E. woodwardii*.

The invention also contemplates Populus species such as *P. alba, P. alba x P. grandidentata, P. alba x P. tremula, P. alba x P. tremula var. glandulosa, P. alba x P. tremuloides, P. balsamifera, P. balsamifera subsp. trichocarpa, P. balsamifera subsp. trichocarpa x P. deltoides, P. ciliata, P. deltoides, P. euphratica, P. euramericana, P. kitakamiensis, P. lasiocarpa, P. laurifolia, P. maximowiczii, P. maximowiczii x P.* balsamifera subsp. *trichocarpa*, *P. nigra*, *P. sieboldii* x *P. grandidentata*, *P. suaveolens*, *P. szechuanica*, *P. tomentosa*, *P. tremula*, *P. tremula* x *P. tremuloides*, *P. tremuloides*, *P. wilsonii*, *P. canadensis*, *P. yunnanensis* and Conifers as, for example, loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Other plants that may be modified by the process of the invention include all flowering plants. It is understood that the word "plant" includes any plant or plant material used in the pulp and paper industry.

Methods for Genetic Engineering

For the purposes of this description, a SAMdc sequence operably linked to a promoter may be introduced into a plant or cell. For example, an illustrative vector may comprise a SAMdc sequence operably linked to a xylem-preferred promoter.

Plant Transformation

"Transgenic plant" refers to a plant that comprises a nucleic acid sequence that also is present per se in another organism or species or that is optimized, relative to host codon usage, from another organism or species. Both monocotyledonous and dicotyledonous angiosperm or gymnosperm plant cells may be transformed in various ways known to the art. For example, see Klein et al., *Biotechnology* 4: 583-590 (1993); Bechtold et al., *C. R. Acad. Sci. Paris* 316: 1194-1199 (1993); Bent et al., *Mol. Gen. Genet.* 204: 383-396 (1986); Paszowski et al., *EMBO J.* 3: 2717-2722 (1984); Sagi et al., *Plant Cell Rep.* 13: 262-266 (1994). *Agrobacterium* species such as *A. tumefaciens* and *A. rhizogenes* can be used, for example, in accordance with Nagel et al., *Microbiol Lett* 67: 325 (1990). Additionally, plants may be transformed by *Rhizobium*, *Sinorhizobium* or *Mesorhizobium* transformation. Broothaerts et al., *Nature* 433: 629-633 (2005).

For example, *Agrobacterium* may be transformed with a plant expression vector via, e.g., electroporation, after which the *Agrobacterium* is introduced to plant cells via, e.g., the well known leaf-disk method. Additional methods for accomplishing this include, but are not limited to, electroporation, particle gun bombardment, calcium phosphate precipitation, and polyethylene glycol fusion, transfer into germinating pollen grains, direct transformation, Lorz et al., *Mol. Genet.* 199: 179-182 (1985), and other methods known to the art. If a selection marker, such as kanamycin resistance, is employed, it makes it easier to determine which cells have been successfully transformed. Marker genes may be included within pairs of recombination sites recognized by specific recombinases such as cre or flp to facilitate removal of the marker after selection. See U.S. published application No. 2004/0143874.

Transgenic plants without marker genes may be produced using a second plasmid comprising a nucleic acid encoding the marker, distinct from a first plasmid that comprises a SAMdc sequence. The first and second plasmids or portions thereof are introduced into the same plant cell, such that the selectable marker gene that is transiently expressed, transformed plant cells are identified, and transformed plants are obtained in which the SAMdc sequence is stably integrated into the genome and the selectable marker gene is not stably integrated. See U.S. published application No. 2003/0221213.

The *Agrobacterium* transformation methods discussed above are known to be useful for transforming dicots. Additionally, de la Pena et al., *Nature* 325: 274-276 (1987), Rhodes et al., *Science* 240: 204-207 (1988), and Shimamato et al., *Nature* 328: 274-276 (1989) have transformed cereal monocots using *Agrobacterium*. Also see Bechtold et al., *C.R. Acad. Sci. Paris* 316 (1994), illustrating vacuum infiltration for *Agrobacterium*-mediated transformation.

Plant cells may be transformed with nucleic acid constructs of the present invention without the use of a selectable or visible marker and transgenic organisms may be identified by detecting the presence of the introduced construct. The presence of a protein, polypeptide, or nucleic acid molecule in a particular cell can be measured to determine if, for example, a cell has been successfully transformed or transfected. For example, and as routine in the art, the presence of the introduced construct can be detected by PCR or other suitable methods for detecting a specific nucleic acid or polypeptide sequence. Additionally, transformed cells may be identified by recognizing differences in the growth rate or a morphological feature of a transformed cell compared to the growth rate or a morphological feature of a non-transformed cell that is cultured under similar conditions. See WO 2004/076625.

Methods of regenerating a transgenic plant from a transformed cell or culture vary according to the plant species but are based on known methodology. For example, methods for regenerating of transgenic *Nicotiana* and *Eucalyptus* plants are well-known.

Selection and Analysis of Genetically Engineered Plants

Genetically engineered plants of the invention are selected that have increased expression of SAMdc relative to a control, non-transgenic plant of the same species. Additionally, the inventive genetically engineered plants may have increased wood density and decreased lignin content. For example, an inventive transgenic plant may have a phenotype characterized by (1) an ability of the whole plant to accumulate less compounds derived from monolignols; (2) an altered vessel number and vessel lumen area such that wood density is increased because vessel number and vessel area negatively correlate with wood density; and (3) an altered lignin content relative to an untransformed host plant.

The phrase "increased wood density" refers to a quantitative increase of wood density relative to a wild-type or control plant of the same species. The wood density of the engineered plant of the invention can be increased from 5% to about 70%, preferably from 10% to about 60%, even more preferably from 15% to about 50% of the wood density of a wild type plant. A most preferred embodiment of the engineered plant of the invention has a wood density of about 20% to about 40% of a wild type plant. Wood density is determined by methods known in the art, such as those described in Chave et al., *Ecol. Appl.* 16:2356-2367 (2006). For example, wood density may be determined by collecting wood samples at breast height and calculating oven dry weight (kg)/oven dry volume ($m^3$).

"Reduced insoluble lignin content" and "decreased insoluble lignin content" refer to a quantitative reduction in the amount of insoluble lignin in the plant when compared to the amount of insoluble lignin in a wild-type or control plant. The insoluble lignin content in the engineered plant of the invention can be reduced to levels of about 5% to about 90%, preferably about 10% to about 75%, even more preferably about 15% to about 65% of the lignin content of a wild-type plant. A most preferred embodiment of the plant of the invention has a lignin content of about 10% to about 60% of a wild-type lignin content. A quantitative reduction of lignin content can be assayed by several methods, as for examples the Klason lignin assay, Kirk et al., *Method in Enzymol.* 161: 87-101 (1988), or acetyl bromide assay of lignin. Iiyama et al., *Wood Sci. Technol.* 22: 271-80 (1988).

The phrase "altered lignin composition" refers to quantitative alteration in the relative amounts of syringyl and guaiacyl lignin units in the engineered plant compared to a wild-type or control plant. Preferably, a plant having altered syringyl and guaiacyl lignin composition exhibits a reduced guaiacyl lignin content compared to the guaiacyl lignin content of a wild-type plant; more preferably, it exhibits an increased pairwise syringyl lignin/guaiacyl lignin ratio, i.e., "S/G ratio," compared to the S/G ratio of a wild-type plant. Plants of the present invention can be assayed to determine their S/G ratios in comparison to the ratio of a wild-type plant using several different assay methods, including those described by Rolando et al., METHODS IN LIGNIN CHEMISTRY, Springer, New York (1992). Plants of the present invention exhibit an overall decrease in lignin content when compared to a wild-type or control plant, while exhibiting an increased S/G ratio.

Specific examples are presented below of methods for obtaining SAMdc encoding genes as well as methods for introducing a SAMdc gene to produce plant transformants. They are meant to illustrate and not to limit the present invention.

Example 1

Isolation of the Tobacco cDNA Encoding SAMdc Enzyme (a) Preparation of mRNA From Tobacco Leaves and cDNA Synthesis RNA was extracted from leaf tissue of *Nicotiana tabacum* using Trizol reagent (Invitrogen). A cDNA pool was prepared from the isolated total RNA using a commercially available cDNA Superscript II Amplification Kit (Invitrogen) or the like. The cDNA pool can then be used in RT-PCR experiments in which the isolated total RNA is used as template, and Superscript II reverse transcriptase (Invitrogen) and oligo (dT) primer are used to synthesize the first-strand cDNA and double-stranded cDNA is obtained by the subsequent polymerase reaction, using gene-specific primers.

(b) Design of PCR Primers

A DNA sequence coding for SAMdc from *Nicotiana tabacum* has already been determined and deposited in the GenBank under accession number AF033100. Based on this sequence, DNA oligomers were synthesized as primers for PCR, including either the region around the first codon ATG or around the termination codon of the main ORF encoding the SAMdc enzyme.

Primers were designed to amplify the entire coding region of the SAMdc main ORF, i.e., from the ATG through the translation stop codon. The sequences of the primers are given below for the tobacco SAMdc gene:

```
SAMdc_Nt1      Length: 24      SEQ ID NO: 20
ATCCCATGGATTCGGCCTTGCCTG

SAMdc_Nt2      Length: 34      SEQ ID NO: 21
GTCTAGACTACTCCTTCTCTTCTTTCTCTTCATC
```

(c) PCR Amplification of SAMdc From *Nicotiana tabacum*

The cDNA pool obtained in (a) was used as template, and the primers designed in (b) were used for PCR. The PCR steps involved 40 cycles of 1 minute at 94° C., 1 minute at 52° C., and 2 minutes at 72° C. followed by an extra step of elongation at 72° C. for 7 minutes. The PCR products were isolated by gel electrophoresis on 1.0% agarose followed by ethidium bromide staining of the electrophoresed gel and detection of amplified bands on a UV transilluminator. The detected amplified band was verified and cut out of the agarose gel with a razor. The pieces of gel were transferred to 1.5 mL microtubes, and the DNA fragments were isolated and purified using a GFX PCR clean-up and gel band purification kit (Amersham). The recovered DNA fragments were subcloned to the pGEM-T cloning vector (Promega), transformed into *E. coli*, and then used to prepare plasmid DNA in the usual manner, which was then sequenced by the dideoxy method, Messing, *Methods in Enzymol.*, 101, 20-78 (1983), using the BigDye chemistry (Applied Biosystems), yielding the DNA sequence disclosed herein under SEQ ID NO: 1 for use according to embodiments described in this patent.

Example 2

Preparation of Transgenic *Arabidopsis* and *Nicotiana* Plants

The gene obtained in Example 1 above was introduced into a plant host to produce transgenic *Arabidopsis* and *Nicotiana* plants.

(1) Preparation of Constructs and Transformation of *Agrobacterium*

Figure 2:
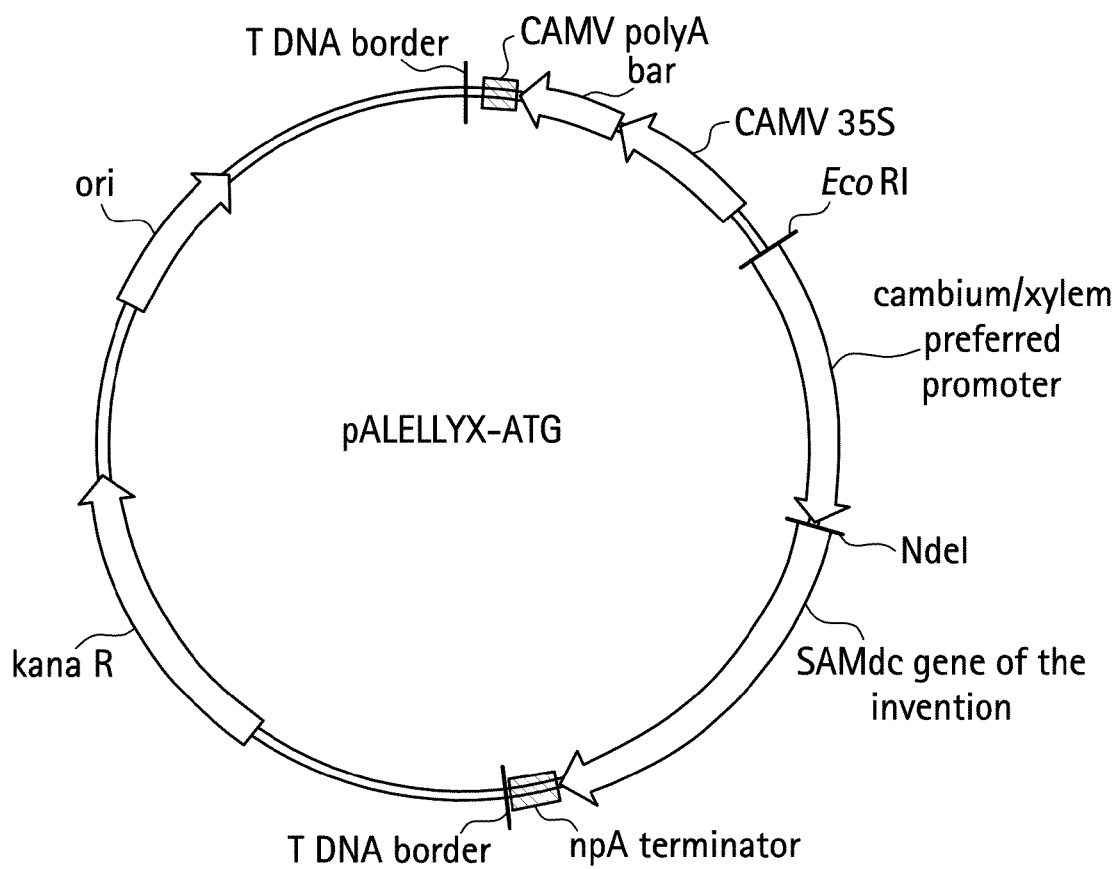
FIG. 2 schematically illustrates the plant expression plasmidial vector pALELLYX-ATG of the invention comprising a cambium/xylem preferred promoter driving the expression of a SAMdc nucleotide sequence of the invention.
Figure 3:
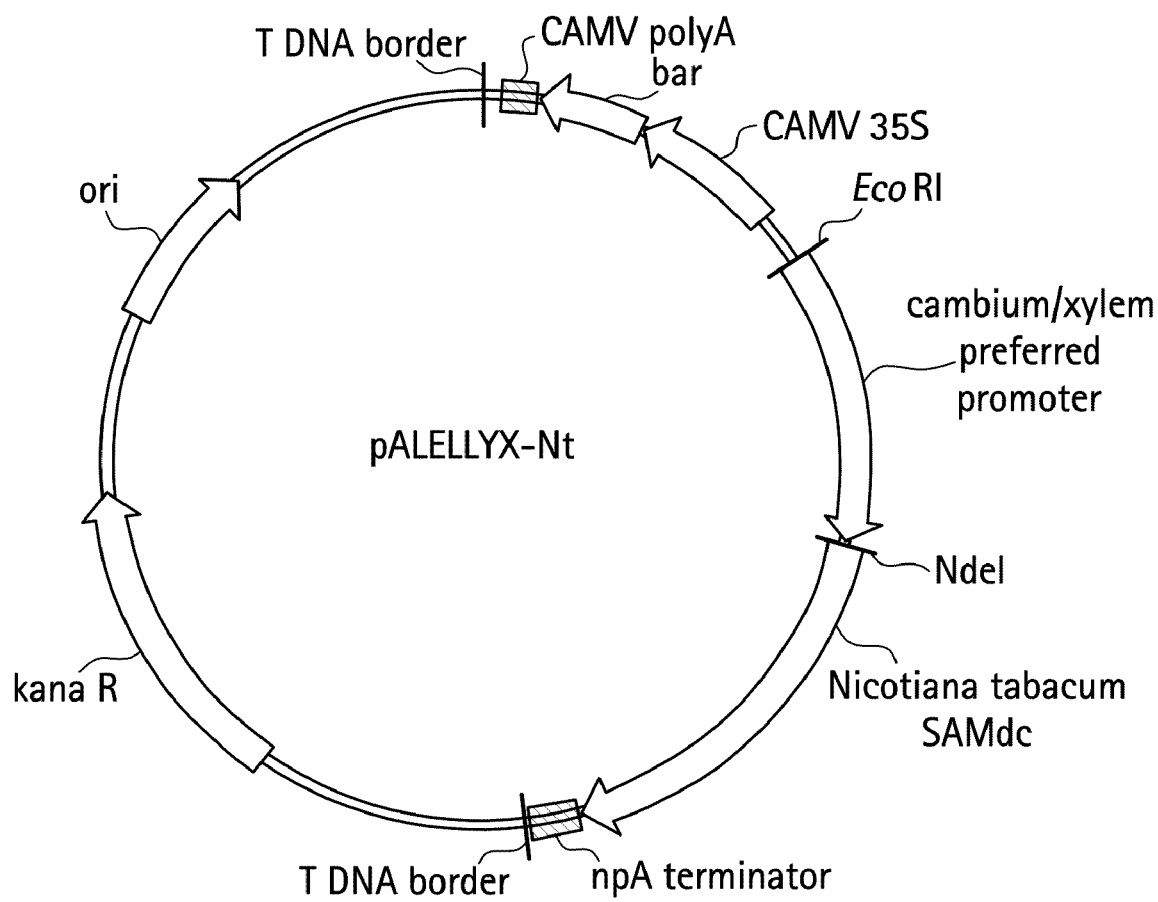
FIG. 3 schematically illustrates the plant expression plasmidial vector pALELLYX-Nt of the invention comprising a cambium/xylem preferred promoter driving the expression of a SAMdc nucleotide sequence from *Nicotiana tabacum* (tobacco).
Figure 4:
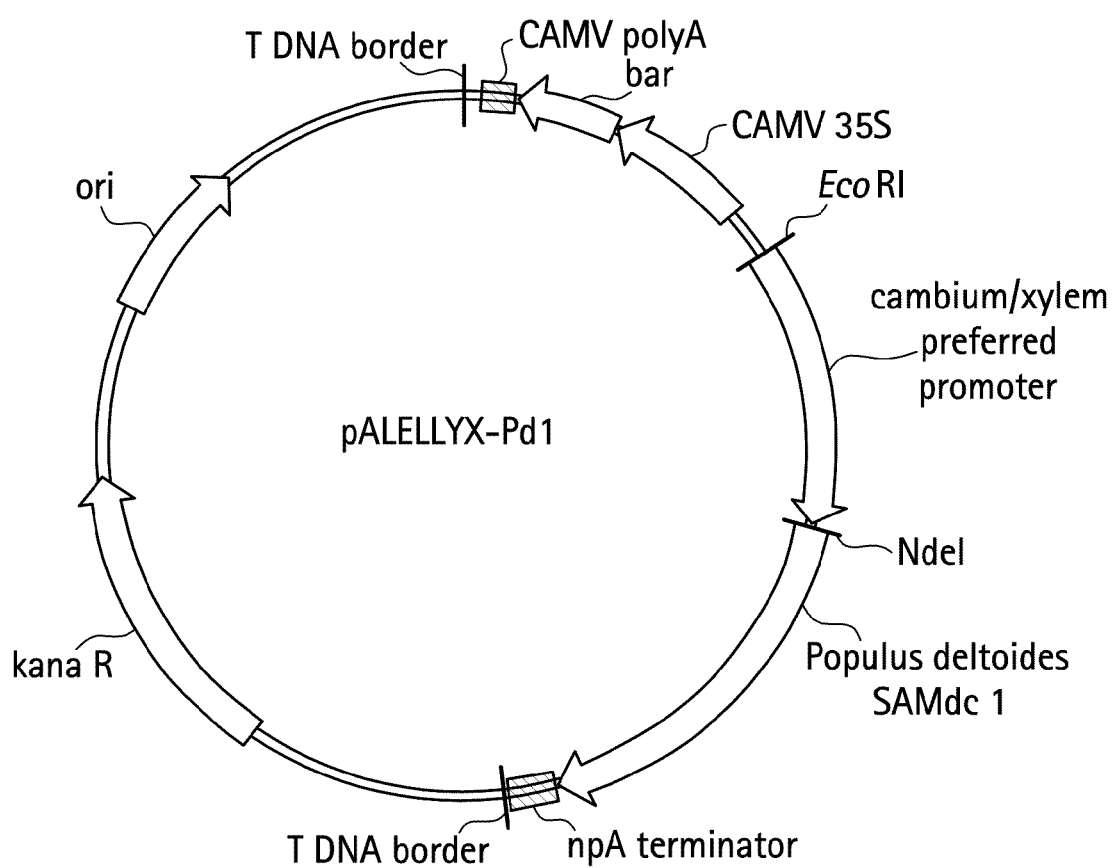
FIG. 4 schematically illustrates the plant expression plasmidial vector pALELLYX-Pd1 of the invention comprising a cambium/xylem preferred promoter driving the expression of SAMdc nucleotide sequence coding for SAMdc 1 from *Populus deltoides*.
Figure 5:
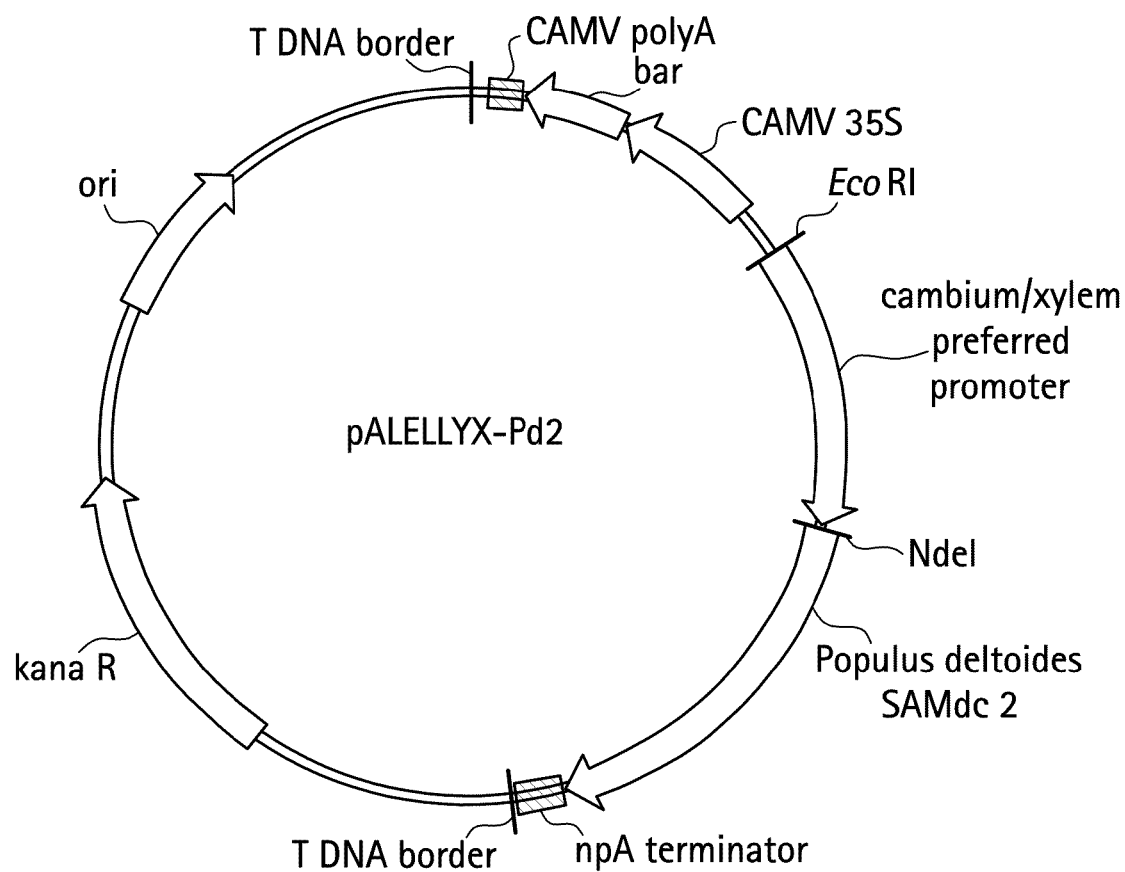
FIG. 5 schematically illustrates the plant expression plasmidial vector pALELLYX-Pd2 of the invention comprising a cambium/xylem preferred promoter driving the expression of SAMdc nucleotide sequence coding for SAMdc 2 from *Populus deltoides*.
Figure 6:
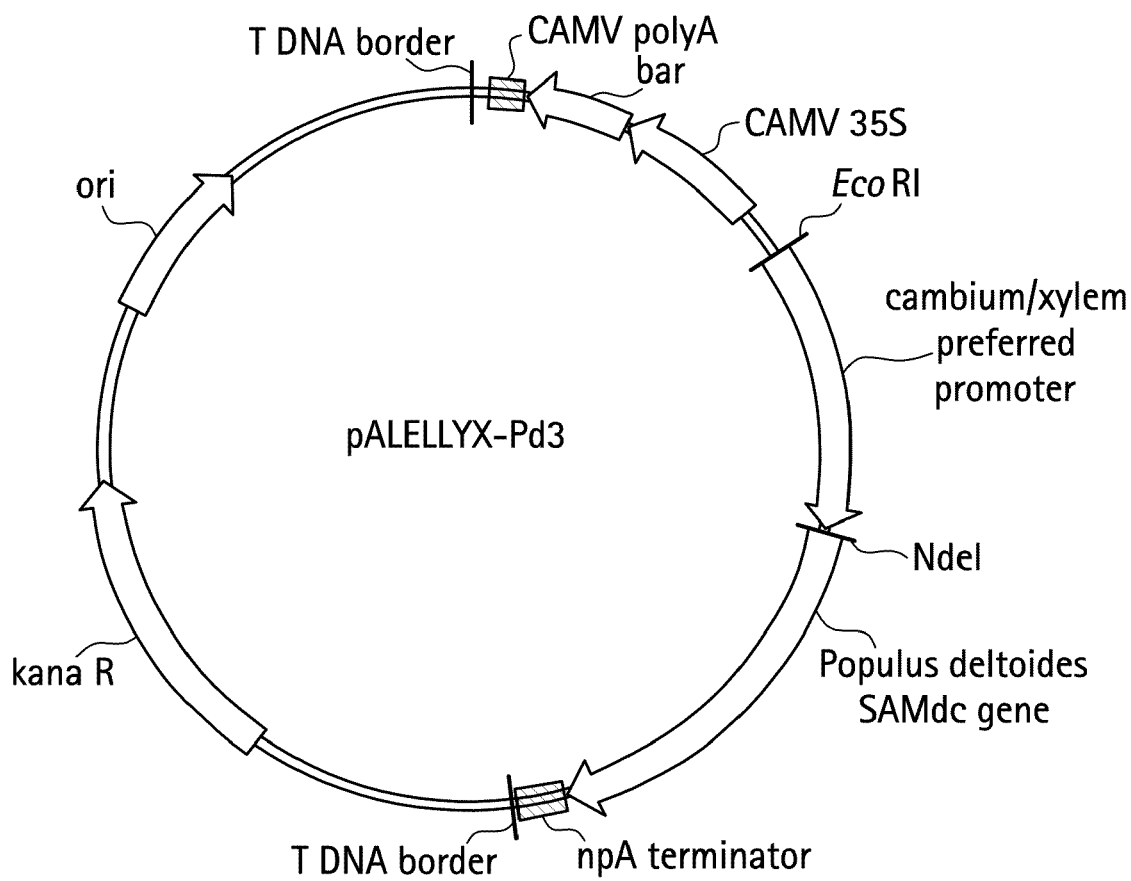
FIG. 6 schematically illustrates the plant expression plasmidial vector pALELLYX-Pd3 of the invention comprising a cambium/xylem preferred promoter upstream of a SAMdc genomic sequence from *Populus deltoides*.
Figure 7:
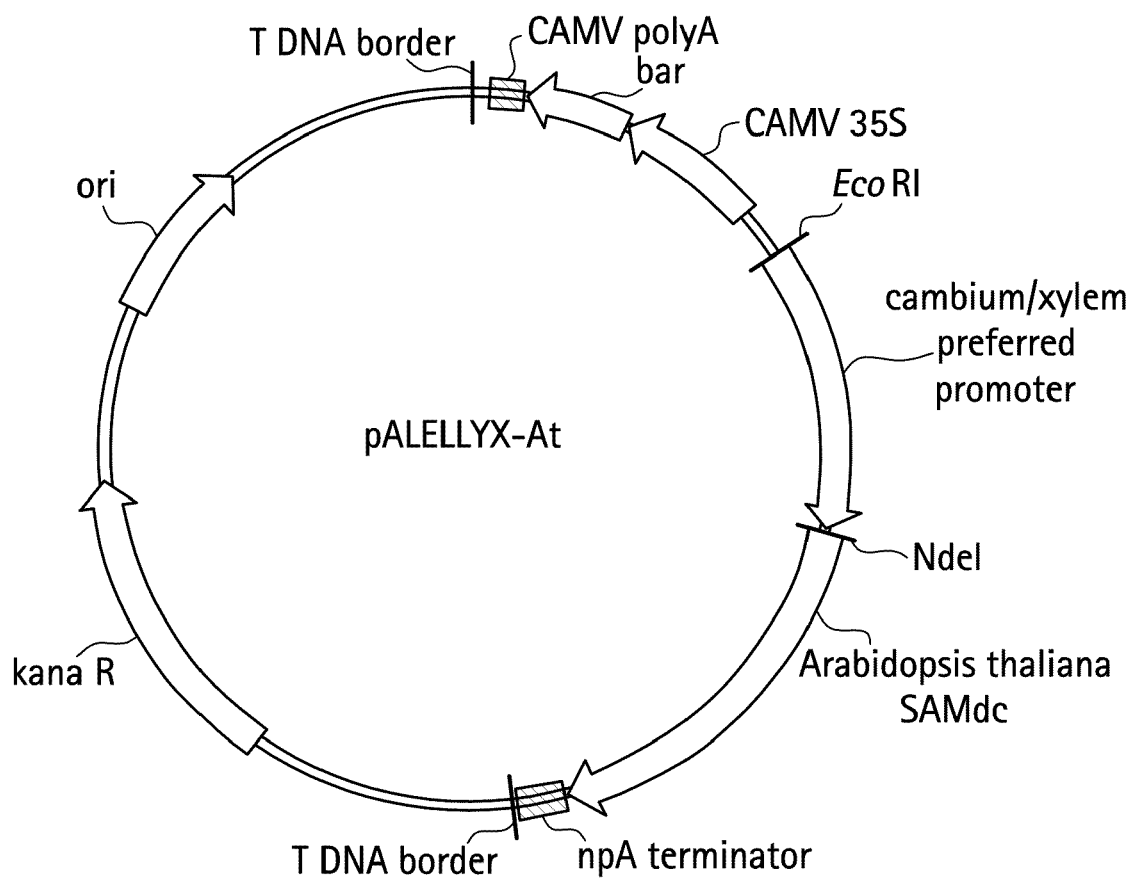
FIG. 7 schematically illustrates the plant expression plasmidial vector pALELLYX-At of the invention comprising a cambium/xylem preferred promoter driving the expression of a SAMdc nucleotide sequence from *Arabidopsis thaliana* (thale cress).
Figure 8:
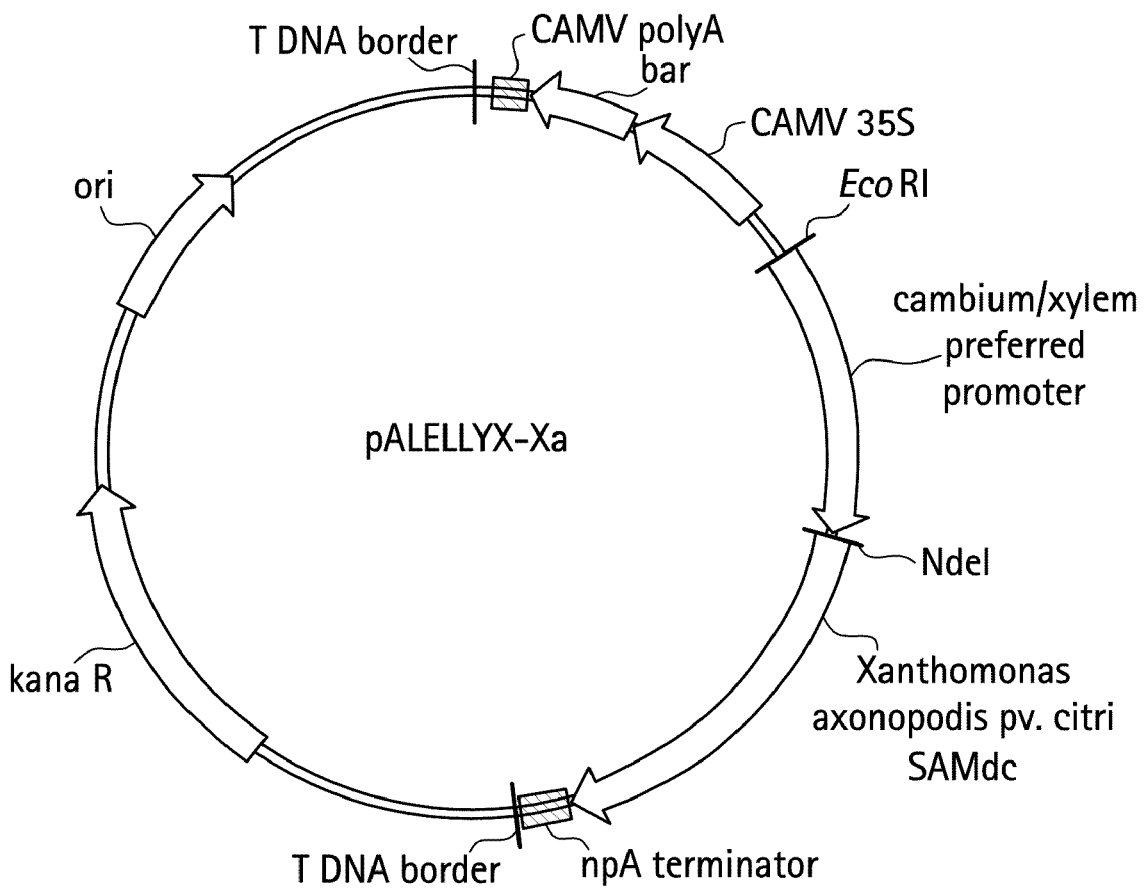
FIG. 8 schematically illustrates the plant expression plasmidial vector pALELLYX-Xa of the invention comprising a cambium/xylem preferred promoter upstream of an open reading frame coding for SAMdc from the plant pathogen *Xanthomonas axonopodis*.
Figure 9:
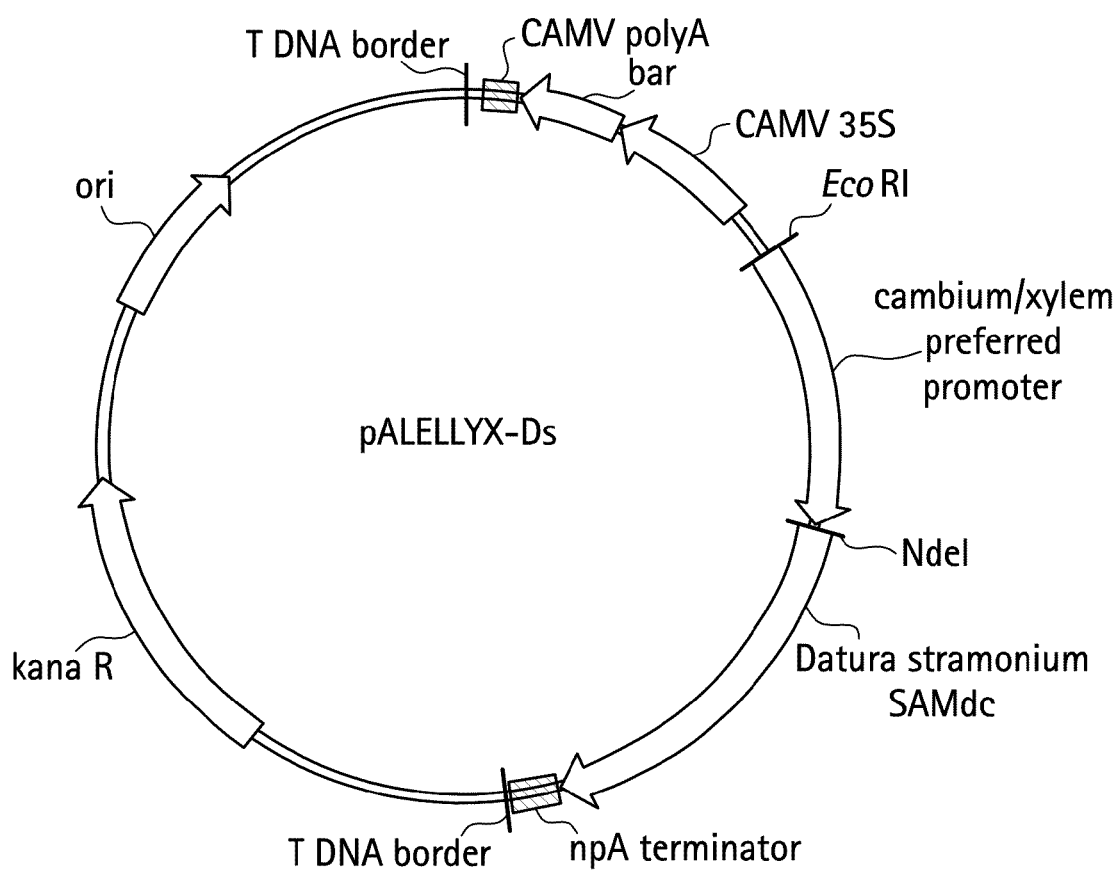
FIG. 9 schematically illustrates the plant expression plasmidial vector pALELLYX-Ds of the invention comprising a cambium/xylem preferred promoter driving the expression of a SAMdc nucleotide sequence from *Datura stramonium*.
Figure 10:
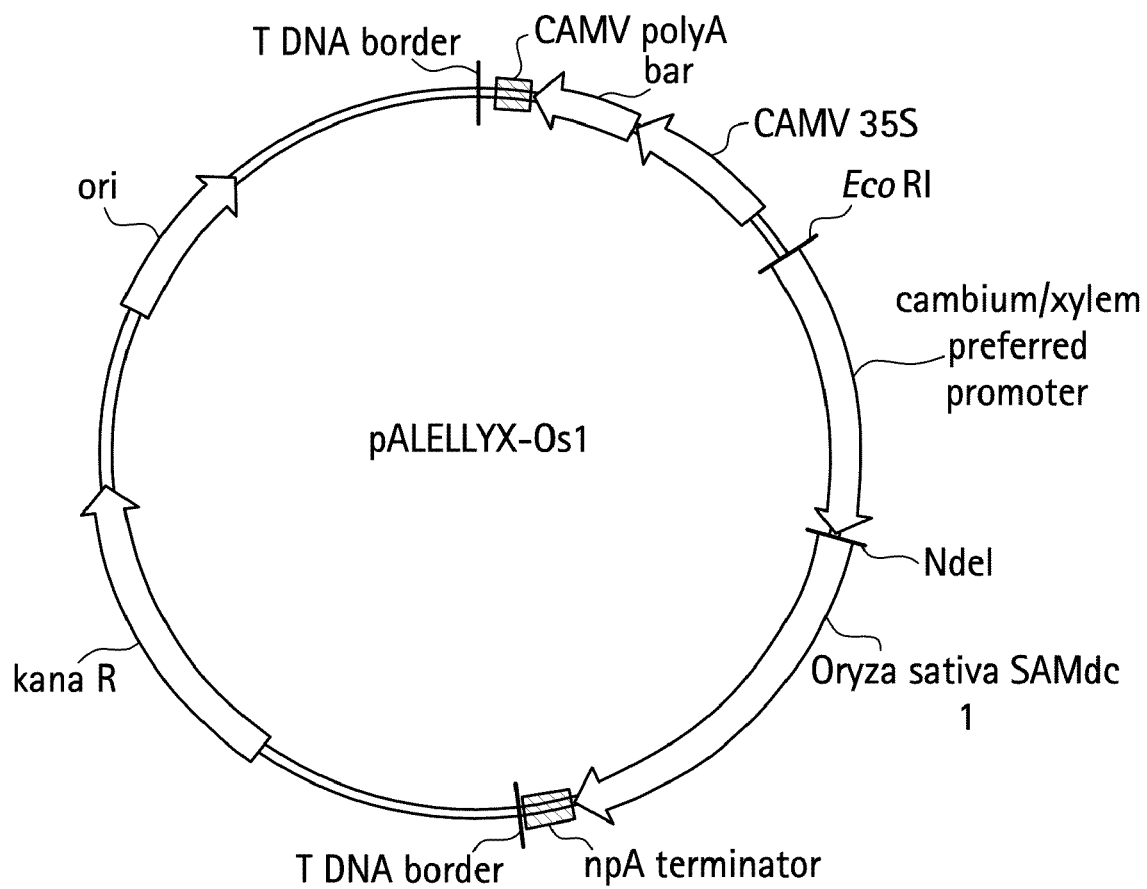
FIG. 10 schematically illustrates the plant expression plasmidial vector pALELLYX-Os1 of the invention comprising a cambium/xylem preferred promoter driving the expression of a nucleotide sequence coding for SAMdc 1 from *Oryza sativa* (rice).
Figure 11:
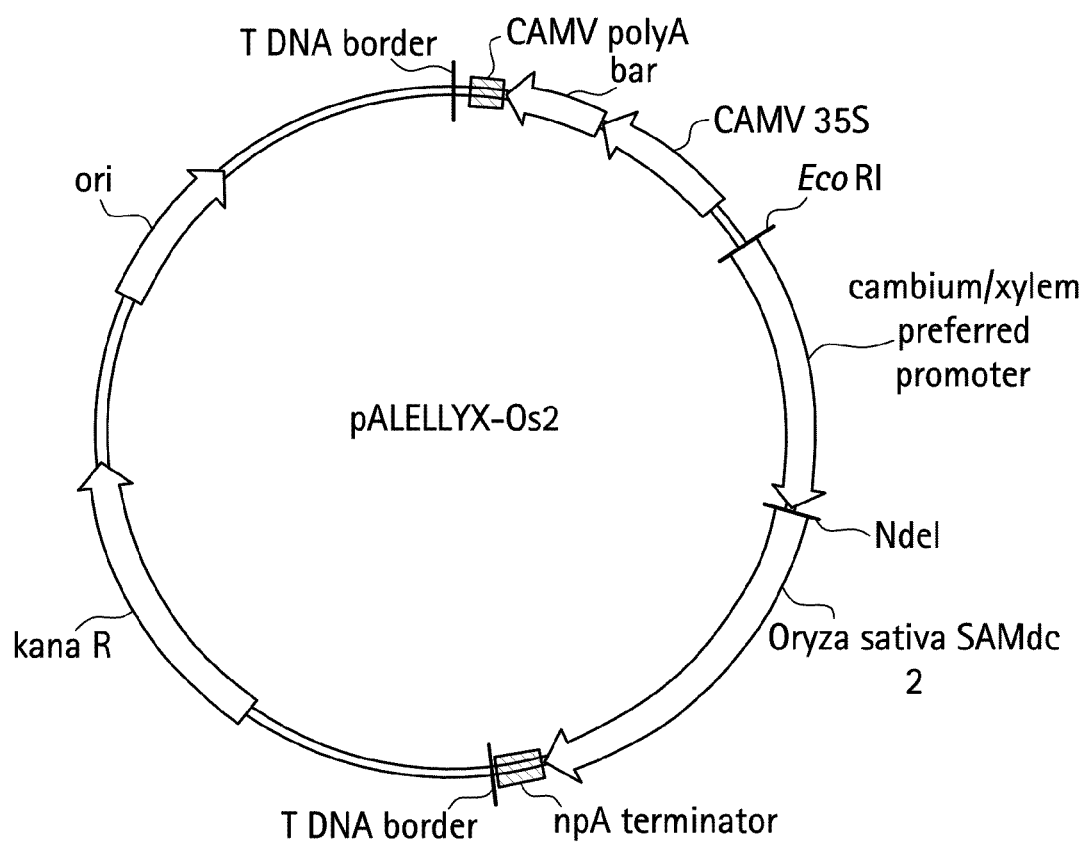
FIG. 11 schematically illustrates the plant expression plasmidial vector pALELLYX-Os2 of the invention comprising a cambium/xylem preferred promoter driving the expression of a nucleotide sequence coding for SAMdc 2 from *Oryza sativa* (rice).

Expression constructs can be prepared by cleaving the SAMdc genes obtained in 1 above with suitable restriction enzymes so as to include all of the open reading frame and inserting the gene into the plant transformation vector pALELLYX-ATG (FIG. 2) together with an appropriate promoter. For example, the tobacco SAMdc gene obtained in Example 1 was cloned into the aforementioned expression vector downstream to a xylem-preferred tubulin gene (TUB) promoter from *Populus deltoides* as set forth in PCT patent application No. PCT/BR2005/000041, filed Mar. 28, 2005, which claims for the priority date of Ser. No. 60/560,227, filed Apr. 6, 2004 (FIG. 3). The resulting expression construct is amplified in *E. coli*, and then transformed by tripartite conjugation, Bevan, *Nucleic Acid Research,* 12, 8711 (1984), freeze thawing, electroporation, chemical transformation or the like into *Agrobacterium tumefaciens* C58, GV3101 or the like.

(2) *Agrobacterium*-Mediated Transformation of *Arabidopsis thaliana*

*Arabidopsis thaliana* Columbia plants were transformed using an *Agrobacterium tumefaciens* mediated transformation protocol, Bechtold et al., *C.R. Acad. Sci. Paris,* 316, 1194-1199 (1993); Bent et al., *Mol. Gen. Genet.* 204, 383-396 (1986), with the construct containing the tobacco SAMdc gene obtained in Example 1 operably linked to the promoter of a xylem-preferred gene (TUB). The construct also contains the selectable marker gene Bar that confers resistance to herbicidal phosphinothricin analogs like ammonium glyphosinate. Thompson et al., *EMBO J.* 9:2519-2523 (1987).

Seeds of *Arabidopsis thaliana* ecotype Columbia were sown in pots containing vermiculite. Plants were grown at 16/8 hours dark/light regime at 22° C. After 4-5 weeks plants were transformed with the *Agrobacterium tumefaciens* strain GV3101 (C58C1 rifampicin) pMP90 (gentamicin), Bent et al., *Mol. Gen. Genet.* 204:383-396 (1986), harboring the plasmid vector comprising the SAMdc gene of interest operably linked to the TUB promoter.

For plant transformation, 1 liter of LB medium containing rifampicin, gentamycin and kanamicin was inoculated with an aliquot of overnight starter *Agrobacterium* culture. The culture was grown overnight at 28° C. in a rotatory shaker, until OD600 is ≧0.8. The *Agrobacterium* was precipitated by centrifugation and the bacterial pellet was ressuspended in ~300 ml of 5% sucrose and 0.03% Silwet L-77 (Witco). This *Agrobacterium* suspension was sprayed onto the plants. The pots were then placed in a tray which is covered with plastic wrap to maintain humidity. The plants were grown at 16/8 hours dark/light regime at 22° C. through maturity to set seeds.

Seeds were harvested, surface-sterilized in a solution containing 50% bleach and 0.02% Triton X-100 for 7 minutes. Seeds were then rinsed 3 times in sterile distilled water and plated out in MS medium containing 6 mg/l of Finale (Bayer) as selective agent. After 5 to 7 days, transformants were visible as green plants. Transformed plants were transferred onto new selection plates and after 6-10 days were transferred to pots containing vermiculite and grown under conditions of 16 hours light/8 hours dark at 22° C. After three weeks, the inflorescence stems were cut close to their bases twice a week for a period of one month in order to induce secondary growth at the base of the rosette before the plants were analyzed.

(3) *Agrobacterium*-Mediated Transformation of *Nicotiana benthamiana*

Transformation of *Nicotiana benthamiana* was accomplished using the leaf disk method of Horsch et al., *Science* 227, 1229, (1985), using a construct comprising the tobacco SAMdc gene obtained in Example 1 operably linked to the promoter of a xylem-preferred gene (4CL; Hu et al. *Proc. Natl. Acad. Sci. USA*, 95, 5407-5412 (1998)). The transformants were selected by growing on Murashige and Skoog medium (Sigma, St. Louis, Mo.) containing 100 milligrams/liter of BASTA herbicide and 500 mg/L carbenicillin (Sigma). The transformed tobacco shoots are allowed to root on the Murashige and Skoog medium, and are subsequently transferred to soil and grown in the greenhouse.

(4) PCR Verification of Foreign Gene Insertion into the Host Plant Genome

PCR can be used to verify the integration of the gene construct in the genome of transgenic plants. Two specific primers are synthesized for the construct and used to PCR-amplify the corresponding construct from genomic DNA of *Arabidopsis* or *Nicotiana* transformants. For the TUB-SAMdc-Nt construct, which contains the tobacco SAMdc main ORF under the control of the *Populus* xylem-preferred tubulin gene promoter, two specific primers were synthesized that amplify a 1.8 kb fragment:

```
Tub_check1     Length: 25      SEQ ID NO: 22
TATCGTTTTACTTCACTGGTCGGTG

SAMdc_Nt2      Length: 34      SEQ ID NO: 21
GTCTAGACTACTCCTTCTCTTCTTTCTCTTCATC
```

For the 4CL-SAMdc-Nt construct, which contains the tobacco SAMdc main ORF under the control of the *Populus* xylem-preferred 4CL gene promoter, two specific primers were synthesized that amplify a 1.6 kb fragment:

```
4CL_seq        Length: 20      SEQ ID NO: 23
AATCTCACCAACCCAACTCC

SAMdc_Nt2      Length: 34      SEQ ID NO: 21
GTCTAGACTACTCCTTCTCTTCTTTCTCTTCATC
```

The PCR reaction mixture contained 100 ng genomic DNA of transformed plant, and 0.2 μM of each primer, 100 μM of each deoxyribonucleotide triphosphate, 1×PCR buffer and 2.5 Units of AmpliTaq DNA polymerase (Applied Biosystems) in a total volume of 50 μL. The cycling parameters were as follows: 94° C. for 1 minute, 50° C. for 1 minute and 72° C. for 3 minutes, for 40 cycles, with 5 minutes at 72° C. extension. The PCR products were electrophoresized on an 1% agarose gel.

(5) Determination of Transgene Expression Level in Transgenic Plants

Semi-quantitative RT-PCR was used to detect the accumulation of tobacco SAMdc transcripts in stem tissue of the transgenic plants. Total RNA was isolated from 5-cm inflorescence stem cuts from transgenic *Arabidopsis* T1 plants (primary transformants) using Trizol reagent (GibcoBRL, USA) according to the manufacturer's instructions or from stem cuts of 3-months old transgenic *Nicotiana benthamiana* T1 plants using the CTAB method. Aldrich and Cullis, *Plant Mol. Biol. Report*, 11, 128-141 (1993).

cDNA was synthesized from 500 ng of total RNA using Superscript II RNase H-RT (Invitrogen, USA). Primers for the constitutive gene encoding adenine phosphoribosyltransferase (APRT), Moffatt et al., *Gene*, 143, 1211-1216 (1994), were used as an internal control to normalize the quantity of total RNA used in each sample. The PCR was done with a 12.5-fold dilution of the first-strand cDNA under the following conditions: 94° C. for 3 minutes and 27 cycles of 94° C. for 1 minute, 52 to 60° C. for 45 seconds, and 72° C. for 1 minute and 30 seconds.

Example 3

Histochemical Analysis of Transgenic Plants

Histological staining of lignin can be performed to analyze the amount of lignin in the vascular system of transformed and control plants. Briefly, stems of *Arabidopsis* TUB-SAMdc-Nt transgenic, *Nicotiana benthamiana* 4CL-SAMdc-Nt and control non-transgenic plants were free-hand sectioned with a razor blade, and the resulting sections were stained for total lignin with phloroglucinol-HCl (1% phloroglucinol in 6N HCl) for 30 minutes. Zhong et al., *Plant Physiol.*, 123, 59-69 (2000). Alternatively, tissues were sectioned in a microtome (Leica RM2255) and subsequently stained with phloroglucinol. The histologically stained sections are observed under a dissection microscope using bright- and dark-field illumination (FIGS. 12 and 14).

Example 4

Reduction in Lignin Content in Transgenic Plants Over-Expressing SAMdc in the Vascular Tissue The effect of over-expression of SAMdc in lignin biosynthesis in plant species was investigated in *Arabidopsis* and *Nicotiana*. It was found that over-expressing SAMdc in a xylem-preferred manner in transgenic *Arabidopsis* plants resulted in a reduction in lignin content (FIG. 12). Similar findings were obtained in two generations of transformed *Nicotiana* plants (FIG. 14). This finding indicates that over-expression of SAMdc is an efficient means for genetically engineering trees with low lignin content.

*Arabidopsis* transgenic plants were made following the methods described in Example 2. The first generation of transformants (T1) was analyzed using the methods described in Example 3 to assay lignin content, as well as vessel structure and vascular tissue anatomy. Several independent transformants were produced that contain a DNA expression construct comprising the *Nicotiana tabacum* SAMdc main ORF under the control of the *Populus* xylem-preferred tubulin gene promoter described in PCT patent application No. PCT/BR2005/000041, filed Mar. 28, 2005, which claims for the priority date of Ser. No. 60/560,227, filed Apr. 6, 2004, supra.

SAMdc gene expression levels were measured in twenty independent T1 plants, using the methods set forth in Example 2. Stems of transgenic plants were used for RNA extraction followed by a semi-quantitative RT-PCR. SAMdc gene expression levels in transgenic plants were expressed as a percentage of the maximum expression level observed.

Figure 13:
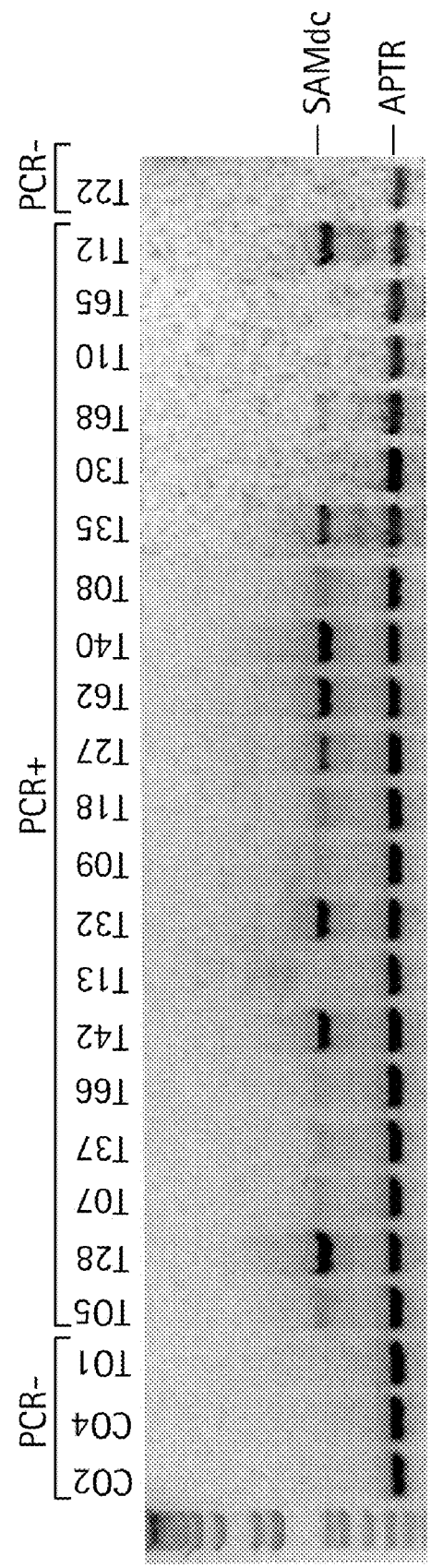
FIG. 13 exhibits a semi-quantitative RT-PCR experiment showing the transgene expression level (SAMdc) relative to the expression level of a control gene (APTR, adenine phosphoribosyltransferase) in transgenic (PCR+) and control non-transgenic (PCR−) TUB-SAMdc-Nt *Arabidopsis thaliana* plants.

As shown in FIG. 13, the transgenic *Arabidopsis* plant TUB-SAMdc-Nt12 showed a high transgene expression level (95% of the maximum level observed), which was accompanied by a decrease in phloroglucinol pinkish red staining intensity (FIG. 12B) compared to a comparable control non-transformed plant (FIG. 12A), reflecting a reduction in lignin content, which provides evidence that enhanced SAMdc expression in specific vascular cell types leads to a reduction in the availability of the methyl group donor SAM and therefore impairs lignin monomer biosynthesis during xylem lignification. Notably, although it exhibits a marked reduction in lignin content compared to a wild-type plant, the *Arabidopsis* transformant TUB-SAMdc-Nt12 has been grown normally under standard conditions, with no visible abnormal growth or morphology being observed.

Figure 12A:
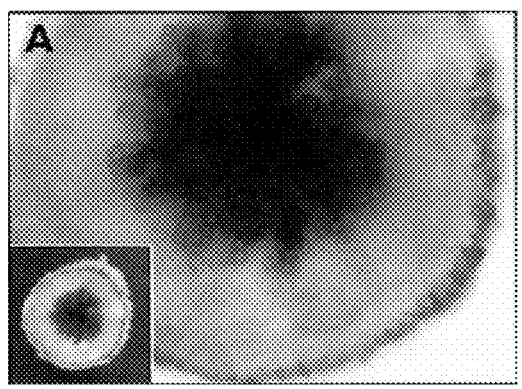
FIG. 12 shows hand-sectioned unfixed stems (rosette base level) of *Arabidopsis thaliana* stained with the lignin-specific dye phloroglucinol. (A) Control non-transgenic plant TUB-SAMdc-Nt22; (B) Transgenic plant TUB-SAMdc-Nt12, which exhibits a high transgene expression level (FIG. 13); (C) Control non-transgenic plant TUB-SAMdc-Nt01; (D) Transgenic plant TUB-SAMdc-Nt09. Insets represent lower magnification images of the respective stem cuts.
Figure 12B:
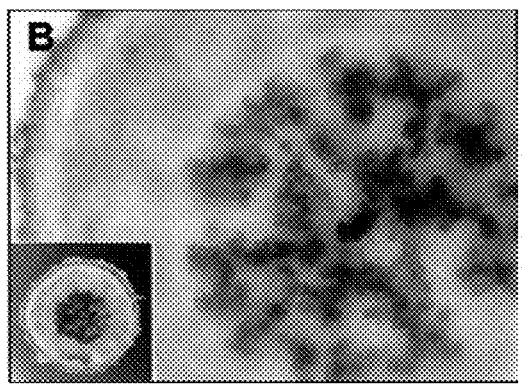
Figure 12C:
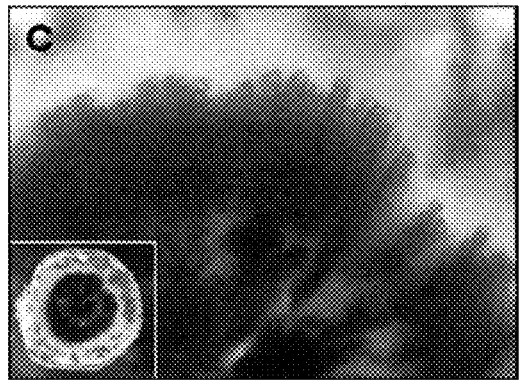
Figure 12D:
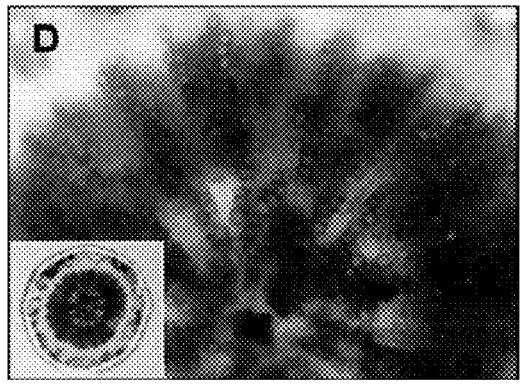

Other T1 plants with low or non-existent expression of the SAMdc transgene, like TUB-SAMdc-Nt09, failed to show any difference in phloroglucinol staining compared to comparable control non-transformed plants (FIGS. 12C, D).

Figure 14A:
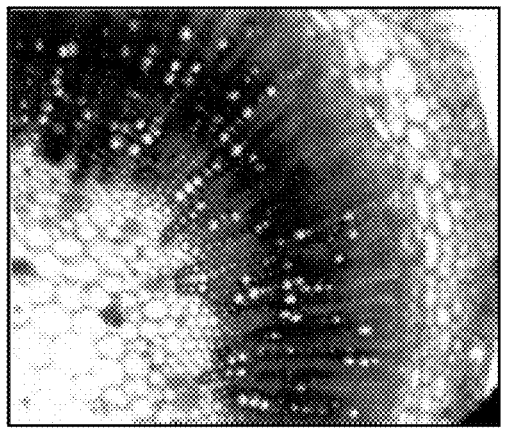
FIGS. 14(A) and (B) show hand-cut unfixed stem sections of 3 month-old *Nicotiana benthamiana* specimens, stained with the lignin-specific dye phloroglucinol in a control non-transgenic plant (A) and in a transgenic plant 4CL-SAMdc-Nt30 (B), which exhibits a high transgene expression level. (D) shows a homozygous transgenic plant in the T2 segregating population from the 4CL-SAMdc-Nt30T1 transformant compared to a control non-transgenic sibling plant (C). Note the decrease in vessel element number and size in (B) and the general decrease in lignin staining in (D).
Figure 14B:
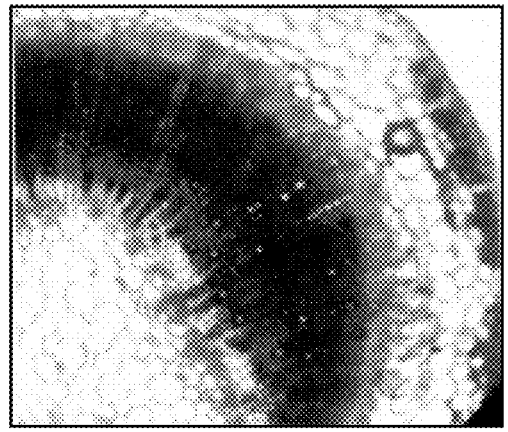
Figure 14C:
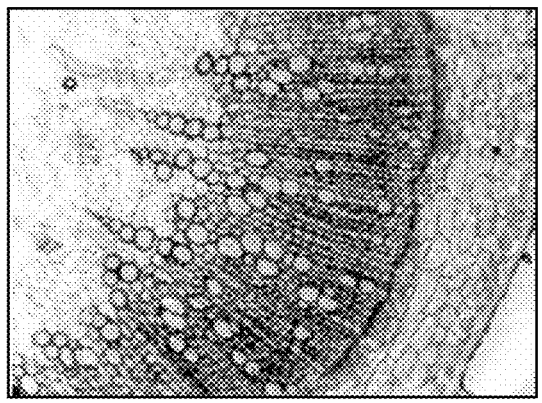
Figure 14D:
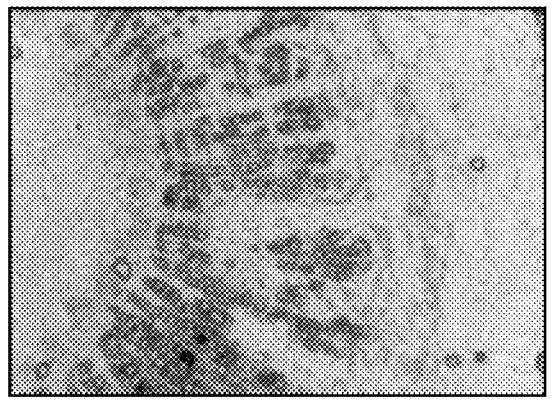
Figure 15:
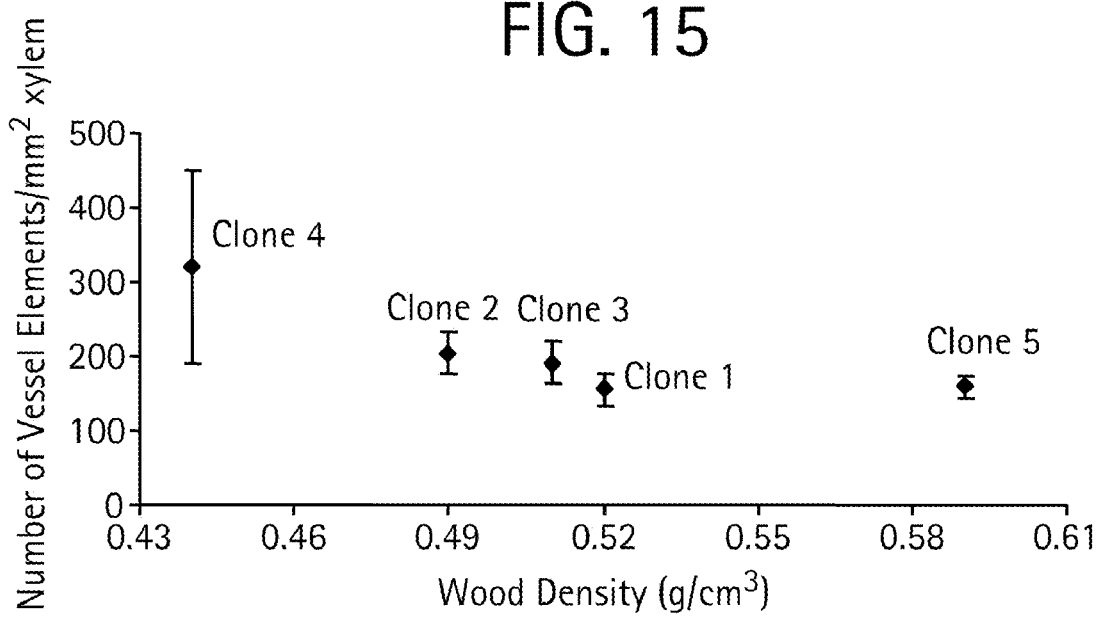
FIG. 15 shows the relationship between *Eucalyptus* clones wood density and the number of vessel elements in the xylem.

Similar results were obtained when the construct comprising the *Nicotiana tabacum* SAMdc main ORF under the control of the *Populus* xylem-preferred 4CL gene promoter, Hu et al, *Proc. Natl. Acad. Sci. USA*, 95, 5407-5412 (1998), was transformed into *Nicotiana benthamiana* plants. *Nicotiana benthamiana* transgenic plants were made following the methods described in Example 2. Several independent first-generation transformants (T1) were analyzed using the methods described in Example 3 to assay lignin content, as well as vascular tissue anatomy. As shown in FIG. 14, the transgenic *Nicotiana benthamiana* plant 4CL-SAMdc-Nt30 showed a marked decrease in the number of vessel elements in the vascular tissue (FIG. 14B) compared to a control non-transformed plant (FIG. 14A). This might reflect a reduction in the plant's ability to deposit lignin in the cell wall. Seeds from this transgenic plant were germinated to obtain a segregating population of plants in the following generation (T2). These segregants could be separated into three groups according to transgene expression level and plant size. Heterozygous and homozygous T2 plants possessed a reduction in size and a strong reduction in lignin content as assessed by phloroglucinol staining according to Example 3 (FIG. 14D), as compared to non-transgenic sibling plants (FIG. 14C), providing strong evidence that enhanced SAMdc expression in specific vascular cell types leads to a reduction in the availability of the methyl group donor SAM and therefore impairs lignin monomer biosynthesis during xylem lignification.

Example 5

Isolation of *Populus* cDNA Encoding SAMdc Enzyme (A) Preparation of RNA from *Populus deltoides* Cambium/Xylem and cDNA Synthesis.

Bark was removed from stem cuttings of one-year-old *Populus deltoides* trees. The inner part of the stem, containing cambium, xylem, and pith, was cut into small pieces, frozen in liquid nitrogen and used for RNA extraction using the cetyltrimethyl-ammonium bromide (CTAB) extraction method. Aldrich and Cullis, *Plant Mol. Biol. Report.* 11: 128-41 (1993). A cDNA pool was used in RT-PCR experiments in which the isolated total RNA was used as template, and Superscript II reverse transcriptase (Invitrogen) and oligo (dT) primer were used to synthesize the first-strand cDNA. Double-stranded cDNA was obtained by the subsequent polymerase reaction, using gene-specific primers, as described below.

(B) Design of PCR Primers and RT-PCR Reaction.

Oligomers based on SEQ ID NO: 26 were synthesized as primers for PCR, including either the region around the first ATG codon or around the termination codon of the main ORF encoding the polypeptide to amplify the entire coding region of the main ORF. The sequences of the primers are:

```
SAMDC_NCO       Length: 26      SEQ ID NO: 28
CCATGGCGCT GCCAGTCTCT GCAATC

SAMDC_XBA       Length: 27      SEQ ID NO: 29
TCTAGACTAC TTCTCTTCAG CTTCCTC
```

The cDNA pool obtained in (A) was used as the template in a PCR reaction with the primers of SEQ ID NOs: 28 and 29. The PCR involved 40 cycles of 1 minute at 94° C., 1 minute at 51° C., and 2 minutes at 72° C. followed by an extra step of elongation at 72° C. for 7 minutes. The PCR products were isolated by gel electrophoresis on 1.0% agarose followed by ethidium bromide staining of the electrophoresed gel and detection of amplified bands on a UV transilluminator. The detected amplified band was verified and cut out of the agarose gel with a razor. The pieces of gel were transferred to 1.5 mL microtubes, and the DNA fragments were isolated and purified using a GFX PCR clean-up and gel band purification kit (Amersham). The recovered DNA fragments were subcloned in a commercially available cloning vector, transformed into *E. coli*, and then used to prepare plasmid DNA, which was then sequenced by the dideoxy method, Messing, *Methods in Enzymol.* 101, 20-78 (1983), using standard methods.

Example 6

Preparation of Transgenic *Populus* and *Eucalyptus* Plants

The gene obtained in Examples 5 above was introduced into a plant host to produce transgenic *Populus* and *Eucalyptus* plants.

(A) Preparation of Constructs and Transformation of *Agrobacterium*

Expression constructs can be prepared by cleaving the SAMdc gene obtained in Example 5 above with suitable restriction enzymes so as to include the entire open reading frame and inserting the gene into the plant transformation vector pALELLYX-ATG (FIG. 2) together with an appropriate promoter. For example, the *Populus* SAMdc gene obtained in Example 5 was cloned into the aforementioned expression vector downstream to a xylem-preferred 4CL gene promoter, Hu et al., *PNAS* 95: 5407-5412 (1998), from *Populus deltoides*. The resulting expression construct is amplified in *E. coli*, and then transformed by tripartite conjugation, Bevan, *Nucleic Acid Research* 12, 8711-8721

(1984), freeze thawing, electroporation, chemical transformation or the like into *Agrobacterium tumefaciens* C58, GV3101, or the like.

(B) *Agrobacterium*-Mediated Transformation of *Populus*

Wild-type aspen was transformed with *Agrobacterium tumefaciens* carrying a construct comprising a *Populus deltoides* SAMdc gene obtained in Example 5 operably linked to the promoter of a xylem-preferred gene (C4H). Petioles and internodal stem segments from in vitro micropropagated plants were used as explants. Transformed shoots are selected on regeneration medium containing 100 mg/L of kanamycin and allowed to root on the Murashige and Skoog medium. Selected plants are subsequently transferred to soil and grown in the greenhouse.

(C) *Agrobacterium*-Mediated Transformation of *Eucalyptus*

Transformation of hybrid *Eucalyptus* (*Eucalyptus grandis* x *Eucalyptus urophylla*) was accomplished by cocultivation of hypocotyl segments with *Agrobacterium tumefaciens* containing a construct comprising a *Populus deltoides* SAMdc gene obtained in Example 5 operably linked to the promoter of a xylem-preferred gene (C4H). AHAS-resistant lines were allowed to root on the Murashige and Skoog medium and selected plants were subsequently transferred to soil and grown in the greenhouse.

Example 7

Reduction of Vessel Number and Vessel Lumen Area in Transgenic Plants Over-expressing SAMdc in the Vascular Tissue Stem sections of 10 µm thick were cut from the *Nicotiana benthamiana* segregating population of plants described in Example 2. These sections were subjected to safranin-astra blue coloration and observed under a light microscope (Leica DMIL) fitted with a camera (Sony) linked to a personal computer.

The number of vessels per mm² of xylem area and the average lumen area of 100 vessels were measured directly on the screen using the "Image Tool" software.

Figure 16A:
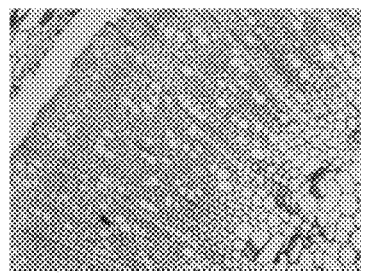
FIG. 16 shows hand-sectioned unfixed stems (base level) of a T1 transgenic *Nicotiana benthamiana* plants (line 11B) transformed with the plant expression plasmidial vector pALELLYX-Nt stained with the lignin-specific dye phloroglucinol. (A) sdcsdc genotype; (B) SDCSDC genotype; (C) reduction on the vessel elements number of the T1 transgenic plants (line 11B).
Figure 16B:
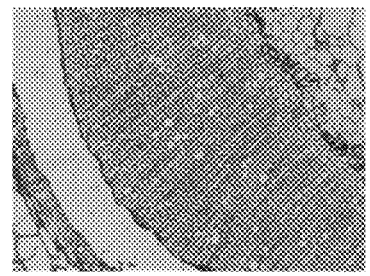
Figure 16C:
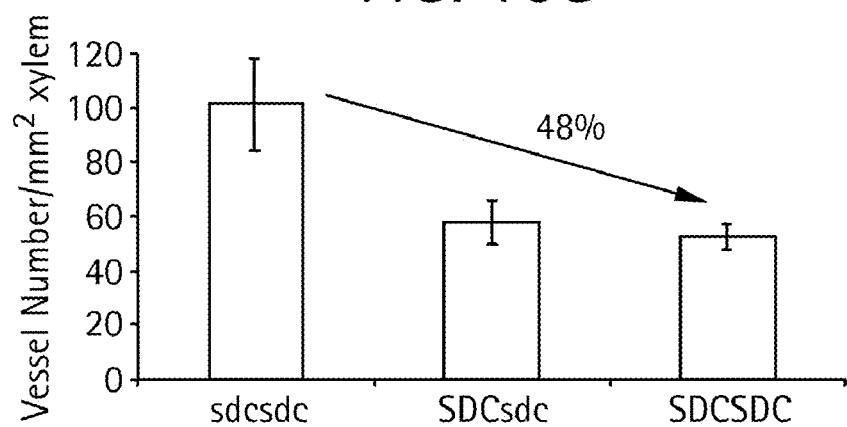

The homozygous dominant plants and the hemizygous plants presented a significant decrease in the number of vessels, compared with the homozygous recessive plants. There is a reduction of 48% in the number of vessels of homozygous dominant plants when compared to homozygous recessive plants (FIG. 16). The Tukey test showed that the difference between the two populations is highly significant with P<0.001.

Observations of the homozygous dominant population also revealed that the measured average area of 100 vessels in these plants was 57% smaller when compared to the average area of homozygous recessive plants (FIG. 17). The Tukey test showed that the difference between the two populations is highly significant with P<0.001. No significant difference was observed between homozygous dominant and hemizygous plants.

Example 8

Histochemical Analysis of Transgenic Plants

Lateral shoots of 6 months old Eucalyptus plants described in Example 6 were cross-sectioned (5 µm thick) from wild-type and the transgenic lines with a microtome (LEICA RM2255) equipped with a steel knife. These sections were subjected to astra-blue staining and were observed under a light microscope just after staining. FIG. 19A shows a stem section of transgenic event A.12.3 presenting strong reduction in the number and the size of vessel elements when compared to a wild-type plant (FIG. 19B).

Example 9

Reduction of Insoluble Lignin and Increase of Soluble Lignin in Transgenic Plants The main stems of T1 segregating population of the *Nicotiana* transgenic event 11B transformed with a construct comprising the *Nicotiana tabacum* SAMdc gene under the control of the xylem-preferred *Populus deltoides* 4CL promoter were collected and air-dried for two weeks. Dried stems were cut in pieces and pulverized on a knife mill using a 30-mesh sieve. Stem powder samples were then subjected to chemical analyses to determine lignin content. In brief, to a sample of extracted tobacco was added an aliquot of 72% (w/w) $H_2SO_4$ and was thoroughly mixed for 1 minute. After 2 hours of hydrolysis, the content was transferred to a serum bottle and the serum bottles (containing $H_2SO_4$ at 4% (w/w) plus tobacco) were autoclaved at 121° C. for 60 minutes. Samples were allowed to cool, and the hydrolysates were vacuum-filtered, washed with 200 ml warm (approximately 50° C.) nanopure $H_2O$ to remove residual acid and sugars and dried overnight at 105° C. The dry crucibles were weighed to determine Klason (acid-insoluble lignin) lignin gravimetrically. The filtrate was also analysed for acid-soluble lignin by absorbance at 205 nm. Patzlaff et al., *Plant J.* 36: 743-754 (2003).

Figure 20A:
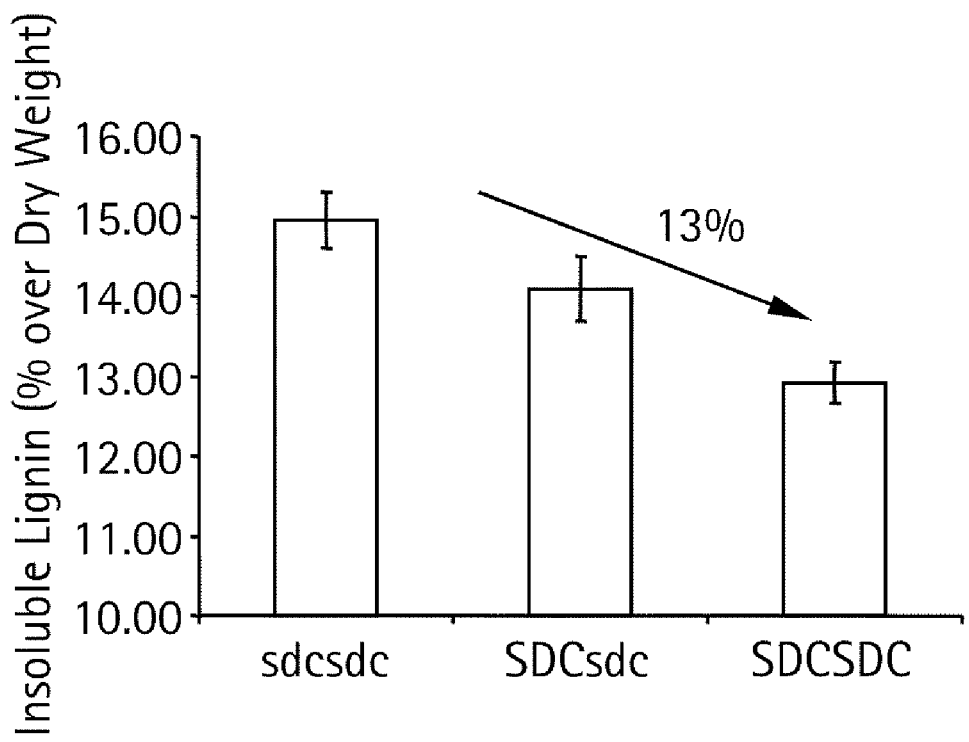
FIG. 20 shows the insoluble (A) and soluble (B) lignin content of three genotypes of a T1 transgenic *Nicotiana benthamiana* plants (line 11B) transformed with the plant expression plasmidial vector pALELLYX-Nt.
Figure 20B:
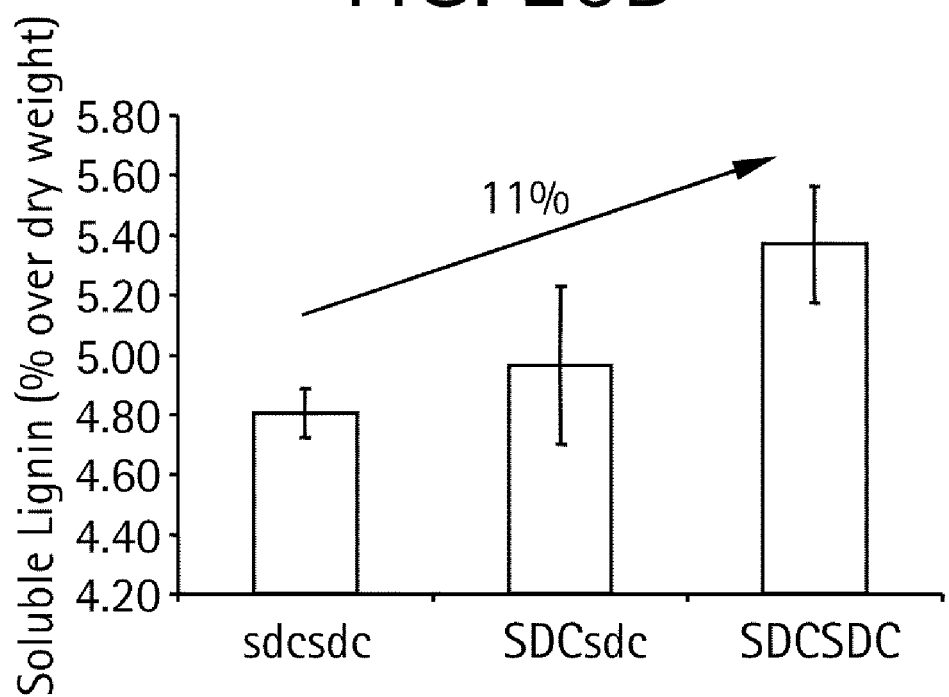

As shown in FIG. 20A, the homozygous dominant plants presented a decrease of 13% in their insoluble lignin content, when compared to homozygous recessive plants. The homozygous dominant plants also presented an increase of 11% in their soluble lignin content, compared to homozygous recessive plants (FIG. 20B)

What is claimed is:

1. A nucleic acid construct comprising a SAMdc nucleotide sequence and, operably linked thereto, a xylem-preferred promoter.

2. A plant comprising the construct of claim 1.

3. The plant of claim 2, wherein said plant is an angiosperm.

4. The plant of claim 2, wherein said plant is a gymnosperm.

5. A plant or part thereof that overexpresses a nucleotide sequence encoding a SAMdc enzyme, which nucleotide sequence is under the control of a xylem-preferred promoter, such that said plant has reduced lignin levels compared with a control plant.

6. The plant of claim 5, wherein said plant is an angiosperm.

7. The plant of claim 5, wherein said plant is a gymnosperm.

8. The plant of claim 5, wherein said plant is a woody tree.

9. The plant of claim 6, wherein said woody tree is a *Eucalyptus* plant.

10. The plant of claim 6, wherein said woody tree is a *Populus* plant.

11. The plant of claim 7, wherein said woody tree is a *Pinus* plant.

12. A part of the plant of claim 5, wherein said part is selected from the group consisting of a leaf, a stem, a flower, an ovary, a fruit, a seed, and a callus, wherein said part comprises a SAMdc nucleotide sequence and, operably linked thereto, a xylem-preferred promoter.

13. Progeny of the plant of claim 5, wherein said progeny comprise a SAMdc nucleotide sequence and, operably linked thereto, a xylem-preferred promoter.

14. A method for decreasing lignin content in a plant, comprising: (a) introducing into a plant cell a nucleic acid construct comprising, in the 5' to 3' direction, a xylem-preferred promoter operably linked to a SAMdc nucleotide sequence; (b) regenerating transgenic plants from said plant cell; and (c) selecting a transgenic plant having decreased lignin content relative to a control plant.

15. The method of claim 14, wherein said plant is an angiosperm.

16. The method of claim 14, wherein said plant is a gymnosperm.

17. The method of claim 15, wherein said plant is *Eucalyptus* or *Populus*.

18. The method of claim 16, wherein said plant is *Pinus*.

19. The method of claim 14, wherein said nucleic acid is selected from the group consisting of: (a) a nucleotide sequence set forth in any of SEQ ID NO: 1, 3, 5, 7, 9, 11, 13, 15, 17, 19, 24, and 26; (b) a nucleotide sequence that encodes a polypeptide having the amino acid sequence set forth in any of SEQ ID NO: 2, 4, 6, 8, 10, 12, 14, 16, and 18; (c) a nucleotide sequence that differs from the nucleotide sequences of (a) or (b) due to degeneracy of the genetic code and encodes a polypeptide with SAMdc enzyme activity.

20. A method for increasing the ratio of syringyl lignin to guaiacyl lignin in a woody plant, comprising overexpressing a SAMdc nucleotide sequence with a xylem-preferred promoter.

21. A method for increasing wood density in a plant, comprising (a) introducing into a plant cell a nucleic acid construct comprising, in the 5' to 3' direction, a xylem-preferred promoter operably linked to a SAMdc nucleotide sequence; (b) regenerating transgenic plants from said plant cell; and (c) selecting a transgenic plant having reduced vessel area and reduced vessel density relative to a control plant.

22. The method of claim 21, wherein said plant is an angiosperm.

23. The method of claim 21, wherein said plant is a gymnosperm.

24. The method of claim 22, wherein said plant is *Eucalyptus* or *Populus*.

25. The method of claim 23, wherein said plant is *Pinus*.

26. Wood pulp obtained from a transgenic plant produced by the method of claim 21, wherein said wood pulp comprises a SAMdc nucleotide sequence and, operably linked thereto, a xylem-preferred promoter.

27. Wood fiber obtained from a transgenic plant produced by the method of claim 21, wherein said wood fiber comprises a SAMdc nucleotide sequence and, operably linked thereto, a xylem-preferred promoter.

28. A method for increasing wood density and decreasing lignin content in a plant, comprising: (a) introducing into a plant cell a nucleic acid construct comprising, in the 5' to 3' direction, a xylem-preferred promoter operably linked to a SAMdc nucleotide sequence; (b) regenerating transgenic plants from said plant cell; and (c) selecting a transgenic plant having increased wood density and decreased lignin content relative to a control plant.

29. The method of claim 28, wherein said plant is an angiosperm.

30. The method of claim 28, wherein said plant is a gymnosperm.

31. The method of claim 29, wherein said plant is *Eucalyptus* or *Populus*.

32. The method of claim 30, wherein said plant is *Pinus*.

33. A method of making wood pulp, comprising (a) introducing into a plant cell a nucleic acid construct comprising, in the 5' to 3' direction, a xylem-preferred promoter operably linked to a SAMdc nucleotide sequence; (b) regenerating transgenic plants from said plant cell; (c) selecting a transgenic plant having increased wood density and decreased lignin content relative to a control plant; and (d) producing wood pulp from said transgenic plant.

34. The method of claim 33, wherein said xylem-preferred promoter is selected from the group consisting of TUB gene promoter, LTP gene promoter, 4CL gene promoter, and C4H gene promoter.

35. A method of making wood fiber, comprising (a) introducing into a plant cell a nucleic acid construct comprising, in the 5' to 3' direction, a xylem-preferred promoter operably linked to a SAMdc nucleotide sequence; (b) regenerating transgenic plants from said plant cell; (c) selecting a transgenic plant having increased wood density and decreased lignin content relative to a control plant; and (d) producing wood fiber from said transgenic plant.

* * * * *

SEQUENCE LISTING

```
<160> NUMBER OF SEQ ID NOS: 29

<210> SEQ ID NO 1
<211> LENGTH: 1658
<212> TYPE: DNA
<213> ORGANISM: Nicotiana tabacum
<220> FEATURE:
<221> NAME/KEY: CDS
<222> LOCATION: (364)..(1446)

<400> SEQUENCE: 1
```

-continued

```
atggagtcga aaggtggtaa aaactctagt agtaaatcct taccctacga agcacccctc    60
ggctacagta ttgaagacgt tcggccaaac ggtggaatca agaagttcag atcagctgct   120
tactccaact gcgctcgcaa accatcctga cattccttaa gcttctctcc tgcacgtgtc   180
tcctgacaca aaaagaaaa aatccccaaa aaaagttcct tctgtcaatt gttttttgttg  240 ttaaaccctc actccttttc ctcaatttct tccttctgct gctttctgct cttgctctcc   300
ttggctgtga acaattttct ttaaaagatc atttgttgct gtgaacatat ttttttttat   360
```

| | | | | | | | | | | | | | | | | |
|---|---|---|---|---|---|---|---|---|---|---|---|---|---|---|---|---|
| cta | atg | gat | tcg | gcc | ttg | cct | gtc | tct | gcc | att | ggt | ttt | gaa | ggt | ttc | 408 |
| | Met | Asp | Ser | Ala | Leu | Pro | Val | Ser | Ala | Ile | Gly | Phe | Glu | Gly | Phe | |
| | 1 | | | 5 | | | | | 10 | | | | | 15 | | |

| | | | | | | | | | | | | | | | |
|---|---|---|---|---|---|---|---|---|---|---|---|---|---|---|---|
| gag | aag | agg | ctt | gaa | att | tct | ttt | ttc | gag | cct | ggt | ctg | ttt | gct | gat | 456 |
| Glu | Lys | Arg | Leu | Glu | Ile | Ser | Phe | Phe | Glu | Pro | Gly | Leu | Phe | Ala | Asp |
| | | 20 | | | | | 25 | | | | | 30 | | | |

| ccc | aac | gga | aaa | gga | ctt | cga | tct | ctc | tca | aag | gca | caa | ttg | gat | gag | 504 |
| Pro | Asn | Gly | Lys | Gly | Leu | Arg | Ser | Leu | Ser | Lys | Ala | Gln | Leu | Asp | Glu |
| | | | 35 | | | | | 40 | | | | | 45 | | |

| att | ctc | gga | cct | gct | gag | tgc | acc | ata | gtt | gat | tcc | cta | tca | aat | gac | 552 |
| Ile | Leu | Gly | Pro | Ala | Glu | Cys | Thr | Ile | Val | Asp | Ser | Leu | Ser | Asn | Asp |
| | | 50 | | | | | 55 | | | | | 60 | | | |

| gat | gtt | gat | tct | tat | gtc | ctc | tcc | gag | tcg | agc | ctc | ttt | gtt | tat | tct | 600 |
| Asp | Val | Asp | Ser | Tyr | Val | Leu | Ser | Glu | Ser | Ser | Leu | Phe | Val | Tyr | Ser |
| 65 | | | | | 70 | | | | | 75 | | | | | |

| tac | aag | ata | atc | atc | aaa | acc | tgt | ggc | acc | aca | aag | ttg | ctt | ctc | gca | 648 |
| Tyr | Lys | Ile | Ile | Ile | Lys | Thr | Cys | Gly | Thr | Thr | Lys | Leu | Leu | Leu | Ala |
| 80 | | | | | 85 | | | | | 90 | | | | | 95 |

| att | ccg | ccc | atc | cta | aag | ttg | gct | gag | acc | ctg | tct | ctc | aaa | gta | caa | 696 |
| Ile | Pro | Pro | Ile | Leu | Lys | Leu | Ala | Glu | Thr | Leu | Ser | Leu | Lys | Val | Gln |
| | | | | 100 | | | | | 105 | | | | | 110 | |

| gac | gtg | agg | tat | acc | cgt | ggg | agc | ttc | att | ttc | cct | ggc | gct | cag | tcg | 744 |
| Asp | Val | Arg | Tyr | Thr | Arg | Gly | Ser | Phe | Ile | Phe | Pro | Gly | Ala | Gln | Ser |
| | | | 115 | | | | | 120 | | | | | 125 | | |

| ttt | cct | cat | cgt | cac | ttc | tct | gaa | gaa | gtt | gct | gtc | ctc | gat | ggc | tat | 792 |
| Phe | Pro | His | Arg | His | Phe | Ser | Glu | Glu | Val | Ala | Val | Leu | Asp | Gly | Tyr |
| | | 130 | | | | | 135 | | | | | 140 | | | |

| ttt | gga | aag | ctt | gct | gcc | ggt | agc | aag | gct | gtg | att | atg | ggc | agt | cct | 840 |
| Phe | Gly | Lys | Leu | Ala | Ala | Gly | Ser | Lys | Ala | Val | Ile | Met | Gly | Ser | Pro |
| | 145 | | | | | 150 | | | | | 155 | | | | |

| gac | aaa | gca | cag | aaa | tgg | cat | gtt | tac | tct | gcc | tct | gca | gga | cct | att | 888 |
| Asp | Lys | Ala | Gln | Lys | Trp | His | Val | Tyr | Ser | Ala | Ser | Ala | Gly | Pro | Ile |
| 160 | | | | 165 | | | | | 170 | | | | | 175 | |

| cag | tct | aat | gac | cct | gtt | tac | act | ctt | gag | atg | tgt | atg | act | ggt | ttg | 936 |
| Gln | Ser | Asn | Asp | Pro | Val | Tyr | Thr | Leu | Glu | Met | Cys | Met | Thr | Gly | Leu |
| | | | 180 | | | | | 185 | | | | | 190 | | |

| gac | agg | gag | aag | gca | tct | gtc | ttt | tac | aag | act | gaa | gga | agc | tcg | gct | 984 |
| Asp | Arg | Glu | Lys | Ala | Ser | Val | Phe | Tyr | Lys | Thr | Glu | Gly | Ser | Ser | Ala |
| | | | 195 | | | | | 200 | | | | | 205 | | |

| gct | cat | atg | act | gtt | cga | tct | gga | ata | agg | aag | atc | ctc | ccc | aat | tct | 1032 |
| Ala | His | Met | Thr | Val | Arg | Ser | Gly | Ile | Arg | Lys | Ile | Leu | Pro | Asn | Ser |
| | | 210 | | | | | 215 | | | | | 220 | | | |

| gag | ata | tgc | gat | ttt | gag | ttt | gaa | ccc | tgt | ggt | tat | tcc | atg | aat | tca | 1080 |
| Glu | Ile | Cys | Asp | Phe | Glu | Phe | Glu | Pro | Cys | Gly | Tyr | Ser | Met | Asn | Ser |
| | 225 | | | | | 230 | | | | | 235 | | | | |

| att | gaa | gga | gct | gca | ctc | tca | acc | att | cac | att | acc | ccg | gaa | gat | ggc | 1128 |
| Ile | Glu | Gly | Ala | Ala | Leu | Ser | Thr | Ile | His | Ile | Thr | Pro | Glu | Asp | Gly |
| 240 | | | | 245 | | | | | 250 | | | | | 255 | |

| ttt | agc | tat | gct | agc | ttt | gaa | gca | gtt | ggg | tat | gac | atg | aaa | acc | atg | 1176 |
| Phe | Ser | Tyr | Ala | Ser | Phe | Glu | Ala | Val | Gly | Tyr | Asp | Met | Lys | Thr | Met |
| | | | 260 | | | | | 265 | | | | | 270 | | |

```
aag ctg ggt ccc ctg gtt gag agg gtg ctg gca tgt ttc cag cca gat    1224
Lys Leu Gly Pro Leu Val Glu Arg Val Leu Ala Cys Phe Gln Pro Asp
            275                 280                 285 gag ttc tct att gct ttg cat gct gat gtt gct acc aag tta ctg gag    1272
Glu Phe Ser Ile Ala Leu His Ala Asp Val Ala Thr Lys Leu Leu Glu
        290                 295                 300 cgt gtt tgc tct ctt gat gtg aaa ggc tac tct ctt gct gag tgg agt    1320
Arg Val Cys Ser Leu Asp Val Lys Gly Tyr Ser Leu Ala Glu Trp Ser
305                 310                 315 cca gaa gaa ttt ggc aag ggt ggt tcc att gtc tac cag aag ttc acc    1368
Pro Glu Glu Phe Gly Lys Gly Gly Ser Ile Val Tyr Gln Lys Phe Thr
320                 325                 330                 335 aga act cct ttc tgt gga tct ccc aag tcc gtt ctg aag ggc tgc tgg    1416
Arg Thr Pro Phe Cys Gly Ser Pro Lys Ser Val Leu Lys Gly Cys Trp
                340                 345                 350 aaa gaa gat gaa gag aaa gaa gag aag gag tagtgtcttg agggctgtgt      1466
Lys Glu Asp Glu Glu Lys Glu Glu Lys Glu
                355                 360 tgttttttgt ttcagtgtcc gtgtctgtct ctgtctgtgt cggtgtcgtt tgttttttca    1526
gtgtttctcc gaataaagta cttgatgtcc aagctgtgtc gtttggattt gtaatgccga    1586
tgtgcaaatt ctgaactatt cttggctttt tgtgttccac ccgaagccct atgaacctgc    1646
attttgaata aa                                                        1658

<210> SEQ ID NO 2
<211> LENGTH: 361
<212> TYPE: PRT
<213> ORGANISM: Nicotiana tabacum

<400> SEQUENCE: 2

Met Asp Ser Ala Leu Pro Val Ser Ala Ile Gly Phe Glu Gly Phe Glu
1               5                   10                  15

Lys Arg Leu Glu Ile Ser Phe Phe Glu Pro Gly Leu Phe Ala Asp Pro
            20                  25                  30

Asn Gly Lys Gly Leu Arg Ser Leu Ser Lys Ala Gln Leu Asp Glu Ile
        35                  40                  45

Leu Gly Pro Ala Glu Cys Thr Ile Val Asp Ser Leu Ser Asn Asp Asp
    50                  55                  60

Val Asp Ser Tyr Val Leu Ser Glu Ser Ser Leu Phe Val Tyr Ser Tyr
65                  70                  75                  80

Lys Ile Ile Ile Lys Thr Cys Gly Thr Thr Lys Leu Leu Leu Ala Ile
                85                  90                  95

Pro Pro Ile Leu Lys Leu Ala Glu Thr Leu Ser Leu Lys Val Gln Asp
            100                 105                 110

Val Arg Tyr Thr Arg Gly Ser Phe Ile Phe Pro Gly Ala Gln Ser Phe
        115                 120                 125

Pro His Arg His Phe Ser Glu Glu Val Ala Val Leu Asp Gly Tyr Phe
    130                 135                 140

Gly Lys Leu Ala Ala Gly Ser Lys Ala Val Ile Met Gly Ser Pro Asp
145                 150                 155                 160

Lys Ala Gln Lys Trp His Val Tyr Ser Ala Ser Ala Gly Pro Ile Gln
                165                 170                 175

Ser Asn Asp Pro Val Tyr Thr Leu Glu Met Cys Met Thr Gly Leu Asp
            180                 185                 190

Arg Glu Lys Ala Ser Val Phe Tyr Lys Thr Glu Gly Ser Ser Ala Ala
        195                 200                 205
```

```
His Met Thr Val Arg Ser Gly Ile Arg Lys Ile Leu Pro Asn Ser Glu
    210                 215                 220
Ile Cys Asp Phe Glu Phe Glu Pro Cys Gly Tyr Ser Met Asn Ser Ile
225                 230                 235                 240
Glu Gly Ala Ala Leu Ser Thr Ile His Ile Thr Pro Glu Asp Gly Phe
                    245                 250                 255
Ser Tyr Ala Ser Phe Glu Ala Val Gly Tyr Asp Met Lys Thr Met Lys
                260                 265                 270
Leu Gly Pro Leu Val Glu Arg Val Leu Ala Cys Phe Gln Pro Asp Glu
            275                 280                 285
Phe Ser Ile Ala Leu His Ala Asp Val Ala Thr Lys Leu Leu Glu Arg
    290                 295                 300
Val Cys Ser Leu Asp Val Lys Gly Tyr Ser Leu Ala Glu Trp Ser Pro
305                 310                 315                 320
Glu Glu Phe Gly Lys Gly Gly Ser Ile Val Tyr Gln Lys Phe Thr Arg
                325                 330                 335
Thr Pro Phe Cys Gly Ser Pro Lys Ser Val Leu Lys Gly Cys Trp Lys
                340                 345                 350
Glu Asp Glu Glu Lys Glu Glu Lys Glu
            355                 360

<210> SEQ ID NO 3
<211> LENGTH: 1777
<212> TYPE: DNA
<213> ORGANISM: Populus deltoides
<220> FEATURE:
<221> NAME/KEY: CDS
<222> LOCATION: (536)..(1618)

<400> SEQUENCE: 3
tcggacacaa aaatattgc aagtttaggg tcataaaaat ctctatcatc acaaacaaat      60
atagggtttg ttgatttggt ggctgttttc gccgtctttg ctttcaaaat tcaatcttga     120
cctgtttctt ttatgctttt tgaataggtt ttttttttga acttgagaaa gaggggtttt     180
tcaaaggaga ctagcttttc aagatttgat atatttatt ggactgaatg atctaatgga      240
gtctaaaggt ggcaagaaga agtctagtag tagtagtagt agtaaatcct tatgttacga     300 agctccctc ggttacagca ttgaagacct cagacctgct ggtggaatca agaagttcag      360
atctgctgca tactccaact gcgttcgaaa accatcctga gattttccaa gtgttgacat     420
aaccccattt tagctatttc gcacgctcaa ttgtctttag tctgttttc tgttctgctt      480 tcctcgttct cttgtactct ttgctgcact tttcatttgt tgactgtgag gtcag atg     538
                                                              Met
                                                                1 gcg ctg cca gtc tct gca atc gga ttt gaa ggt tac gaa aaa agg ctt     586
Ala Leu Pro Val Ser Ala Ile Gly Phe Glu Gly Tyr Glu Lys Arg Leu
      5                  10                  15 gaa ata tct ttc cta gag cct ggc ttc ttt tct gac cct gaa ggg aag     634
Glu Ile Ser Phe Leu Glu Pro Gly Phe Phe Ser Asp Pro Glu Gly Lys
         20                  25                  30 ggc ctg agg tct ttg tcc aag gct caa ttg gac gag att ctc aga cca     682
Gly Leu Arg Ser Leu Ser Lys Ala Gln Leu Asp Glu Ile Leu Arg Pro
     35                  40                  45 gct gaa tgt act att gtt gat tcg cta tca aat gac cag gtt gat tct     730
Ala Glu Cys Thr Ile Val Asp Ser Leu Ser Asn Asp Gln Val Asp Ser
 50                  55                  60                  65 tat gtc ctg tcg gaa tcc agt ctc ttt gtg tac cct tac aaa gtt att     778
Tyr Val Leu Ser Glu Ser Ser Leu Phe Val Tyr Pro Tyr Lys Val Ile
                 70                  75                  80
```

```
atc aaa aca tgt ggg act acc aaa ctg ctt ctc tct ata ccg gtg att    826
Ile Lys Thr Cys Gly Thr Thr Lys Leu Leu Leu Ser Ile Pro Val Ile
             85                  90                  95 ctt aag ctc gct gat gcc ctt tca ctc act gta tgt tct gtg agg tat    874
Leu Lys Leu Ala Asp Ala Leu Ser Leu Thr Val Cys Ser Val Arg Tyr
        100                 105                 110 act cgt ggg agc ttt cta tgc cct ggg gct cag cca ttt cca cac cgc    922
Thr Arg Gly Ser Phe Leu Cys Pro Gly Ala Gln Pro Phe Pro His Arg
    115                 120                 125 aac ttc tgt gag gag gta gct gtc ctt gat ggc cat ttc agt aaa ctt    970
Asn Phe Cys Glu Glu Val Ala Val Leu Asp Gly His Phe Ser Lys Leu
130                 135                 140                 145 ggt ttg aac agt gtg gca tat gtg atg ggt ggt ctt gac aaa act cag    1018
Gly Leu Asn Ser Val Ala Tyr Val Met Gly Gly Leu Asp Lys Thr Gln
                150                 155                 160 aaa tgg cat gtt tac tct gcc tct gcc gat ata gag agc cat tct ggc    1066
Lys Trp His Val Tyr Ser Ala Ser Ala Asp Ile Glu Ser His Ser Gly
            165                 170                 175 cct gtt tac act ctg gaa atg tgc atg act ggt ttg gcc agg aaa caa    1114
Pro Val Tyr Thr Leu Glu Met Cys Met Thr Gly Leu Gly Arg Lys Gln
        180                 185                 190 gca tct gtt ttc tac aaa aca cat tcc agt tca gct gct gcg atg act    1162
Ala Ser Val Phe Tyr Lys Thr His Ser Ser Ser Ala Ala Ala Met Thr
    195                 200                 205 gag gat tcc ggc ata agg aaa atc ctt cca cag tct gag atc tgt gat    1210
Glu Asp Ser Gly Ile Arg Lys Ile Leu Pro Gln Ser Glu Ile Cys Asp
210                 215                 220                 225 ttt gat ttt gac cct tgt ggt tac tct atg aat gcc att gaa ggg agt    1258
Phe Asp Phe Asp Pro Cys Gly Tyr Ser Met Asn Ala Ile Glu Gly Ser
                230                 235                 240 gca att tcc aca atc cac gtc act cca gaa gat ggt ttc agc tat gca    1306
Ala Ile Ser Thr Ile His Val Thr Pro Glu Asp Gly Phe Ser Tyr Ala
            245                 250                 255 agt ttt gag gct gtg ggc tat gat ctt caa gat ttg aat ttg agt cag    1354
Ser Phe Glu Ala Val Gly Tyr Asp Leu Gln Asp Leu Asn Leu Ser Gln
        260                 265                 270 ctg ctt gaa agg gtt ttg gct tgc ttt gaa ccg acc gag ttc tcc gtt    1402
Leu Leu Glu Arg Val Leu Ala Cys Phe Glu Pro Thr Glu Phe Ser Val
    275                 280                 285 gct ttg cat tct aat atc aag ggt gcc gaa ctt cga gca aag ttt ccc    1450
Ala Leu His Ser Asn Ile Lys Gly Ala Glu Leu Arg Ala Lys Phe Pro
290                 295                 300                 305 ctg gat gtg gaa ggt tac tct ggt gga gga ggg aac tat gaa atg ctt    1498
Leu Asp Val Glu Gly Tyr Ser Gly Gly Gly Gly Asn Tyr Glu Met Leu
                310                 315                 320 ggg aaa gga gga tcg atc atc tac cac agc ttt gca agg act gga ggc    1546
Gly Lys Gly Gly Ser Ile Ile Tyr His Ser Phe Ala Arg Thr Gly Gly
            325                 330                 335 agt gca tct ccc agg tct atc ctg aaa tgt tgt tgg agt gag gat gag    1594
Ser Ala Ser Pro Arg Ser Ile Leu Lys Cys Cys Trp Ser Glu Asp Glu
        340                 345                 350 aag gac gag gaa gct gaa gag aag tagttctttt cagctatttg ttttttcctt    1648
Lys Asp Glu Glu Ala Glu Glu Lys
355                 360 ttatttttc cttgaataaa tttcatgggg ttatgattct gagttcttag aggcatttgt    1708
ccatgccttg tgtctttcat tatcaattta gttttgactt tggattaata aaggggtttg    1768
tgttatcag                                                            1777
```

```
<210> SEQ ID NO 4
<211> LENGTH: 361
<212> TYPE: PRT
<213> ORGANISM: Populus deltoides

<400> SEQUENCE: 4

Met Ala Leu Pro Val Ser Ala Ile Gly Phe Glu Gly Tyr Glu Lys Arg
 1               5                  10                  15

Leu Glu Ile Ser Phe Leu Glu Pro Gly Phe Ser Asp Pro Glu Gly
            20                  25                  30

Lys Gly Leu Arg Ser Leu Ser Lys Ala Gln Leu Asp Glu Ile Leu Arg
        35                  40                  45

Pro Ala Glu Cys Thr Ile Val Asp Ser Leu Ser Asn Asp Gln Val Asp
    50                  55                  60

Ser Tyr Val Leu Ser Glu Ser Ser Leu Phe Val Tyr Pro Tyr Lys Val
65                  70                  75                  80

Ile Ile Lys Thr Cys Gly Thr Thr Lys Leu Leu Leu Ser Ile Pro Val
                85                  90                  95

Ile Leu Lys Leu Ala Asp Ala Leu Ser Leu Thr Val Cys Ser Val Arg
            100                 105                 110

Tyr Thr Arg Gly Ser Phe Leu Cys Pro Gly Ala Gln Pro Phe Pro His
        115                 120                 125

Arg Asn Phe Cys Glu Glu Val Ala Val Leu Asp Gly His Phe Ser Lys
    130                 135                 140

Leu Gly Leu Asn Ser Val Ala Tyr Val Met Gly Gly Leu Asp Lys Thr
145                 150                 155                 160

Gln Lys Trp His Val Tyr Ser Ala Ser Ala Asp Ile Glu Ser His Ser
                165                 170                 175

Gly Pro Val Tyr Thr Leu Glu Met Cys Met Thr Gly Leu Gly Arg Lys
            180                 185                 190

Gln Ala Ser Val Phe Tyr Lys Thr His Ser Ser Ser Ala Ala Ala Met
        195                 200                 205

Thr Glu Asp Ser Gly Ile Arg Lys Ile Leu Pro Gln Ser Glu Ile Cys
    210                 215                 220

Asp Phe Asp Phe Asp Pro Cys Gly Tyr Ser Met Asn Ala Ile Glu Gly
225                 230                 235                 240

Ser Ala Ile Ser Thr Ile His Val Thr Pro Glu Asp Gly Phe Ser Tyr
                245                 250                 255

Ala Ser Phe Glu Ala Val Gly Tyr Asp Leu Gln Asp Leu Asn Leu Ser
            260                 265                 270

Gln Leu Leu Glu Arg Val Leu Ala Cys Phe Glu Pro Thr Glu Phe Ser
        275                 280                 285

Val Ala Leu His Ser Asn Ile Lys Gly Ala Glu Leu Arg Ala Lys Phe
    290                 295                 300

Pro Leu Asp Val Glu Gly Tyr Ser Gly Gly Gly Asn Tyr Glu Met
305                 310                 315                 320

Leu Gly Lys Gly Gly Ser Ile Ile Tyr His Ser Phe Ala Arg Thr Gly
                325                 330                 335

Gly Ser Ala Ser Pro Arg Ser Ile Leu Lys Cys Cys Trp Ser Glu Asp
            340                 345                 350

Glu Lys Asp Glu Glu Ala Glu Glu Lys
        355                 360

<210> SEQ ID NO 5
<211> LENGTH: 1763
<212> TYPE: DNA
```

-continued

```
<213> ORGANISM: Populus deltoides
<220> FEATURE:
<221> NAME/KEY: CDS
<222> LOCATION: (548)..(1621)

<400> SEQUENCE: 5
acaaacaaga acccttcacg ttctttaaca atcttgcaga tttaagctct taaaaatctc    60
tctcttcaaa aacaaatcta gagtttgttg attttgtcat tggttttgcc ctttttttt   120 ctataaaaaa ccaatcttga tttgtttctt gaacagagtt tagtttggag tttgagaaag   180
agggagtttt tgaaggagat taattttca agatttcata taattattg acaagactga   240 atgatccatg gagtctaaag gtggcaagaa gtctagtagt agtagtagta gtagtaaatc   300
cttattgtac gaagcacctc tcggctacag cattgaagac atcagacctg ccggtggaat   360
caagaagttc cgatctgctg cttactccaa ctgcgttcgg aagccatcct gagattttcc   420
aagtgttgag ataacccctt tttagctttt tcatactgtc tgttgtcctt agtcttttt   480 tcttttctgc tttcctcgtt ctctcgcact cttttctgca attgtcatct gtttactgtg   540 aggtgag atg gca ctg ccg gtc tct gca atc gga ttt gaa ggt tac gaa     589
        Met Ala Leu Pro Val Ser Ala Ile Gly Phe Glu Gly Tyr Glu
          1               5                  10 aaa agg ctt gaa att tgc ttt tta gag cct ggc ttc ttt tct gac cct    637
Lys Arg Leu Glu Ile Cys Phe Leu Glu Pro Gly Phe Phe Ser Asp Pro
 15                  20                  25                  30 gaa gga aag ggc ctc agg tct ttg tcc aag gct caa ttg gac gag att    685
Glu Gly Lys Gly Leu Arg Ser Leu Ser Lys Ala Gln Leu Asp Glu Ile
                 35                  40                  45 ctc aaa cca gct gaa tgc act ata gtt gat tcg ctt tca aat gac gag    733
Leu Lys Pro Ala Glu Cys Thr Ile Val Asp Ser Leu Ser Asn Asp Glu
             50                  55                  60 gtt gat tcg tat gtt ctg tcg gaa tcc agt ctc ttt gta tac cct tac    781
Val Asp Ser Tyr Val Leu Ser Glu Ser Ser Leu Phe Val Tyr Pro Tyr
 65                  70                  75 aaa gtt atc atc aaa act tgt ggg act acc aaa ctg ctt ctt tcg atc    829
Lys Val Ile Ile Lys Thr Cys Gly Thr Thr Lys Leu Leu Leu Ser Ile
             80                  85                  90 cca gtg atc ctt gag ctc gct gat gcc ctt tca ctc act gta tgt tct    877
Pro Val Ile Leu Glu Leu Ala Asp Ala Leu Ser Leu Thr Val Cys Ser
 95                 100                 105                 110 gtg agg tat act cgt ggg agc ttc ata tgt ccc ggg gcg cag cca ttt    925
Val Arg Tyr Thr Arg Gly Ser Phe Ile Cys Pro Gly Ala Gln Pro Phe
                115                 120                 125 ccg cat cgt aac ttc tgt gag gag gta act gtc ctc gat ggc cat ttc    973
Pro His Arg Asn Phe Cys Glu Glu Val Thr Val Leu Asp Gly His Phe
            130                 135                 140 agt aaa ttt ggt tta gag agt gtg gca tat gtg atg gga agt ccc aac   1021
Ser Lys Phe Gly Leu Glu Ser Val Ala Tyr Val Met Gly Ser Pro Asn
145                 150                 155 tca act cag aaa tgg cat gtt tac tct gct gct gct ggt gtg aag agc   1069
Ser Thr Gln Lys Trp His Val Tyr Ser Ala Ala Ala Gly Val Lys Ser
            160                 165                 170 cat tct ggc cct gtt tac act ctg gaa atg tgc atg act ggt ttg gac   1117
His Ser Gly Pro Val Tyr Thr Leu Glu Met Cys Met Thr Gly Leu Asp
175                 180                 185                 190 agg aag cga gca tct gtt ttc tac aaa aca cac gcc agt tca gct act   1165
Arg Lys Arg Ala Ser Val Phe Tyr Lys Thr His Ala Ser Ser Ala Thr
                195                 200                 205 gtt atg act gag gat tct ggt ata agg aag atc ctt ccg caa tct gag   1213
Val Met Thr Glu Asp Ser Gly Ile Arg Lys Ile Leu Pro Gln Ser Glu
            210                 215                 220
```

```
atc tgc gat ttt gat ttt gac cct tgt ggt tac tct atg aat gcc att    1261
Ile Cys Asp Phe Asp Phe Asp Pro Cys Gly Tyr Ser Met Asn Ala Ile
        225                 230                 235 gaa ggg agt gca att tcc aca atc cat gtc acc cca gaa gat ggt ttc    1309
Glu Gly Ser Ala Ile Ser Thr Ile His Val Thr Pro Glu Asp Gly Phe
    240                 245                 250 agc tat gca agt ttt gag gct gtg ggt tat gat ttt caa gaa tta aat    1357
Ser Tyr Ala Ser Phe Glu Ala Val Gly Tyr Asp Phe Gln Glu Leu Asn
255                 260                 265                 270 ttg aag cag ctc ctt tat agg gtt ttg gtt tgc ttt gaa ccg acc gag    1405
Leu Lys Gln Leu Leu Tyr Arg Val Leu Val Cys Phe Glu Pro Thr Glu
                275                 280                 285 ttc tcc att gcg ttg cat tct aat gtt gag tgt gac gaa ctt gga gcg    1453
Phe Ser Ile Ala Leu His Ser Asn Val Glu Cys Asp Glu Leu Gly Ala
            290                 295                 300 atg ttt tcc ctg gat gtg aaa ggt tac tct tgt gga ggg ggg aac tat    1501
Met Phe Ser Leu Asp Val Lys Gly Tyr Ser Cys Gly Gly Gly Asn Tyr
        305                 310                 315 gaa atg ctc ggg aag ggt gga tcg att gtc tac cac agc ttt gca gcg    1549
Glu Met Leu Gly Lys Gly Gly Ser Ile Val Tyr His Ser Phe Ala Ala
    320                 325                 330 act gga ggc tgc tca tct ccc agg tca atc ctg aaa tgt tgt tgg agt    1597
Thr Gly Gly Cys Ser Ser Pro Arg Ser Ile Leu Lys Cys Cys Trp Ser
335                 340                 345                 350 gag gac gag gaa gct gaa gag aag tagttctttt cagcaatgtg ttttttcttt   1651
Glu Asp Glu Glu Ala Glu Glu Lys
                355 ttcttttctt ttttgtgttt agttgttgat gtcatggggt tatgattctg agttttagag   1711 gcatttgtcc atgccttgag tctttcatta caatttatct catgtcttgt tc           1763

<210> SEQ ID NO 6
<211> LENGTH: 358
<212> TYPE: PRT
<213> ORGANISM: Populus deltoides

<400> SEQUENCE: 6

Met Ala Leu Pro Val Ser Ala Ile Gly Phe Glu Gly Tyr Glu Lys Arg
1               5                   10                  15

Leu Glu Ile Cys Phe Leu Glu Pro Gly Phe Ser Asp Pro Glu Gly
            20                  25                  30

Lys Gly Leu Arg Ser Leu Ser Lys Ala Gln Leu Asp Glu Ile Leu Lys
        35                  40                  45

Pro Ala Glu Cys Thr Ile Val Asp Ser Leu Ser Asn Asp Glu Val Asp
    50                  55                  60

Ser Tyr Val Leu Ser Glu Ser Ser Leu Phe Val Tyr Pro Tyr Lys Val
65                  70                  75                  80

Ile Ile Lys Thr Cys Gly Thr Thr Lys Leu Leu Leu Ser Ile Pro Val
                85                  90                  95

Ile Leu Glu Leu Ala Asp Ala Leu Ser Leu Thr Val Cys Ser Val Arg
            100                 105                 110

Tyr Thr Arg Gly Ser Phe Ile Cys Pro Gly Ala Gln Pro Phe Pro His
        115                 120                 125

Arg Asn Phe Cys Glu Glu Val Thr Val Leu Asp Gly His Phe Ser Lys
    130                 135                 140

Phe Gly Leu Glu Ser Val Ala Tyr Val Met Gly Ser Pro Asn Ser Thr
145                 150                 155                 160

Gln Lys Trp His Val Tyr Ser Ala Ala Ala Gly Val Lys Ser His Ser
```

```
                    165                 170                 175
Gly Pro Val Tyr Thr Leu Glu Met Cys Met Thr Gly Leu Asp Arg Lys
            180                 185                 190

Arg Ala Ser Val Phe Tyr Lys Thr His Ala Ser Ser Ala Thr Val Met
        195                 200                 205

Thr Glu Asp Ser Gly Ile Arg Lys Ile Leu Pro Gln Ser Glu Ile Cys
    210                 215                 220

Asp Phe Asp Phe Asp Pro Cys Gly Tyr Ser Met Asn Ala Ile Glu Gly
225                 230                 235                 240

Ser Ala Ile Ser Thr Ile His Val Thr Pro Glu Asp Gly Phe Ser Tyr
                245                 250                 255

Ala Ser Phe Glu Ala Val Gly Tyr Asp Phe Gln Glu Leu Asn Leu Lys
            260                 265                 270

Gln Leu Leu Tyr Arg Val Leu Val Cys Phe Glu Pro Thr Glu Phe Ser
        275                 280                 285

Ile Ala Leu His Ser Asn Val Glu Cys Asp Glu Leu Gly Ala Met Phe
    290                 295                 300

Ser Leu Asp Val Lys Gly Tyr Ser Cys Gly Gly Gly Asn Tyr Glu Met
305                 310                 315                 320

Leu Gly Lys Gly Gly Ser Ile Val Tyr His Ser Phe Ala Ala Thr Gly
                325                 330                 335

Gly Cys Ser Ser Pro Arg Ser Ile Leu Lys Cys Cys Trp Ser Glu Asp
            340                 345                 350

Glu Glu Ala Glu Glu Lys
        355

<210> SEQ ID NO 7
<211> LENGTH: 2523
<212> TYPE: DNA
<213> ORGANISM: Populus deltoides
<220> FEATURE:
<221> NAME/KEY: CDS
<222> LOCATION: (1283)..(2365)
<220> FEATURE:
<221> NAME/KEY: modified_base
<222> LOCATION: (339)
<223> OTHER INFORMATION: a, c, t, g, unknown or other

<400> SEQUENCE: 7
ttaaccctat atttctctca gaactcacat aaaaaatatt gcgagtttag ggtcataaaa      60
atctctatca tcacaaacaa atatagggtt tgttgatttg gtggctgttt tcgccgtctt     120
tgctttcaaa attcaatctt gacctgtttc ttttatgctt tttgaatagg taatatatac     180
attgtttgtt ttgcttgctt tggttttgta atctggtgat cttgtttaat tcttttttggc    240 tttggtttgt aggttttttt ttttgaacyt gagaaagagg ggggttttca arggagacta    300
gcttttcaag awttgatata ttttattggt aagttttttnt tttccgtttt ttggtaatag    360
ttgcatggat tcttggtgta gatgttgatt tggacttgtt tttgtattgt tgtcctttat    420
gttttatgtg tatgttaatt gttctgatcc ttgatataat gtaaatctga ggcttttatt    480
tttatggatt cgttaaggtg tatggacttg gtttatggtt ttggtcttga aaaaaaaatt    540
aggcttagca agttttcttc tgagaataac ttattttatt ttattattta aaattaaatg    600
gtgtttggga atttgaattc tttctctttg gtattttttc tatccttgtg aatctgtttta   660 gtcttttaaa ttcaatattt tattttattt tacttatgat ttggtgattg attagttatt    720
tttgtagctt gtattgtctg ttgattttta atctccaata tgtcttactt ctcagttttt    780
ttcaatttgc tattggaatt tgctattat ttttaagatt gtagactagt ttgctttgag    840
```

```
ttttgtgcta attgcaatcc ttcttgtgtg attcttacag gactgaatga tctaatggag      900
tctaaaggtg gcaagaagaa gtctagtagt agtagtagta gtaaatcctt atgttacgaa      960
gctcccctcg gttacagcat tgaagacctc agacctgctg gtggaatcaa gaagttcaga    1020
tctgctgcat actccaacgt gagtttgaag ttaatcgatc tgttttcct ttggcatttc      1080 attgtgcgac tggtttccta atcttgtgtc atgtttattt gtgcagtgcg ttcgaaaacc    1140
atcctgagat tttccaagtg ttgacataac cccattttag ctatttcgca cgctcagttg    1200
tctttaktct gttttctgt tctgctttcc tcgttctctt gtactctttg ctgcactttt      1260
catttgttga ctgtgaggtc ag atg gcg ctg cca gtc tct gca atc gga ttt     1312
                         Met Ala Leu Pro Val Ser Ala Ile Gly Phe
                          1               5                  10 gaa ggt tac gaa aaa agg ctt gaa ata tct ttc cta gag cct ggc ttc      1360
Glu Gly Tyr Glu Lys Arg Leu Glu Ile Ser Phe Leu Glu Pro Gly Phe
                15                  20                  25 ttt tct gac cct gaa ggg aag ggc ctg agg tct ttg tcc aag gct caa      1408
Phe Ser Asp Pro Glu Gly Lys Gly Leu Arg Ser Leu Ser Lys Ala Gln
        30                  35                  40 ttg gac gag att ctc aga cca gct gaa tgt act att gtt gat tcg cta      1456
Leu Asp Glu Ile Leu Arg Pro Ala Glu Cys Thr Ile Val Asp Ser Leu
    45                  50                  55 tca aat gac cag gtt gat tct tat gtc ctg tcg gaa tcc agt ctc ttt      1504
Ser Asn Asp Gln Val Asp Ser Tyr Val Leu Ser Glu Ser Ser Leu Phe
60                  65                  70 gtg tac cct tac aaa gtt att atc aaa aca tgt ggg act acc aaa ctg      1552
Val Tyr Pro Tyr Lys Val Ile Ile Lys Thr Cys Gly Thr Thr Lys Leu
 75                  80                  85                  90 ctt ctc tcg ata ccg gtg att ctt aag ctc gct gat gcc ctt tca ctc      1600
Leu Leu Ser Ile Pro Val Ile Leu Lys Leu Ala Asp Ala Leu Ser Leu
                95                 100                 105 act gta tgt tct gtg agg tat act cgt ggg agc ttt cta tgc cct ggg      1648
Thr Val Cys Ser Val Arg Tyr Thr Arg Gly Ser Phe Leu Cys Pro Gly
            110                 115                 120 gct cag cca ttt cca cac cgc aac ttc tgt gag gag gta gct gtc ctt      1696
Ala Gln Pro Phe Pro His Arg Asn Phe Cys Glu Glu Val Ala Val Leu
        125                 130                 135 gac gat cac ttc agt aaa ctt ggt tta aac agt gtg gca tat gtg atg      1744
Asp Asp His Phe Ser Lys Leu Gly Leu Asn Ser Val Ala Tyr Val Met
    140                 145                 150 ggt ggt ctt gac aaa act cag aaa tgg cat gtt tac tct gcc tct gcc      1792
Gly Gly Leu Asp Lys Thr Gln Lys Trp His Val Tyr Ser Ala Ser Ala
155                 160                 165                 170 gat ata gag agc cat tct ggc cct gtt tac act ctg gaa atg tgc atg      1840
Asp Ile Glu Ser His Ser Gly Pro Val Tyr Thr Leu Glu Met Cys Met
                175                 180                 185 act ggt ttg ggc agg aaa caa gca tct gtt ttc tac aaa aca cat tcc      1888
Thr Gly Leu Gly Arg Lys Gln Ala Ser Val Phe Tyr Lys Thr His Ser
            190                 195                 200 agt tca gct gct gcg atg act gag gat tcc ggt ata agg aaa atc ctt      1936
Ser Ser Ala Ala Ala Met Thr Glu Asp Ser Gly Ile Arg Lys Ile Leu
        205                 210                 215 cca cag tct gag atc tgt gat ttt gat ttt gac cca tgt ggt tac tct      1984
Pro Gln Ser Glu Ile Cys Asp Phe Asp Phe Asp Pro Cys Gly Tyr Ser
    220                 225                 230 atg aat gcc att gaa ggg agt gca att tcc aca atc cac gtc act cca      2032
Met Asn Ala Ile Glu Gly Ser Ala Ile Ser Thr Ile His Val Thr Pro
235                 240                 245                 250 gaa gat ggt ttc agc tat gca agt ttt gag gct gtg ggc tat gat ctt      2080
Glu Asp Gly Phe Ser Tyr Ala Ser Phe Glu Ala Val Gly Tyr Asp Leu
```

-continued

| | | | | | | | | | | | | | | | |
|---|---|---|---|---|---|---|---|---|---|---|---|---|---|---|---|
| | Glu | Asp | Gly | Phe | Ser | Tyr | Ala | Ser | Phe | Glu | Ala | Val | Gly | Tyr | Asp | Leu |
| | | | | 255 | | | | 260 | | | | 265 | | | |

```
caa gat ttg aat ttg agt cgg ctg ctt gaa agg gtc ttg gct tgc ttt      2128
Gln Asp Leu Asn Leu Ser Arg Leu Leu Glu Arg Val Leu Ala Cys Phe
        270                 275                 280 gaa ccg acc atg ttc tcc gtt gcc ttg cat tct aat atc aag ggt gcc      2176
Glu Pro Thr Met Phe Ser Val Ala Leu His Ser Asn Ile Lys Gly Ala
            285                 290                 295 gaa ctt aga gca aag ttt ccc ctg gac gtg gaa ggt tac tct ggc gga      2224
Glu Leu Arg Ala Lys Phe Pro Leu Asp Val Glu Gly Tyr Ser Gly Gly
    300                 305                 310 gga ggg aac tat gaa atg ctt ggg aaa ggt gga tcg atc atc tac cac      2272
Gly Gly Asn Tyr Glu Met Leu Gly Lys Gly Gly Ser Ile Ile Tyr His
315                 320                 325                 330 agc ttt gca agg act gga ggc agt gca tct ccc agg tct atc ctg aaa      2320
Ser Phe Ala Arg Thr Gly Gly Ser Ala Ser Pro Arg Ser Ile Leu Lys
            335                 340                 345 tgt tgt tgg agt gag gat gag aag gac gag gaa gct gaa gag aag          2365
Cys Cys Trp Ser Glu Asp Glu Lys Asp Glu Glu Ala Glu Glu Lys
        350                 355                 360 tagttctttt cagctatttg ttttttcctt ttattttttc cttgaataaa tgtcatgggg    2425
ttatgattct gagttcttga ggcatttgtc catgcctcgt gtctttcatt atcgatttag    2485
ttttgacttc ggattaataa aggggtttgt gttatcag                            2523

<210> SEQ ID NO 8
<211> LENGTH: 361
<212> TYPE: PRT
<213> ORGANISM: Populus deltoides

<400> SEQUENCE: 8

Met Ala Leu Pro Val Ser Ala Ile Gly Phe Glu Gly Tyr Glu Lys Arg
  1               5                  10                  15

Leu Glu Ile Ser Phe Leu Glu Pro Gly Phe Ser Asp Pro Glu Gly
            20                  25                  30

Lys Gly Leu Arg Ser Leu Ser Lys Ala Gln Leu Asp Glu Ile Leu Arg
        35                  40                  45

Pro Ala Glu Cys Thr Ile Val Asp Ser Leu Ser Asn Asp Gln Val Asp
    50                  55                  60

Ser Tyr Val Leu Ser Glu Ser Leu Phe Val Tyr Pro Tyr Lys Val
 65                  70                  75                  80

Ile Ile Lys Thr Cys Gly Thr Thr Lys Leu Leu Leu Ser Ile Pro Val
                85                  90                  95

Ile Leu Lys Leu Ala Asp Ala Leu Ser Leu Thr Val Cys Ser Val Arg
            100                 105                 110

Tyr Thr Arg Gly Ser Phe Leu Cys Pro Gly Ala Gln Pro Phe Pro His
        115                 120                 125

Arg Asn Phe Cys Glu Glu Val Ala Val Leu Asp His Phe Ser Lys
    130                 135                 140

Leu Gly Leu Asn Ser Val Ala Tyr Val Met Gly Gly Leu Asp Lys Thr
145                 150                 155                 160

Gln Lys Trp His Val Tyr Ser Ala Ser Ala Asp Ile Glu Ser His Ser
                165                 170                 175

Gly Pro Val Tyr Thr Leu Glu Met Cys Met Thr Gly Leu Gly Arg Lys
            180                 185                 190

Gln Ala Ser Val Phe Tyr Lys Thr His Ser Ser Ser Ala Ala Ala Met
        195                 200                 205
```

```
Thr Glu Asp Ser Gly Ile Arg Lys Ile Leu Pro Gln Ser Glu Ile Cys
        210                 215                 220
Asp Phe Asp Phe Asp Pro Cys Gly Tyr Ser Met Asn Ala Ile Glu Gly
225                 230                 235                 240
Ser Ala Ile Ser Thr Ile His Val Thr Pro Glu Asp Gly Phe Ser Tyr
            245                 250                 255
Ala Ser Phe Glu Ala Val Gly Tyr Asp Leu Gln Asp Leu Asn Leu Ser
        260                 265                 270
Arg Leu Leu Glu Arg Val Leu Ala Cys Phe Glu Pro Thr Met Phe Ser
    275                 280                 285
Val Ala Leu His Ser Asn Ile Lys Gly Ala Glu Leu Arg Ala Lys Phe
290                 295                 300
Pro Leu Asp Val Glu Gly Tyr Ser Gly Gly Gly Asn Tyr Glu Met
305                 310                 315                 320
Leu Gly Lys Gly Gly Ser Ile Ile Tyr His Ser Phe Ala Arg Thr Gly
            325                 330                 335
Gly Ser Ala Ser Pro Arg Ser Ile Leu Lys Cys Cys Trp Ser Glu Asp
        340                 345                 350
Glu Lys Asp Glu Glu Ala Glu Glu Lys
        355                 360
```

<210> SEQ ID NO 9
<211> LENGTH: 1878
<212> TYPE: DNA
<213> ORGANISM: Arabidopsis thaliana
<220> FEATURE:
<221> NAME/KEY: CDS
<222> LOCATION: (540)..(1637)

<400> SEQUENCE: 9

```
gaacgcatct cattgcttca tcattaccaa atcatcaact taatcgtttc tctcaaattt      60
agggttttct cttttctcga aagtcttgcg gttttctgaa tcatctctat ctggtttgag     120
ggtttcgttt gatatctgga gaaagggggtt tctggaaaca aggagttcat aattcgcgat    180
cttgatctat cgatcttcat ttatatataa aagcgtgaat gagattatga tggagtcgaa    240
aggtggtaaa aagaagtcca gcagtagtag ttccttattt tacgaagctc ccctcggtta    300
cagcattgaa gacgttcgtc caaacggtgg aatcaagaaa ttcaaatctt ctgtctactc    360
aaactgctcc aagaggccat cctgagtacc agcgtgcacc gatcttcata atatagttat    420
agctttcttt actttccagt ttataatttt cttcttcaa agctccttt ctgctggttc      480 ccggatccaa tcgttctctc ctcctactac aagtcctgtc gctcacacaa caaggcgag    539 atg gcc tta tct gca atc ggt ttc gaa ggt tac gag aaa cgg ctc gag    587
Met Ala Leu Ser Ala Ile Gly Phe Glu Gly Tyr Glu Lys Arg Leu Glu
  1               5                  10                  15 gtg act ttc ttt gag cca agc atc ttt caa gac tcc aag gga ctg gga    635
Val Thr Phe Phe Glu Pro Ser Ile Phe Gln Asp Ser Lys Gly Leu Gly
             20                  25                  30 ctc cgt gct ctg acc aag tcc cag ctt gat gaa att ctt aca cct gct    683
Leu Arg Ala Leu Thr Lys Ser Gln Leu Asp Glu Ile Leu Thr Pro Ala
         35                  40                  45 gca tgc acg atc gtt tca tct ctc tcc aac gat caa ttg gac tct tac    731
Ala Cys Thr Ile Val Ser Ser Leu Ser Asn Asp Gln Leu Asp Ser Tyr
     50                  55                  60 gta ctc tct gag tcc agc ttc ttt gtc tac ccc tac aaa gtc atc atc    779
Val Leu Ser Glu Ser Ser Phe Phe Val Tyr Pro Tyr Lys Val Ile Ile
 65                  70                  75                  80 aag act tgc ggt acc act aag ctc ctc ctc tct atc cca cca ctt cta    827
```

```
                Lys Thr Cys Gly Thr Thr Lys Leu Leu Leu Ser Ile Pro Pro Leu Leu
                                85                  90                  95 aag ctg gct ggt gag ctc tct ctg agt gtc aag tct gtg aag tac act             875
Lys Leu Ala Gly Glu Leu Ser Leu Ser Val Lys Ser Val Lys Tyr Thr
            100                 105                 110 cgc ggc tcc ttc ctc tgc ccc gga ggc cag cct ttt cct cac cgc agc             923
Arg Gly Ser Phe Leu Cys Pro Gly Gly Gln Pro Phe Pro His Arg Ser
            115                 120                 125 ttc tct gaa gaa gtc tct gtt ctt gat ggg cac ttt act cag ctg ggc             971
Phe Ser Glu Glu Val Ser Val Leu Asp Gly His Phe Thr Gln Leu Gly
        130                 135                 140 ttg aac agc gta gcc tac ttg atg ggc aat gat gat gag act aag aaa            1019
Leu Asn Ser Val Ala Tyr Leu Met Gly Asn Asp Asp Glu Thr Lys Lys
145                 150                 155                 160 tgg cat gtc tat gct gcc tct gcc cag gac tcc agc aac tgc aac aac            1067
Trp His Val Tyr Ala Ala Ser Ala Gln Asp Ser Ser Asn Cys Asn Asn
                165                 170                 175 aat gtc tac act ctc gag atg tgc atg act ggt ctg gac aga gag aaa            1115
Asn Val Tyr Thr Leu Glu Met Cys Met Thr Gly Leu Asp Arg Glu Lys
                180                 185                 190 gct gct gtc ttc tac aag gat gaa gct gac aag act ggg tca atg act            1163
Ala Ala Val Phe Tyr Lys Asp Glu Ala Asp Lys Thr Gly Ser Met Thr
            195                 200                 205 gat aac tct gga atc aga aag atc ctt ccc aag tct gag atc tgc gac            1211
Asp Asn Ser Gly Ile Arg Lys Ile Leu Pro Lys Ser Glu Ile Cys Asp
        210                 215                 220 ttt gaa ttc gag ccc tgc ggc tac tct atg aac tca att gaa ggg gat            1259
Phe Glu Phe Glu Pro Cys Gly Tyr Ser Met Asn Ser Ile Glu Gly Asp
225                 230                 235                 240 gca atc tcc acg atc cat gtg acc cct gaa gat ggg ttt agc tac gct            1307
Ala Ile Ser Thr Ile His Val Thr Pro Glu Asp Gly Phe Ser Tyr Ala
                245                 250                 255 agc ttc gaa gct gtg ggt tac gac ttc aac acc ctt gac ctt agc cag            1355
Ser Phe Glu Ala Val Gly Tyr Asp Phe Asn Thr Leu Asp Leu Ser Gln
                260                 265                 270 ctg gtg aca agg gtt ctc tct tgc ttc gag ccc aag caa ttc tct gta            1403
Leu Val Thr Arg Val Leu Ser Cys Phe Glu Pro Lys Gln Phe Ser Val
            275                 280                 285 gct gtg cac tcg agc gtt gga gcg aac tca tac aag cca gag att act            1451
Ala Val His Ser Ser Val Gly Ala Asn Ser Tyr Lys Pro Glu Ile Thr
        290                 295                 300 gta gac ttg gaa gac tat ggg tgc aga gag agg aca ttt gag tct cta            1499
Val Asp Leu Glu Asp Tyr Gly Cys Arg Glu Arg Thr Phe Glu Ser Leu
305                 310                 315                 320 gga gaa gag agt gga aca gtg atg tat cag acg ttt gag aag ctt ggt            1547
Gly Glu Glu Ser Gly Thr Val Met Tyr Gln Thr Phe Glu Lys Leu Gly
                325                 330                 335 aag tac tgt gga tcg cct aga tct acc ttg aag tgt gaa tgg agc agc            1595
Lys Tyr Cys Gly Ser Pro Arg Ser Thr Leu Lys Cys Glu Trp Ser Ser
                340                 345                 350 aac aat agc tgc agc agc gag gac gag aag gac gag gga atc                    1637
Asn Asn Ser Cys Ser Ser Glu Asp Glu Lys Asp Glu Gly Ile
            355                 360                 365 tagcagaatt tttcttccta ataactattt tcgagctttc tgttttgtt ctttcttttt           1697 aaaaaactta ttaagttctt atgaataatg acttgtgaag tttgagttcg tctccttcac          1757
aagcaagttg tattggtgtt ttctacttta tgaatatggg ttttatatac ctaaagactt          1817
gttatgttat tattcttaaa tgttgctgct atgatgatta ctattatcga tttttactaa          1877
a                                                                          1878
```

<210> SEQ ID NO 10
<211> LENGTH: 366
<212> TYPE: PRT
<213> ORGANISM: Arabidopsis thaliana

<400> SEQUENCE: 10

Met Ala Leu Ser Ala Ile Gly Phe Glu Gly Tyr Glu Lys Arg Leu Glu
1               5                   10                  15

Val Thr Phe Phe Glu Pro Ser Ile Phe Gln Asp Ser Lys Gly Leu Gly
            20                  25                  30

Leu Arg Ala Leu Thr Lys Ser Gln Leu Asp Glu Ile Leu Thr Pro Ala
        35                  40                  45

Ala Cys Thr Ile Val Ser Ser Leu Ser Asn Asp Gln Leu Asp Ser Tyr
    50                  55                  60

Val Leu Ser Glu Ser Ser Phe Phe Val Tyr Pro Tyr Lys Val Ile Ile
65                  70                  75                  80

Lys Thr Cys Gly Thr Thr Lys Leu Leu Leu Ser Ile Pro Pro Leu Leu
                85                  90                  95

Lys Leu Ala Gly Glu Leu Ser Leu Ser Val Lys Ser Val Lys Tyr Thr
            100                 105                 110

Arg Gly Ser Phe Leu Cys Pro Gly Gly Gln Pro Phe Pro His Arg Ser
        115                 120                 125

Phe Ser Glu Glu Val Ser Val Leu Asp Gly His Phe Thr Gln Leu Gly
    130                 135                 140

Leu Asn Ser Val Ala Tyr Leu Met Gly Asn Asp Asp Glu Thr Lys Lys
145                 150                 155                 160

Trp His Val Tyr Ala Ala Ser Ala Gln Asp Ser Ser Asn Cys Asn Asn
                165                 170                 175

Asn Val Tyr Thr Leu Glu Met Cys Met Thr Gly Leu Asp Arg Glu Lys
            180                 185                 190

Ala Ala Val Phe Tyr Lys Asp Glu Ala Asp Lys Thr Gly Ser Met Thr
        195                 200                 205

Asp Asn Ser Gly Ile Arg Lys Ile Leu Pro Lys Ser Glu Ile Cys Asp
    210                 215                 220

Phe Glu Phe Glu Pro Cys Gly Tyr Ser Met Asn Ser Ile Glu Gly Asp
225                 230                 235                 240

Ala Ile Ser Thr Ile His Val Thr Pro Glu Asp Gly Phe Ser Tyr Ala
                245                 250                 255

Ser Phe Glu Ala Val Gly Tyr Asp Phe Asn Thr Leu Asp Leu Ser Gln
            260                 265                 270

Leu Val Thr Arg Val Leu Ser Cys Phe Glu Pro Lys Gln Phe Ser Val
        275                 280                 285

Ala Val His Ser Ser Val Gly Ala Asn Ser Tyr Lys Pro Glu Ile Thr
    290                 295                 300

Val Asp Leu Glu Asp Tyr Gly Cys Arg Glu Arg Thr Phe Glu Ser Leu
305                 310                 315                 320

Gly Glu Glu Ser Gly Thr Val Met Tyr Gln Thr Phe Glu Lys Leu Gly
                325                 330                 335

Lys Tyr Cys Gly Ser Pro Arg Ser Thr Leu Lys Cys Glu Trp Ser Ser
            340                 345                 350

Asn Asn Ser Cys Ser Ser Glu Asp Glu Lys Asp Glu Gly Ile
        355                 360                 365

<210> SEQ ID NO 11

<211> LENGTH: 795
<212> TYPE: DNA
<213> ORGANISM: Xanthomonas axonopodis
<220> FEATURE:
<221> NAME/KEY: CDS
<222> LOCATION: (1)

<212> TYPE: PRT
<213> ORGANISM: Xanthomonas axonopodis

<400> SEQUENCE: 12

Met Val Lys Pro Leu Pro Arg Leu Arg Leu Gln Gly Phe Asn Asn Leu
1               5                   10                  15

Thr Lys Ala Leu Ser Phe Asn Ile Tyr Asp Val Cys Tyr Ala Arg Thr
            20                  25                  30

Glu Glu Glu Arg Gln Arg Tyr Ile Glu Tyr Ile Asp Glu Gln Tyr Asp
        35                  40                  45

Ala Asp Arg Leu Thr Gln Ile Leu Thr Asp Val Ala Glu Ile Ile Gly
    50                  55                  60

Ala Asn Ile Leu Asn Ile Ala Arg Gln Asp Tyr Asp Pro Gln Gly Ala
65                  70                  75                  80

Ser Val Thr Ile Leu Ile Ser Glu Glu Pro Val Ile Asp Lys Lys Gln
                85                  90                  95

Ala Gly Lys Glu Leu Ile Ser Asp Ala Val Val Ala His Met Asp Lys
            100                 105                 110

Ser His Ile Thr Val His Thr Tyr Pro Glu Thr His Pro Gln Glu Gly
        115                 120                 125

Ile Ala Thr Phe Arg Ala Asp Ile Asp Val Ala Thr Cys Gly Val Ile
    130                 135                 140

Ser Pro Leu Lys Ala Leu Asn Tyr Leu Ile Glu Ser Leu Glu Ser Asp
145                 150                 155                 160

Ile Val Ile Met Asp Tyr Arg Val Arg Gly Phe Thr Arg Asp Val Lys
                165                 170                 175

Gly Lys Lys His Tyr Ile Asp His Lys Ile Asn Ser Ile Gln Gln Phe
            180                 185                 190

Leu Ala Lys Asn Val Lys Ser Arg Tyr Glu Met Phe Asp Val Asn Val
        195                 200                 205

Tyr Gln Glu Asn Ile Phe His Thr Lys Met His Leu Lys Asp Phe Asp
    210                 215                 220

Leu Asp Gln Tyr Leu Phe Glu Glu Arg Ala Lys Asn Leu Ser Phe Lys
225                 230                 235                 240

Glu Arg Met Lys Ile Glu Thr Leu Leu Lys Arg Glu Ile Glu Glu Leu
                245                 250                 255

Phe His Gly Arg Asn Leu Ser Glu
            260

<210> SEQ ID NO 13
<211> LENGTH: 1820
<212> TYPE: DNA
<213> ORGANISM: Datura stramonium
<220> FEATURE:
<221> NAME/KEY: CDS
<222> LOCATION: (491)..(1576)

<400> SEQUENCE: 13
cttgtatact cttccgaatc gccttctcca aatttctagg gtttctctct tcttcggaat 60
tttctggttt ggaaagatcg ttgtttattg gagataaatc ggatttggaa caaatttcaa 120
tttttaaata ttgtgaatga tctaatggag tcaaaaggtg ggaaaaagaa gtctagtagt 180
agttccttat tttacgaagc tcccctcggc tacagcattg aagacgttcg accaaacggt 240
ggagtgaaga agttcagatc tgctgcttac tccaactgcg cgcgcaaacc atcctgatat 300
tccctaaact tctgtcctta aagcgtcaat agacgcaacc aaaaaaaaca aaaaaaattt 360
ctgctttcaa tttctttcgt tgtcaagccc tcactccttt tcttccttct tttactactt 420

```
cctgctttgc actcgttgct ctgaacattt tctgctttaa cttcttttgc tgctgtgaac    480 tttttttcata atg gaa atg gac ttg cca gtc tct gcc atc ggt ttt gaa      529
           Met Glu Met Asp Leu Pro Val Ser Ala Ile Gly Phe Glu
             1               5                  10 ggt ttt gaa aag agg ctc gaa att tct ttt gtc gag cct ggt ctg ttt      577
Gly Phe Glu Lys Arg Leu Glu Ile Ser Phe Val Glu Pro Gly Leu Phe
         15                  20                  25 tct gat cct aat gga aaa gga ctt cga tct ctc tca aag gca cag ttg      625
Ser Asp Pro Asn Gly Lys Gly Leu Arg Ser Leu Ser Lys Ala Gln Leu
 30                  35                  40                  45 gat gaa att ctc gga cct gct gag tgc acc att gtc gat aac cta tca      673
Asp Glu Ile Leu Gly Pro Ala Glu Cys Thr Ile Val Asp Asn Leu Ser
                 50                  55                  60 aat gac tat gtt gat tcc tat gtc ctc tct gag tcg agc ctc ttc gtt      721
Asn Asp Tyr Val Asp Ser Tyr Val Leu Ser Glu Ser Ser Leu Phe Val
             65                  70                  75 tat tct tac aag ata atc att aaa aca tgt ggc acc aca aag ttg ctt      769
Tyr Ser Tyr Lys Ile Ile Ile Lys Thr Cys Gly Thr Thr Lys Leu Leu
         80                  85                  90 ctc gca att ccg ccc att cta agg ttg gct gag acc ttg tct ctc aaa      817
Leu Ala Ile Pro Pro Ile Leu Arg Leu Ala Glu Thr Leu Ser Leu Lys
     95                 100                 105 gta caa gat gtg agg tat acc cgt ggg agc ttc att ttc cct ggt gct      865
Val Gln Asp Val Arg Tyr Thr Arg Gly Ser Phe Ile Phe Pro Gly Ala
110                 115                 120                 125 caa tcg ttt cct cac cgt cac ttt tct gaa gaa gtt gct gtc ctc gat      913
Gln Ser Phe Pro His Arg His Phe Ser Glu Glu Val Ala Val Leu Asp
                130                 135                 140 ggc tat ttt ggg aag ctt gct gcc ggt agc aag gct gtg att atg ggc      961
Gly Tyr Phe Gly Lys Leu Ala Ala Gly Ser Lys Ala Val Ile Met Gly
            145                 150                 155 aac cct gac aaa aca cag aaa tgg cat gtt tac tct gcc tca gct ggg     1009
Asn Pro Asp Lys Thr Gln Lys Trp His Val Tyr Ser Ala Ser Ala Gly
        160                 165                 170 cct gtt cag tct aat gac cct gtt tac act cta gag atg tgt atg act     1057
Pro Val Gln Ser Asn Asp Pro Val Tyr Thr Leu Glu Met Cys Met Thr
    175                 180                 185 ggt ttg gac agg gag aag gca tct gtc ttt tac aag act gaa gga agc     1105
Gly Leu Asp Arg Glu Lys Ala Ser Val Phe Tyr Lys Thr Glu Gly Ser
190                 195                 200                 205 tcg gct gct cac atg act gtt aga tct ggc ata agg aag atc ctc ccc     1153
Ser Ala Ala His Met Thr Val Arg Ser Gly Ile Arg Lys Ile Leu Pro
                210                 215                 220 aac tct gag ata tgc gat ttt gag ttt gaa ccc tgt ggt tat tcc atg     1201
Asn Ser Glu Ile Cys Asp Phe Glu Phe Glu Pro Cys Gly Tyr Ser Met
            225                 230                 235 aat tct att gaa gga gct gct gtt tca acc att cac att aca cca gaa     1249
Asn Ser Ile Glu Gly Ala Ala Val Ser Thr Ile His Ile Thr Pro Glu
        240                 245                 250 gac ggc ttt agc tat gct agc ttt gaa tca gtt gga tat gat ctg aaa     1297
Asp Gly Phe Ser Tyr Ala Ser Phe Glu Ser Val Gly Tyr Asp Leu Lys
    255                 260                 265 acc atg gag ttg ggt ccc ctg gtt gag agg gtg ctg gca tgt ttt gag     1345
Thr Met Glu Leu Gly Pro Leu Val Glu Arg Val Leu Ala Cys Phe Glu
270                 275                 280                 285 cct gca gag ttc tct att gct ttg cat gct gat gtt gct acc aag tta     1393
Pro Ala Glu Phe Ser Ile Ala Leu His Ala Asp Val Ala Thr Lys Leu
                290                 295                 300 ctg gag cgt gtt tgc tgt gtt gat gtt aag ggc tac tct ctt gct gag     1441
Leu Glu Arg Val Cys Cys Val Asp Val Lys Gly Tyr Ser Leu Ala Glu
```

-continued

```
Leu Glu Arg Val Cys Cys Val Asp Val Lys Gly Tyr Ser Leu Ala Glu
            305                 310                 315 tgg agt cca gaa gaa ttt ggc aag ggt ggt tcc att gtc tac cag aag      1489
Trp Ser Pro Glu Glu Phe Gly Lys Gly Gly Ser Ile Val Tyr Gln Lys
        320                 325                 330 ttc act aag act cct tac tgt gca tct ccc aag tcc gtt ctg aag ggc      1537
Phe Thr Lys Thr Pro Tyr Cys Ala Ser Pro Lys Ser Val Leu Lys Gly
    335                 340                 345 tgc tgg aaa gag gaa gag gag aaa gaa gaa aag gag tagtgtttgt           1586
Cys Trp Lys Glu Glu Glu Glu Lys Glu Glu Lys Glu
350                 355                 360 cttgagggtc gttttgttat tgttgtttta gtgtctgtcg tttgctcatg ttttacctgt    1646
ttgtcagaat aaaggactta agattgtccc atttgtgtca gtttggattt gtaacgattg    1706
tgtgcaaatt ctgaactagt ccggcttctt ggtgttccac cagaagccct atgtgtctgc    1766
attttgttcc ctgttccgtt gtggcttcta ataaaagttt gtttgttgtg tgta          1820

<210> SEQ ID NO 14
<211> LENGTH: 362
<212> TYPE: PRT
<213> ORGANISM: Datura stramonium

<400> SEQUENCE: 14

Met Glu Met Asp Leu Pro Val Ser Ala Ile Gly Phe Glu Gly Phe Glu
1               5                   10                  15

Lys Arg Leu Glu Ile Ser Phe Val Glu Pro Gly Leu Phe Ser Asp Pro
            20                  25                  30

Asn Gly Lys Gly Leu Arg Ser Leu Ser Lys Ala Gln Leu Asp Glu Ile
        35                  40                  45

Leu Gly Pro Ala Glu Cys Thr Ile Val Asp Asn Leu Ser Asn Asp Tyr
    50                  55                  60

Val Asp Ser Tyr Val Leu Ser Glu Ser Ser Leu Phe Val Tyr Ser Tyr
65                  70                  75                  80

Lys Ile Ile Ile Lys Thr Cys Gly Thr Thr Lys Leu Leu Leu Ala Ile
                85                  90                  95

Pro Pro Ile Leu Arg Leu Ala Glu Thr Leu Ser Leu Lys Val Gln Asp
            100                 105                 110

Val Arg Tyr Thr Arg Gly Ser Phe Ile Phe Pro Gly Ala Gln Ser Phe
        115                 120                 125

Pro His Arg His Phe Ser Glu Glu Val Ala Val Leu Asp Gly Tyr Phe
    130                 135                 140

Gly Lys Leu Ala Ala Gly Ser Lys Ala Val Ile Met Gly Asn Pro Asp
145                 150                 155                 160

Lys Thr Gln Lys Trp His Val Tyr Ser Ala Ser Ala Gly Pro Val Gln
                165                 170                 175

Ser Asn Asp Pro Val Tyr Thr Leu Glu Met Cys Met Thr Gly Leu Asp
            180                 185                 190

Arg Glu Lys Ala Ser Val Phe Tyr Lys Thr Glu Gly Ser Ser Ala Ala
        195                 200                 205

His Met Thr Val Arg Ser Gly Ile Arg Lys Ile Leu Pro Asn Ser Glu
    210                 215                 220

Ile Cys Asp Phe Glu Phe Glu Pro Cys Gly Tyr Ser Met Asn Ser Ile
225                 230                 235                 240

Glu Gly Ala Ala Val Ser Thr Ile His Ile Thr Pro Glu Asp Gly Phe
                245                 250                 255

Ser Tyr Ala Ser Phe Glu Ser Val Gly Tyr Asp Leu Lys Thr Met Glu
```

```
                260                   265                   270
Leu Gly Pro Leu Val Glu Arg Val Leu Ala Cys Phe Glu Pro Ala Glu
            275                   280                 285

Phe Ser Ile Ala Leu His Ala Asp Val Ala Thr Lys Leu Leu Glu Arg
        290                   295                 300

Val Cys Cys Val Asp Val Lys Gly Tyr Ser Leu Ala Glu Trp Ser Pro
305                 310                 315                 320

Glu Glu Phe Gly Lys Gly Gly Ser Ile Val Tyr Gln Lys Phe Thr Lys
                325                 330                 335

Thr Pro Tyr Cys Ala Ser Pro Lys Ser Val Leu Lys Gly Cys Trp Lys
            340                 345                 350

Glu Glu Glu Glu Glu Lys Glu Glu Lys Glu
            355                 360

<210> SEQ ID NO 15
<211> LENGTH: 1971
<212> TYPE: DNA
<213> ORGANISM: Oryza sativa
<220> FEATURE:
<221> NAME/KEY: CDS
<222> LOCATION: (537)..(1721)

<400> SEQUENCE: 15
acgcgtccgt tcgttttgg tattcccata cactttgttt ctcttcccg tctcgtggtc    60 gagagaaacc gagaggagag agagggagag gagcgctgcc gattttccgg agggggagat   120 cttttcttc tccctgaagg ttcgagatcg atctgcgacg aggaggagcg gggaatcgta   180
actttatttc cgaggaaatt tcaacaaatt gatgcactaa tggagtccaa gggtggcaaa   240
aagaagtcta gcagtagtcg ttcctccctg atgtacgaag ctcccctcgg ctacagcatt   300
gaggacctcc gacctgccgg cggcatcaag aagttccgct ctgctgctta ctccaactgc   360
gcgaggaagc cctcttgata gccccttgg ctaccttgac ctagtagttt agttactcct   420
ctgaattctc gttttgggct ttcttacatc tctctggcta gctgcttccc agtgaccggg   480
aaggtcatca gtcctgcttc ctttcttcct catctctggc atcgtccttc gaaaca atg   539
                                                              Met
                                                                1 gca gtc ctg tca gtt gct gac tct cca ccg gtc tcg gcg atc ggg ttt   587
Ala Val Leu Ser Val Ala Asp Ser Pro Pro Val Ser Ala Ile Gly Phe
        5                  10                  15 gag gga tat gag aaa cgc ctc gag atc act ttc tcc gag gcg cct gtc   635
Glu Gly Tyr Glu Lys Arg Leu Glu Ile Thr Phe Ser Glu Ala Pro Val
    20                  25                  30 ttt gct gac ccc aat ggc agg ggg ttg cgt gca ctg tca cgt gct cag   683
Phe Ala Asp Pro Asn Gly Arg Gly Leu Arg Ala Leu Ser Arg Ala Gln
 35                  40                  45 att gac tct gtt ctt gat ctg gcg agg tgc acc att gtg tct gag ctc   731
Ile Asp Ser Val Leu Asp Leu Ala Arg Cys Thr Ile Val Ser Glu Leu
 50                  55                  60                  65 tcc aat gag gtc ttc gac tcg tat gtc ctt tct gaa tcg agc ctc ttt   779
Ser Asn Glu Val Phe Asp Ser Tyr Val Leu Ser Glu Ser Ser Leu Phe
                 70                  75                  80 gtg tac cca tac aag att gtg atc aag acc tgt ggg act acc aag ctc   827
Val Tyr Pro Tyr Lys Ile Val Ile Lys Thr Cys Gly Thr Thr Lys Leu
             85                  90                  95 ctg ctc gcc att ccg agg att ctt gag ctt gct gaa gag cta tct ctg   875
Leu Leu Ala Ile Pro Arg Ile Leu Glu Leu Ala Glu Glu Leu Ser Leu
        100                 105                 110 cca ctt gaa gct gtg aag tac tct cgt ggg aca ttc att ttt cct gaa   923
```

```
              Pro Leu Glu Ala Val Lys Tyr Ser Arg Gly Thr Phe Ile Phe Pro Glu
                  115                 120                 125 gca cag ccc tct cca cac aag aac ttc tct gag gag gtt gca gtc ctg        971
Ala Gln Pro Ser Pro His Lys Asn Phe Ser Glu Glu Val Ala Val Leu
130                 135                 140                 145 aac cgc tac ttc ggc ggt ctc aaa tct ggt ggc aac gca tac gtg att       1019
Asn Arg Tyr Phe Gly Gly Leu Lys Ser Gly Gly Asn Ala Tyr Val Ile
                150                 155                 160 gga gat cct gca aag cca ggg cag aag tgg cat gtc tac tat gcc acc       1067
Gly Asp Pro Ala Lys Pro Gly Gln Lys Trp His Val Tyr Tyr Ala Thr
            165                 170                 175 cag cac ccg gag caa cct gtc gtc act ctt gag atg tgc atg act ggg       1115
Gln His Pro Glu Gln Pro Val Val Thr Leu Glu Met Cys Met Thr Gly
        180                 185                 190 ctg gac aag aag aaa gct tct gtc ttc ttc aag act tct gct gat gga       1163
Leu Asp Lys Lys Lys Ala Ser Val Phe Phe Lys Thr Ser Ala Asp Gly
    195                 200                 205 cac aca aca tat gct aag gaa atg acc aag ctc tca ggt atc tct gac       1211
His Thr Thr Tyr Ala Lys Glu Met Thr Lys Leu Ser Gly Ile Ser Asp
210                 215                 220                 225 atc atc cca gag atg gaa gtc tgc gac ttc gat ttc gag ccc tgc ggc       1259
Ile Ile Pro Glu Met Glu Val Cys Asp Phe Asp Phe Glu Pro Cys Gly
                230                 235                 240 tac tcc atg aat gcc atc cac ggc cct gct ttc tca acc att cat gtg       1307
Tyr Ser Met Asn Ala Ile His Gly Pro Ala Phe Ser Thr Ile His Val
                245                 250                 255 act cct gag gat ggc ttc agc tat gcc agc tac gag gtc atg ggc ttc       1355
Thr Pro Glu Asp Gly Phe Ser Tyr Ala Ser Tyr Glu Val Met Gly Phe
            260                 265                 270 aac cct gct tcc ctt gcc tat ggt gac ctt gtc aag agg gtg ttg aga       1403
Asn Pro Ala Ser Leu Ala Tyr Gly Asp Leu Val Lys Arg Val Leu Arg
        275                 280                 285 tgc ttt ggc ccg ttg gag ttc tct gtt gcg gtt acc atc ttt ggt ggc       1451
Cys Phe Gly Pro Leu Glu Phe Ser Val Ala Val Thr Ile Phe Gly Gly
290                 295                 300                 305 cgc aac cat gca ggg acc tgg gcc aag ggg ctg gat gtc ggg gcc tat       1499
Arg Asn His Ala Gly Thr Trp Ala Lys Gly Leu Asp Val Gly Ala Tyr
                310                 315                 320 tct tgc agc aac atg gtt gag cag gag ctg cct tct ggg ggt ttg ctc       1547
Ser Cys Ser Asn Met Val Glu Gln Glu Leu Pro Ser Gly Gly Leu Leu
                325                 330                 335 att tac cag agc ttc act gct act gct gaa atc gcc acc ggg tcg cca       1595
Ile Tyr Gln Ser Phe Thr Ala Thr Ala Glu Ile Ala Thr Gly Ser Pro
            340                 345                 350 cga tct gtt ctg cat tgc ttt gct gat gaa aac acg gag aaa gct ggt       1643
Arg Ser Val Leu His Cys Phe Ala Asp Glu Asn Thr Glu Lys Ala Gly
        355                 360                 365 aaa atg gag gct ctc tac tgg gaa gac gat gct gtc gag gag ata gat       1691
Lys Met Glu Ala Leu Tyr Trp Glu Asp Asp Ala Val Glu Glu Ile Asp
370                 375                 380                 385 ggc aca gag ggt aag aag atg agg agc tgc tgatgaggga agcgcactga        1741
Gly Thr Glu Gly Lys Lys Met Arg Ser Cys
                390                 395 agattaaaga atactcaaaa ctccagtagc gatcactctg ttactttgtg aagcagccag    1801
ccagactatt catatagtac tagtatatgc tatgaccaat gttctttatt atcttgcata    1861
tattctgaat aaaagggctc taggtggtct gctttgtctg ccacagtgag caaaatgtat    1921
ccgaatatca aactttaatg ttgggaatat aatacaagtc attttataat                1971
```

```
<210> SEQ ID NO 16
<211> LENGTH: 395
<212> TYPE: PRT
<213> ORGANISM: Oryza sativa

<400> SEQUENCE: 16
```

| | | | | | | | | | | | | | | |
|---|---|---|---|---|---|---|---|---|---|---|---|---|---|---|
| Met | Ala | Val | Leu | Ser | Val | Ala | Asp | Ser | Pro | Val | Ser | Ala | Ile | Gly |
| 1 | | | | 5 | | | | | 10 | | | | | 15 |
| Phe | Glu | Gly | Tyr | Glu | Lys | Arg | Leu | Glu | Ile | Thr | Phe | Ser | Glu | Ala | Pro |
| | | | 20 | | | | | 25 | | | | | 30 | | |
| Val | Phe | Ala | Asp | Pro | Asn | Gly | Arg | Gly | Leu | Arg | Ala | Leu | Ser | Arg | Ala |
| | | 35 | | | | | 40 | | | | | 45 | | | |
| Gln | Ile | Asp | Ser | Val | Leu | Asp | Leu | Ala | Arg | Cys | Thr | Ile | Val | Ser | Glu |
| 50 | | | | | 55 | | | | | 60 | | | | | |
| Leu | Ser | Asn | Glu | Val | Phe | Asp | Ser | Tyr | Val | Leu | Ser | Glu | Ser | Ser | Leu |
| 65 | | | | | 70 | | | | | 75 | | | | | 80 |
| Phe | Val | Tyr | Pro | Tyr | Lys | Ile | Val | Ile | Lys | Thr | Cys | Gly | Thr | Thr | Lys |
| | | | | 85 | | | | | 90 | | | | | 95 | |
| Leu | Leu | Leu | Ala | Ile | Pro | Arg | Ile | Leu | Glu | Leu | Ala | Glu | Glu | Leu | Ser |
| | | | 100 | | | | | 105 | | | | | 110 | | |
| Leu | Pro | Leu | Glu | Ala | Val | Lys | Tyr | Ser | Arg | Gly | Thr | Phe | Ile | Phe | Pro |
| | | 115 | | | | | 120 | | | | | 125 | | | |
| Glu | Ala | Gln | Pro | Ser | Pro | His | Lys | Asn | Phe | Ser | Glu | Glu | Val | Ala | Val |
| 130 | | | | | 135 | | | | | 140 | | | | | |
| Leu | Asn | Arg | Tyr | Phe | Gly | Gly | Leu | Lys | Ser | Gly | Gly | Asn | Ala | Tyr | Val |
| 145 | | | | | 150 | | | | | 155 | | | | | 160 |
| Ile | Gly | Asp | Pro | Ala | Lys | Pro | Gly | Gln | Lys | Trp | His | Val | Tyr | Tyr | Ala |
| | | | | 165 | | | | | 170 | | | | | 175 | |
| Thr | Gln | His | Pro | Glu | Gln | Pro | Val | Val | Thr | Leu | Glu | Met | Cys | Met | Thr |
| | | | 180 | | | | | 185 | | | | | 190 | | |
| Gly | Leu | Asp | Lys | Lys | Lys | Ala | Ser | Val | Phe | Lys | Thr | Ser | Ala | Asp |
| | | | 195 | | | | | 200 | | | | | 205 | | |
| Gly | His | Thr | Thr | Tyr | Ala | Lys | Glu | Met | Thr | Lys | Leu | Ser | Gly | Ile | Ser |
| | | 210 | | | | | 215 | | | | | 220 | | | |
| Asp | Ile | Ile | Pro | Glu | Met | Glu | Val | Cys | Asp | Phe | Asp | Phe | Glu | Pro | Cys |
| 225 | | | | | 230 | | | | | 235 | | | | | 240 |
| Gly | Tyr | Ser | Met | Asn | Ala | Ile | His | Gly | Pro | Ala | Phe | Ser | Thr | Ile | His |
| | | | | 245 | | | | | 250 | | | | | 255 | |
| Val | Thr | Pro | Glu | Asp | Gly | Phe | Ser | Tyr | Ala | Ser | Tyr | Glu | Val | Met | Gly |
| | | | 260 | | | | | 265 | | | | | 270 | | |
| Phe | Asn | Pro | Ala | Ser | Leu | Ala | Tyr | Gly | Asp | Leu | Val | Lys | Arg | Val | Leu |
| | | 275 | | | | | 280 | | | | | 285 | | | |
| Arg | Cys | Phe | Gly | Pro | Leu | Glu | Phe | Ser | Val | Ala | Val | Thr | Ile | Phe | Gly |
| | 290 | | | | | 295 | | | | | 300 | | | | |
| Gly | Arg | Asn | His | Ala | Gly | Thr | Trp | Ala | Lys | Gly | Leu | Asp | Val | Gly | Ala |
| 305 | | | | | 310 | | | | | 315 | | | | | 320 |
| Tyr | Ser | Cys | Ser | Asn | Met | Val | Glu | Gln | Glu | Leu | Pro | Ser | Gly | Gly | Leu |
| | | | | 325 | | | | | 330 | | | | | 335 | |
| Leu | Ile | Tyr | Gln | Ser | Phe | Thr | Ala | Thr | Ala | Glu | Ile | Ala | Thr | Gly | Ser |
| | | | 340 | | | | | 345 | | | | | 350 | | |
| Pro | Arg | Ser | Val | Leu | His | Cys | Phe | Ala | Asp | Glu | Asn | Thr | Glu | Lys | Ala |
| | | 355 | | | | | 360 | | | | | 365 | | | |
| Gly | Lys | Met | Glu | Ala | Leu | Tyr | Trp | Glu | Asp | Asp | Ala | Val | Glu | Glu | Ile |
| | 370 | | | | | 375 | | | | | 380 | | | | |
| Asp | Gly | Thr | Glu | Gly | Lys | Lys | Met | Arg | Ser | Cys |

```
385                 390                 395

<210> SEQ ID NO 17
<211> LENGTH: 2952
<212> TYPE: DNA
<213> ORGANISM: Oryza sativa
<220> FEATURE:
<221> NAME/KEY: CDS
<222> LOCATION: (1444)..(2619)

<400> SEQUENCE: 17
gcctgggcga ttctagaaag atgtctcttt tgctaatggt tattattagc tgaatcgctg      60
atatggtgaa tccaggaaag tttcatgctt tttgtcctat gtcctgtctt tctttgtcat     120
attcgtacct ttcccagttt gcgatgccca agaagcaacc tttctgttgg aaacatctag     180
tgctcaattc attatttcaa attgttgaaa tcttcaagga gcagtttatt gtgcgcccct     240
gttgattgct cttgtttatt tacaagtggg gatttaggcg ctgggttcat atatgttctt     300
tgtttctgcc aggtttcctt gttaggctct agttttgctc gttgttact gtaaattccc      360 atgtatatta gtttgtgca gtgcgctgtc agcttggcaa atgggctttt cttttcctga     420
tcgaaaaaaa aacaaacctg tgattaacaa ggggaaatta ccttcactgt gcctattggc     480
atcattccaa gttattcatg ctttagttcc tagccattaa cttaagatag aaataagatc     540
ctgccagttc actagttttc ttgtcagttt gatatatact ttgatcttgt cttttctggt     600
tgttttcctt aatttgtct gtgttgttct agtgcttaat tagttgcctc tcagttcttc     660
acattctatg ttttttgagta aaactctgtc catatggccg ttctgttatg tatctcagca    720
atctgcttat attttttttt tgcatcccca cacaattcta tttgacgttg taaaaaagaa     780
gagagataac tagataagcg caactgatgc tctatactta gtttcacggt tcttggttta    840
atgcctaaaa attgtgcact atcagtactt caattatgtt atctagtagt gttttgtctc    900
ctctgaataa tgcctgccat tcttatgctg ctctactgct gagaaaacta cactatttga     960
attactgatt gctaattatg tttcgattaa cagcataaag gaacattttg ttgatgttct    1020
aatggagtca aaaggtggca aaagaagtc tagcagtagt agttccatgt acgaagctcc     1080
cctaggctac aagattgagg acgttcgccc agccggagga atcaagaagt tccagtctgc    1140
tgcttactcc aacgtaagca ccaaaagatt taagcagcat actttaaata acaaaaatat    1200
ttacatttat gaactctggt ttctaatgct tatttggttt atcttttcct ttgcagtgcg    1260
ctcgcaagcc atcctgatat tccttcacat gcctttcccc gtagagtagg aatttcctgc    1320 aattttttcct ttgttttgtt gcaataaatc tcccttggct ggctgctttc tcaatctctt    1380
cccttgtctt ctccgatctc ttcttttcctg tcttgtccac tgctccttgc aacacttgat    1440 caa atg tcg atg tcc ttg gct gat tct tgg ggc tct gcc cct gcc tcg      1488
    Met Ser Met Ser Leu Ala Asp Ser Trp Gly Ser Ala Pro Ala Ser
      1               5                  10                  15 ccc att ggg ttt gaa ggc tat gag aag cgc ctt gag ata aca ttg tct      1536
Pro Ile Gly Phe Glu Gly Tyr Glu Lys Arg Leu Glu Ile Thr Leu Ser
             20                  25                  30 gat gcg ccc gtc ttt gtg gac ccc tgt ggt cgc ggc ctt cgt gcc ctc      1584
Asp Ala Pro Val Phe Val Asp Pro Cys Gly Arg Gly Leu Arg Ala Leu
         35                  40                  45 tca cgt gag cag atc gac tcg ttc ttg gat ctt gca aag tgt acc att      1632
Ser Arg Glu Gln Ile Asp Ser Phe Leu Asp Leu Ala Lys Cys Thr Ile
     50                  55                  60 gta tcc cat ctt tcg aac aag cac ttc gac tca tat gtg ctt tca gag     1680
Val Ser His Leu Ser Asn Lys His Phe Asp Ser Tyr Val Leu Ser Glu
 65                  70                  75
```

```
                                          -continued tcg agc ctt ttt gtt tat ccc cac aag gtt gtt ctg aag acc tgt ggt    1728
Ser Ser Leu Phe Val Tyr Pro His Lys Val Val Leu Lys Thr Cys Gly
 80                  85                  90                  95 aca aca aag ctt ctg ctc tcc att cct cgc atc ctt gag ctt gct gca    1776
Thr Thr Lys Leu Leu Leu Ser Ile Pro Arg Ile Leu Glu Leu Ala Ala
                100                 105                 110 gag ttg tca ctg cct gtt cta tca gtg aag tac tct cgt ggg atg ttc    1824
Glu Leu Ser Leu Pro Val Leu Ser Val Lys Tyr Ser Arg Gly Met Phe
            115                 120                 125 atc ttc cct gga gcg cag cca tca ccg cat cgc agc ttc ttg gag gag    1872
Ile Phe Pro Gly Ala Gln Pro Ser Pro His Arg Ser Phe Leu Glu Glu
        130                 135                 140 gtt tct gtg ctc aac agc ttc ttt ggt ggc ctc aag tca ggt ggc aat    1920
Val Ser Val Leu Asn Ser Phe Phe Gly Gly Leu Lys Ser Gly Gly Asn
    145                 150                 155 gct tat gtc att ggt gat gca ttc aag ccc aag aag aag tgg cat gtc    1968
Ala Tyr Val Ile Gly Asp Ala Phe Lys Pro Lys Lys Lys Trp His Val
160                 165                 170                 175 tac tat gcc aca gaa gag cct gag cag ccc atg gtt aca ctc gag atg    2016
Tyr Tyr Ala Thr Glu Glu Pro Glu Gln Pro Met Val Thr Leu Glu Met
                180                 185                 190 tgc atg act ggg ctg gat gct aag aaa gct gag gtg ttc ttc aag gat    2064
Cys Met Thr Gly Leu Asp Ala Lys Lys Ala Glu Val Phe Phe Lys Asp
            195                 200                 205 tcc act gat ggc tcc tgc tca tca gct aag gag atg act atg ttc tct    2112
Ser Thr Asp Gly Ser Cys Ser Ser Ala Lys Glu Met Thr Met Phe Ser
        210                 215                 220 ggg att tct gaa atc atc cct gag atg gag att tgt gac ttt gag ttt    2160
Gly Ile Ser Glu Ile Ile Pro Glu Met Glu Ile Cys Asp Phe Glu Phe
    225                 230                 235 gac ccg tgt ggg tac tca atg aat ggc att tat ggt ccc gcc gtc tcc    2208
Asp Pro Cys Gly Tyr Ser Met Asn Gly Ile Tyr Gly Pro Ala Val Ser
240                 245                 250                 255 acg atc cat gtc act cct gag gaa ggt ttc agc tat gca agc tat gaa    2256
Thr Ile His Val Thr Pro Glu Glu Gly Phe Ser Tyr Ala Ser Tyr Glu
                260                 265                 270 gca atg aac ttc aat cct agc tcc ttg gtc tac gat gat ttg atc aag    2304
Ala Met Asn Phe Asn Pro Ser Ser Leu Val Tyr Asp Asp Leu Ile Lys
            275                 280                 285 aag gtc ctg gct tgt ttc tgc cct tca gac ttt tcg gtc gct gtt acc    2352
Lys Val Leu Ala Cys Phe Cys Pro Ser Asp Phe Ser Val Ala Val Thr
        290                 295                 300 atc ttc ggt ggg cat ggt ttt gcc aaa tca tgg gca aaa ggt gca gag    2400
Ile Phe Gly Gly His Gly Phe Ala Lys Ser Trp Ala Lys Gly Ala Glu
    305                 310                 315 gtt gat tcc tac atg tgc gat gat ctt gtt gag caa gag ctt cct ggt    2448
Val Asp Ser Tyr Met Cys Asp Asp Leu Val Glu Gln Glu Leu Pro Gly
320                 325                 330                 335 ggc ggt gtg ctg atg tat cag agt ttt act gct gtt act cct ggt gct    2496
Gly Gly Val Leu Met Tyr Gln Ser Phe Thr Ala Val Thr Pro Gly Ala
                340                 345                 350 gtg tca ccg agg tcg acc ttg gat ggc tgg aac agc gat gga gca gag    2544
Val Ser Pro Arg Ser Thr Leu Asp Gly Trp Asn Ser Asp Gly Ala Glu
            355                 360                 365 atg gtt gcg aag agc aaa gag atg agt gtc tgc tgg gaa gga gag aag    2592
Met Val Ala Lys Ser Lys Glu Met Ser Val Cys Trp Glu Gly Glu Lys
        370                 375                 380 gcg gcg aag aag aaa gat gca gat gcc tgagaaatcg gcagttcttc          2639
Ala Ala Lys Lys Lys Asp Ala Asp Ala
    385                 390
```

```
aacctcaagt tgcaagtttg attcatctga agtttctgag acgccttatt tggttctgct    2699
cttgcagttt cggttaagca gctggctggg ctaccggcaa agcatatgtt acttgttcat    2759 tgttcttta tatctgtctg cccaaataag tgctctagat ggtttgctgc gtctgccata     2819
gtgagcaatt cagattgtag tagaattctt atctgttgcc gatgctcttt aagggagaat    2879
gatatgtaac tcgattattt tcaataacta ttgcaacttc cataattttc tgtccattgg    2939
ttatgtttgt ttg                                                       2952

<210> SEQ ID NO 18
<211> LENGTH: 392
<212> TYPE: PRT
<213> ORGANISM: Oryza sativa

<400> SEQUENCE: 18

Met Ser Met Ser Leu Ala Asp Ser Trp Gly Ser Ala Pro Ala Ser Pro
1               5                   10                  15

Ile Gly Phe Glu Gly Tyr Glu Lys Arg Leu Glu Ile Thr Leu Ser Asp
            20                  25                  30

Ala Pro Val Phe Val Asp Pro Cys Gly Arg Gly Leu Arg Ala Leu Ser
        35                  40                  45

Arg Glu Gln Ile Asp Ser Phe Leu Asp Leu Ala Lys Cys Thr Ile Val
    50                  55                  60

Ser His Leu Ser Asn Lys His Phe Asp Ser Tyr Val Leu Ser Glu Ser
65                  70                  75                  80

Ser Leu Phe Val Tyr Pro His Lys Val Val Leu Lys Thr Cys Gly Thr
                85                  90                  95

Thr Lys Leu Leu Leu Ser Ile Pro Arg Ile Leu Glu Leu Ala Ala Glu
            100                 105                 110

Leu Ser Leu Pro Val Leu Ser Val Lys Tyr Ser Arg Gly Met Phe Ile
        115                 120                 125

Phe Pro Gly Ala Gln Pro Ser Pro His Arg Ser Phe Leu Glu Glu Val
    130                 135                 140

Ser Val Leu Asn Ser Phe Phe Gly Gly Leu Lys Ser Gly Gly Asn Ala
145                 150                 155                 160

Tyr Val Ile Gly Asp Ala Phe Lys Pro Lys Lys Lys Trp His Val Tyr
                165                 170                 175

Tyr Ala Thr Glu Glu Pro Glu Gln Pro Met Val Thr Leu Glu Met Cys
            180                 185                 190

Met Thr Gly Leu Asp Ala Lys Lys Ala Glu Val Phe Lys Asp Ser
        195                 200                 205

Thr Asp Gly Ser Cys Ser Ser Ala Lys Glu Met Thr Met Phe Ser Gly
210                 215                 220

Ile Ser Glu Ile Ile Pro Glu Met Glu Ile Cys Asp Phe Glu Phe Asp
225                 230                 235                 240

Pro Cys Gly Tyr Ser Met Asn Gly Ile Tyr Gly Pro Ala Val Ser Thr
                245                 250                 255

Ile His Val Thr Pro Glu Glu Gly Phe Ser Tyr Ala Ser Tyr Glu Ala
            260                 265                 270

Met Asn Phe Asn Pro Ser Ser Leu Val Tyr Asp Asp Leu Ile Lys Lys
        275                 280                 285

Val Leu Ala Cys Phe Cys Pro Ser Asp Phe Val Ala Val Thr Ile
    290                 295                 300

Phe Gly Gly His Gly Phe Ala Lys Ser Trp Ala Lys Gly Ala Glu Val
305                 310                 315                 320
```

```
Asp Ser Tyr Met Cys Asp Asp Leu Val Glu Gln Glu Leu Pro Gly Gly
            325                 330                 335

Gly Val Leu Met Tyr Gln Ser Phe Thr Ala Val Thr Pro Gly Ala Val
        340                 345                 350

Ser Pro Arg Ser Thr Leu Asp Gly Trp Asn Ser Asp Gly Ala Glu Met
            355                 360                 365

Val Ala Lys Ser Lys Glu Met Ser Val Cys Trp Glu Gly Glu Lys Ala
        370                 375                 380

Ala Lys Lys Lys Asp Ala Asp Ala
385                 390

<210> SEQ ID NO 19
<211> LENGTH: 2523
<212> TYPE: DNA
<213> ORGANISM: Populus deltoids.
<220> FEATURE:
<221> NAME/KEY: modified_base
<222> LOCATION: (339)
<223> OTHER INFORMATION: a, c, t, g, unknown or other

<400> SEQUENCE: 19
ttaaccctat atttctctca gaactcacat aaaaaatatt gcgagtttag ggtcataaaa      60
atctctatca tcacaaacaa atatagggtt tgttgatttg gtggctgttt tcgccgtctt     120
tgctttcaaa attcaatctt gacctgtttc ttttatgctt tttgaatagg taatatatac     180
attgtttgtt ttgcttgctt tggttttgta atctggtgat cttgtttaat tcttttttggc    240 tttggtttgt aggttttttt ttttgaacyt gagaaagagg ggggttttca arggagacta    300
gcttttcaag awttgatata ttttattggt aagttttttnt tttccgtttt ttggtaatag    360
ttgcatggat tcttggtgta gatgttgatt tggacttgtt tttgtattgt tgtcctttat     420
gttttatgtg tatgttaatt gttctgatcc ttgatataat gtaaatctga ggcttttatt     480
tttatggatt cgttaaggtg tatggacttg gtttatggtt ttggtcttga aaaaaaaatt    540
aggcttagca gttttcttc tgagaataac ttattttatt ttattattta aaattaaatg      600
gtgtttggga atttgaattc tttctctttg gtattttttc tatccttgtg aatctgttta     660
gtcttttaaa ttcaatattt tatttatttt tacttatgat ttggtgattg attagttatt     720
tttgtagctt gtattgtctg ttgatttta atctccaata tgtcttactt ctcagttttt     780
ttcaatttgc tattggaatt ttgctattat ttttaagatt gtagactagt ttgctttgag     840
ttttgtgcta attgcaatcc ttcttgtgtg attcttacag gactgaatga tctaatggag     900
tctaaaggtg gcaagaagaa gtctagtagt agtagtagta gtaaatcctt atgttaagaa     960
gctcccctcg gttacagcat tgaagacctc agacctgctg gtggaatcaa gaagttcaga    1020
tctgctgcat actccaacgt gagtttgaag ttaatcgatc tgttttttcct ttggcatttc    1080 attgtgcgac tggtttccta atctgtgtc atgtttattt gtgcagtgcg ttcgaaaacc      1140
atcctgagat tttccaagtg ttgacataac cccatttag ctatttcgca cgctcagttg     1200
tctttaktct gtttttctgt tctgctttcc tcgttctctt gtactctttg ctgcactttt    1260
catttgttga ctgtgaggtc agatggcgct gccagtctct gcaatcggat ttgaaggtta    1320
cgaaaaaagg cttgaaatat cttttcctaga gcctggcttc ttttctgacc tgaagggaa    1380 gggcctgagg tctttgtcca aggctcaatt ggacgagatt ctcagaccag ctgaatgtac    1440
tattgttgat tcgctatcaa atgaccaggt tgattcttat gtcctgtcgg aatccagtct    1500
ctttgtgtac ccttacaaag ttattatcaa aacatgtggg actaccaaac tgcttctctc    1560
```

-continued

```
gataccggtg attcttaagc tcgctgatgc cctttcactc actgtatgtt ctgtgaggta    1620
tactcgtggg agctttctat gccctggggc tcagccattt ccacaccgca acttctgtga    1680
ggaggtagct gtccttgacg atcacttcag taaacttggt ttaaacagtg tggcatatgt    1740
gatgggtggt cttgacaaaa ctcagaaatg gcatgtttac tctgcctctg ccgatataga    1800
gagccattct ggccctgttt acactctgga aatgtgcatg actggtttgg caggaaaca     1860 agcatctgtt ttctacaaaa cacattccag ttcagctgct gcgatgactg aggattccgg    1920
tataaggaaa atccttccac agtctgagat ctgtgatttt gattttgacc catgtggtta    1980
ctctatgaat gccattgaag ggagtgcaat tccacaatc cacgtcactc cagaagatgg      2040
tttcagctat gcaagttttg aggctgtggg ctatgatctt caagatttga atttgagtcg    2100
gctgcttgaa agggtcttgg cttgctttga accgaccatg ttctccgttg ccttgcattc    2160
taatatcaag ggtgccgaac ttagagcaaa gtttcccctg gacgtggaag gttactctgg    2220
cggaggaggg aactatgaaa tgcttgggaa aggtggatcg atcatctacc acagctttgc    2280
aaggactgga ggcagtgcat ctcccaggtc tatcctgaaa tgttgttgga gtgaggatga    2340
gaaggacgag gaagctgaag agaagtagtt cttttcagct atttgttttt tccttttatt    2400
ttttccttga ataaatgtca tggggttatg attctgagtt cttgaggcat ttgtccatgc    2460
ctcgtgtctt tcattatcga tttagttttg acttcggatt aataaagggg tttgtgttat    2520
cag                                                                 2523
```

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
   oligonucleotide

<400> SEQUENCE: 20
atcccatgga ttcggccttg cctg                                          24

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
   oligonucleotide

<400> SEQUENCE: 21
gtctagacta ctccttctct tctttctctt catc                               34

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
   oligonucleotide

<400> SEQUENCE: 22
tatcgtttta cttcactggt cggtg                                         25

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 23
aatctcacca acccaactcc					20

<210> SEQ ID NO 24
<211> LENGTH: 1658
<212> TYPE: DNA
<213> ORGANISM: Nicotiana tabacum
<220> FEATURE:
<221> NAME/KEY: CDS
<222> LOCATION: (364)..(1446)

<400> SEQUENCE: 24

```
atggagtcga aggtggtaa aaactctagt agtaaatcct taccctacga agcacccctc      60
ggctacagta ttgaagacgt tcggccaaac ggtggaatca agaagttcag atcagctgct     120
tactccaact gcgctcgcaa accatcctga cattccttaa gcttctctcc tgcacgtgtc     180
tcctgacaca aaaagaaaa aatccccaaa aaagttcct tctgtcaatt gttttgttg       240 ttaaaccctc actccttttc ctcaatttct tccttctgct gctttctgct cttgctctcc    300
ttggctgtga caattttct ttaaaagatc atttgttgct gtgaacatat ttttttttat     360 cta atg gat tcg gcc ttg cct gtc tct gcc att ggt ttt gaa ggt ttc      408
    Met Asp Ser Ala Leu Pro Val Ser Ala Ile Gly Phe Glu Gly Phe
    1               5                   10                  15 gag aag agg ctt gaa att tct ttt ttc gag cct ggt ctg ttt gct gat      456
Glu Lys Arg Leu Glu Ile Ser Phe Phe Glu Pro Gly Leu Phe Ala Asp
                20                  25                  30 ccc aac gga aaa gga ctt cga tct ctc tca aag gca caa ttg gat gag      504
Pro Asn Gly Lys Gly Leu Arg Ser Leu Ser Lys Ala Gln Leu Asp Glu
            35                  40                  45 att ctc gga cct gct gag tgc acc ata gtt gat tcc cta tca aat gac      552
Ile Leu Gly Pro Ala Glu Cys Thr Ile Val Asp Ser Leu Ser Asn Asp
        50                  55                  60 gat gtt gat tct tat gtc ctc tcc gag tcg agc ctc ttt gtt tat tct      600
Asp Val Asp Ser Tyr Val Leu Ser Glu Ser Ser Leu Phe Val Tyr Ser
    65                  70                  75 tac aag ata atc atc aaa acc tgt ggc acc aca aag ttg ctt ctc gca      648
Tyr Lys Ile Ile Ile Lys Thr Cys Gly Thr Thr Lys Leu Leu Leu Ala
80                  85                  90                  95 att ccg ccc atc cta aag ttg gct gag acc ctg tct ctc aaa gta caa      696
Ile Pro Pro Ile Leu Lys Leu Ala Glu Thr Leu Ser Leu Lys Val Gln
                100                 105                 110 gac gtg agg tat acc cgt ggg agc ttc att ttc cct ggc gct cag tcg      744
Asp Val Arg Tyr Thr Arg Gly Ser Phe Ile Phe Pro Gly Ala Gln Ser
            115                 120                 125 ttt cct cat cgt cac ttc tct gaa gaa gtt gct gtc ctc gat ggc tat      792
Phe Pro His Arg His Phe Ser Glu Glu Val Ala Val Leu Asp Gly Tyr
        130                 135                 140 ttt gga aag ctt gct gcc ggt agc aag gct gtg att atg ggc agt cct      840
Phe Gly Lys Leu Ala Ala Gly Ser Lys Ala Val Ile Met Gly Ser Pro
    145                 150                 155 gac aaa gca cag aaa tgg cat gtt tac tct gcc tct gca gga cct att      888
Asp Lys Ala Gln Lys Trp His Val Tyr Ser Ala Ser Ala Gly Pro Ile
160                 165                 170                 175 cag tct aat gac cct gtt tac act ctt gag atg tgt atg act ggt ttg      936
Gln Ser Asn Asp Pro Val Tyr Thr Leu Glu Met Cys Met Thr Gly Leu
                180                 185                 190 gac agg gag aag gca tct gtc ttt tac aag act gaa gga agc tcg gct      984
Asp Arg Glu Lys Ala Ser Val Phe Tyr Lys Thr Glu Gly Ser Ser Ala
            195                 200                 205
```

-continued

| | | |
|---|---|---|
| gct cat atg act gtt cga tct gga ata agg aag atc ctc ccc aat tct<br>Ala His Met Thr Val Arg Ser Gly Ile Arg Lys Ile Leu Pro Asn Ser<br>210                           215                       220 | 1032 |
| gag ata tgc gat ttt gag ttt gaa ccc tgt ggt tat tcc atg aat tca<br>Glu Ile Cys Asp Phe Glu Phe Glu Pro Cys Gly Tyr Ser Met Asn Ser<br>225                          230                       235 | 1080 |
| att gaa gga gct gca ctc tca acc att cac att acc ccg gaa gat ggc<br>Ile Glu Gly Ala Ala Leu Ser Thr Ile His Ile Thr Pro Glu Asp Gly<br>240                       245                      250                   255 | 1128 |
| ttt agc tat gct agc ttt gaa gca gtt ggg tat gac atg aaa acc atg<br>Phe Ser Tyr Ala Ser Phe Glu Ala Val Gly Tyr Asp Met Lys Thr Met<br>                   260                       265                       270 | 1176 |
| aag ctg ggt ccc ctg gtt gag agg gtg ctg gca tgt ttc cag cca gat<br>Lys Leu Gly Pro Leu Val Glu Arg Val Leu Ala Cys Phe Gln Pro Asp<br>275                           280                       285 | 1224 |
| gag ttc tct att gct ttg cat gct gat gtt gct acc aag tta ctg gag<br>Glu Phe Ser Ile Ala Leu His Ala Asp Val Ala Thr Lys Leu Leu Glu<br>                   290                       295                       300 | 1272 |
| cgt gtt tgc tct ctt gat gtg aaa ggc tac tct ctt gct gag tgg agt<br>Arg Val Cys Ser Leu Asp Val Lys Gly Tyr Ser Leu Ala Glu Trp Ser<br>305                           310                       315 | 1320 |
| cca gaa gaa ttt ggc aag ggt ggt tcc att gtc tac cag aag ttc acc<br>Pro Glu Glu Phe Gly Lys Gly Gly Ser Ile Val Tyr Gln Lys Phe Thr<br>320                       325                       330                   335 | 1368 |
| aga act cct ttc tgt gga tct ccc aag tcc gtt ctg aag ggc tgc tgg<br>Arg Thr Pro Phe Cys Gly Ser Pro Lys Ser Val Leu Lys Gly Cys Trp<br>                   340                      345                       350 | 1416 |
| aaa gaa gat gaa gag aaa gaa gag aag gag tagtgtcttg agggctgtgt<br>Lys Glu Asp Glu Glu Lys Glu Glu Lys Glu<br>355                           360 | 1466 |
| tgttttttgt ttcagtgtcc gtgtctgtct ctgtctgtgt cggtgtcgtt tgttttttca | 1526 |
| gtgtttctcc gaataaagta cttgatgtcc aagctgtgtc gtttggattt gtaatgccga | 1586 |
| tgtgcaaatt ctgaactatt cttggctttt tgtgttccac ccgaagccct atgaacctgc | 1646 |
| attttgaata aa | 1658 |

<210> SEQ ID NO 25
<211> LENGTH: 361
<212> TYPE: PRT
<213> ORGANISM: Nicotiana tabacum

<400> SEQUENCE: 25

Met Asp Ser Ala Leu Pro Val Ser Ala Ile Gly Phe Glu Gly Phe Glu
1                5                    10                 15

Lys Arg Leu Glu Ile Ser Phe Phe Glu Pro Gly Leu Phe Ala Asp Pro
                20                    25                        30

Asn Gly Lys Gly Leu Arg Ser Leu Ser Lys Ala Gln Leu Asp Glu Ile
            35                        40                        45

Leu Gly Pro Ala Glu Cys Thr Ile Val Asp Ser Leu Ser Asn Asp Asp
    50                        55                        60

Val Asp Ser Tyr Val Leu Ser Glu Ser Ser Leu Phe Val Tyr Ser Tyr
65                70                    75                    80

Lys Ile Ile Ile Lys Thr Cys Gly Thr Thr Lys Leu Leu Leu Ala Ile
                   85                    90                    95

Pro Pro Ile Leu Lys Leu Ala Glu Thr Leu Ser Leu Lys Val Gln Asp
                100                   105                   110

Val Arg Tyr Thr Arg Gly Ser Phe Ile Phe Pro Gly Ala Gln Ser Phe
            115                    120                    125

```
Pro His Arg His Phe Ser Glu Glu Val Ala Val Leu Asp Gly Tyr Phe
    130                 135                 140

Gly Lys Leu Ala Ala Gly Ser Lys Ala Val Ile Met Gly Ser Pro Asp
145                 150                 155                 160

Lys Ala Gln Lys Trp His Val Tyr Ser Ala Ser Ala Gly Pro Ile Gln
                165                 170                 175

Ser Asn Asp Pro Val Tyr Thr Leu Glu Met Cys Met Thr Gly Leu Asp
            180                 185                 190

Arg Glu Lys Ala Ser Val Phe Tyr Lys Thr Glu Gly Ser Ser Ala Ala
        195                 200                 205

His Met Thr Val Arg Ser Gly Ile Arg Lys Ile Leu Pro Asn Ser Glu
    210                 215                 220

Ile Cys Asp Phe Glu Phe Glu Pro Cys Gly Tyr Ser Met Asn Ser Ile
225                 230                 235                 240

Glu Gly Ala Ala Leu Ser Thr Ile His Ile Thr Pro Glu Asp Gly Phe
                245                 250                 255

Ser Tyr Ala Ser Phe Glu Ala Val Gly Tyr Asp Met Lys Thr Met Lys
            260                 265                 270

Leu Gly Pro Leu Val Glu Arg Val Leu Ala Cys Phe Gln Pro Asp Glu
        275                 280                 285

Phe Ser Ile Ala Leu His Ala Asp Val Ala Thr Lys Leu Leu Glu Arg
    290                 295                 300

Val Cys Ser Leu Asp Val Lys Gly Tyr Ser Leu Ala Glu Trp Ser Pro
305                 310                 315                 320

Glu Glu Phe Gly Lys Gly Ser Ile Val Tyr Gln Lys Phe Thr Arg
                325                 330                 335

Thr Pro Phe Cys Gly Ser Pro Lys Ser Val Leu Lys Gly Cys Trp Lys
            340                 345                 350

Glu Asp Glu Glu Lys Glu Glu Lys Glu
        355                 360

<210> SEQ ID NO 26
<211> LENGTH: 1086
<212> TYPE: DNA
<213> ORGANISM: Populus deltoides
<220> FEATURE:
<221> NAME/KEY: CDS
<222> LOCATION: (1)..(1083)

<400> SEQUENCE: 26 atg gcg ctg cca gtc tct gca atc gga ttt gaa ggt tac gaa aaa agg        48
Met Ala Leu Pro Val Ser Ala Ile Gly Phe Glu Gly Tyr Glu Lys Arg
1               5                   10                  15 ctt gaa ata tct ttc cta gag cct ggc ttc ttt tct gac cct gaa ggg        96
Leu Glu Ile Ser Phe Leu Glu Pro Gly Phe Phe Ser Asp Pro Glu Gly
            20                  25                  30 aag ggc ctg agg tct ttg tcc aag gct caa ttg gac gag att ctc aga       144
Lys Gly Leu Arg Ser Leu Ser Lys Ala Gln Leu Asp Glu Ile Leu Arg
        35                  40                  45 cca gct gaa tgt act att gtt gat tcg cta tca aat gac cag gtt gat       192
Pro Ala Glu Cys Thr Ile Val Asp Ser Leu Ser Asn Asp Gln Val Asp
    50                  55                  60 tct tat gtc ctg tcg gaa tcc agt ctc ttt gtg tac cct tac aaa gtt       240
Ser Tyr Val Leu Ser Glu Ser Ser Leu Phe Val Tyr Pro Tyr Lys Val
65                  70                  75                  80 att atc aaa aca tgt ggg act acc aaa ctg ctt ctt tcg ata ccg gtg       288
Ile Ile Lys Thr Cys Gly Thr Thr Lys Leu Leu Leu Ser Ile Pro Val
                85                  90                  95
```

```
att ctt aag ctc gct gat gcc ctt tca ctc act gta tgt tct gtg agg        336
Ile Leu Lys Leu Ala Asp Ala Leu Ser Leu Thr Val Cys Ser Val Arg
        100                 105                 110 tat act cgt ggg agc ttt cta tgc cct ggg gct cag cca ttt cca cac        384
Tyr Thr Arg Gly Ser Phe Leu Cys Pro Gly Ala Gln Pro Phe Pro His
            115                 120                 125 cga aac ttc tgt gag gag gta gct gtc ctt gac gat cac ttc agt aaa        432
Arg Asn Phe Cys Glu Glu Val Ala Val Leu Asp Asp His Phe Ser Lys
    130                 135                 140 ctt ggt tta aac agt gtg gca tat gtg atg ggt ggt ctt gac aaa act        480
Leu Gly Leu Asn Ser Val Ala Tyr Val Met Gly Gly Leu Asp Lys Thr
145                 150                 155                 160 cag aaa tgg cat gtt tac tct gcc tct gcc gat ata ggg agc cat tct        528
Gln Lys Trp His Val Tyr Ser Ala Ser Ala Asp Ile Gly Ser His Ser
                165                 170                 175 ggc cct gtt tac acc ctg gaa atg tgc atg act ggt ttg ggc agg aaa        576
Gly Pro Val Tyr Thr Leu Glu Met Cys Met Thr Gly Leu Gly Arg Lys
            180                 185                 190 caa gca tct gtt ttc tac aaa aca cat tcc agt tca gct gct gcg atg        624
Gln Ala Ser Val Phe Tyr Lys Thr His Ser Ser Ser Ala Ala Ala Met
        195                 200                 205 act gag gat tcc ggt ata agg aaa atc ctt cca cag tct gag atc tgt        672
Thr Glu Asp Ser Gly Ile Arg Lys Ile Leu Pro Gln Ser Glu Ile Cys
    210                 215                 220 gat ttt gat ttt gac cct tgt ggt tac tcc atg aat gcc att gaa ggg        720
Asp Phe Asp Phe Asp Pro Cys Gly Tyr Ser Met Asn Ala Ile Glu Gly
225                 230                 235                 240 agt gca att tcc aca atc cac gtc act cca gaa gat ggt ttc agc tat        768
Ser Ala Ile Ser Thr Ile His Val Thr Pro Glu Asp Gly Phe Ser Tyr
                245                 250                 255 gca agt ttt gag gct gtg ggc tat gat ctt caa gat ttg aat ttg agt        816
Ala Ser Phe Glu Ala Val Gly Tyr Asp Leu Gln Asp Leu Asn Leu Ser
            260                 265                 270 cgg ctg ctt gaa agg gtc ttg gct tgc ttt gat ccg acc aag ttc tcc        864
Arg Leu Leu Glu Arg Val Leu Ala Cys Phe Asp Pro Thr Lys Phe Ser
        275                 280                 285 gtt gcc ttg cat tct aat atc aag ggt gcc gaa ctt aga gca aag ttt        912
Val Ala Leu His Ser Asn Ile Lys Gly Ala Glu Leu Arg Ala Lys Phe
    290                 295                 300 ccc ctg gac gtg gaa ggt tac tct ggc gga gga ggg aac tat gaa atg        960
Pro Leu Asp Val Glu Gly Tyr Ser Gly Gly Gly Gly Asn Tyr Glu Met
305                 310                 315                 320 ctt ggg aaa ggt gga tcg atc atc tac cac agc ttt gca agg act gga       1008
Leu Gly Lys Gly Gly Ser Ile Ile Tyr His Ser Phe Ala Arg Thr Gly
                325                 330                 335 ggc agt gca tct ccc agg tct atc ctg aaa tgt tgt tgg agt gag gat       1056
Gly Ser Ala Ser Pro Arg Ser Ile Leu Lys Cys Cys Trp Ser Glu Asp
            340                 345                 350 gag aag gac gag gaa gct gaa gag aag tag                              1086
Glu Lys Asp Glu Glu Ala Glu Glu Lys
        355                 360

<210> SEQ ID NO 27
<211> LENGTH: 361
<212> TYPE: PRT
<213> ORGANISM: Populus deltoides

<400> SEQUENCE: 27

Met Ala Leu Pro Val Ser Ala Ile Gly Phe Glu Gly Tyr Glu Lys Arg
 1               5                  10                  15
```

```
Leu Glu Ile Ser Phe Leu Glu Pro Gly Phe Ser Asp Pro Gly
            20                  25                  30

Lys Gly Leu Arg Ser Leu Ser Lys Ala Gln Leu Asp Glu Ile Leu Arg
        35                  40                  45

Pro Ala Glu Cys Thr Ile Val Asp Ser Leu Ser Asn Asp Gln Val Asp
    50                  55                  60

Ser Tyr Val Leu Ser Glu Ser Ser Leu Phe Val Tyr Pro Tyr Lys Val
65                  70                  75                  80

Ile Ile Lys Thr Cys Gly Thr Thr Lys Leu Leu Leu Ser Ile Pro Val
                85                  90                  95

Ile Leu Lys Leu Ala Asp Ala Leu Ser Leu Thr Val Cys Ser Val Arg
            100                 105                 110

Tyr Thr Arg Gly Ser Phe Leu Cys Pro Gly Ala Gln Pro Phe Pro His
            115                 120                 125

Arg Asn Phe Cys Glu Glu Val Ala Val Leu Asp Asp His Phe Ser Lys
            130                 135                 140

Leu Gly Leu Asn Ser Val Ala Tyr Val Met Gly Gly Leu Asp Lys Thr
145                 150                 155                 160

Gln Lys Trp His Val Tyr Ser Ala Ser Ala Asp Ile Gly Ser His Ser
                165                 170                 175

Gly Pro Val Tyr Thr Leu Glu Met Cys Met Thr Gly Leu Gly Arg Lys
            180                 185                 190

Gln Ala Ser Val Phe Tyr Lys Thr His Ser Ser Ala Ala Ala Met
            195                 200                 205

Thr Glu Asp Ser Gly Ile Arg Lys Ile Leu Pro Gln Ser Glu Ile Cys
    210                 215                 220

Asp Phe Asp Phe Asp Pro Cys Gly Tyr Ser Met Asn Ala Ile Glu Gly
225                 230                 235                 240

Ser Ala Ile Ser Thr Ile His Val Thr Pro Glu Asp Gly Phe Ser Tyr
                245                 250                 255

Ala Ser Phe Glu Ala Val Gly Tyr Asp Leu Gln Asp Leu Asn Leu Ser
            260                 265                 270

Arg Leu Leu Glu Arg Val Leu Ala Cys Phe Asp Pro Thr Lys Phe Ser
            275                 280                 285

Val Ala Leu His Ser Asn Ile Lys Gly Ala Glu Leu Arg Ala Lys Phe
    290                 295                 300

Pro Leu Asp Val Glu Gly Tyr Ser Gly Gly Gly Asn Tyr Glu Met
305                 310                 315                 320

Leu Gly Lys Gly Gly Ser Ile Ile Tyr His Ser Phe Ala Arg Thr Gly
                325                 330                 335

Gly Ser Ala Ser Pro Arg Ser Ile Leu Lys Cys Cys Trp Ser Glu Asp
            340                 345                 350

Glu Lys Asp Glu Glu Ala Glu Glu Lys
            355                 360

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ccatggcgct gccagtctct gcaatc                                           26
```

```
<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tctagactac ttctcttcag cttcctc                                            27
```